US008399258B2

(12) United States Patent
Barzilai

(10) Patent No.: US 8,399,258 B2
(45) Date of Patent: Mar. 19, 2013

(54) BIOLOGICAL MARKERS FOR LONGEVITY AND DISEASES AND USES THEREOF

(75) Inventor: Nir Barzilai, Hartsdale, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 441 days.

(21) Appl. No.: 12/315,845

(22) Filed: Dec. 5, 2008

(65) Prior Publication Data

US 2009/0155915 A1 Jun. 18, 2009

Related U.S. Application Data

(63) Continuation of application No. 11/229,327, filed on Sep. 16, 2005, now Pat. No. 7,491,543, which is a continuation-in-part of application No. PCT/US2004/008876, filed on Mar. 19, 2004.

(60) Provisional application No. 60/456,304, filed on Mar. 20, 2003, provisional application No. 60/508,420, filed on Oct. 3, 2003.

(51) Int. Cl.
*G01N 33/92* (2006.01)
(52) U.S. Cl. ........................................ 436/71
(58) Field of Classification Search .................. 530/359; 436/71
See application file for complete search history.

(56) References Cited

U.S. PATENT DOCUMENTS 7,598,227 B2 * 10/2009 Crooke et al. .............. 514/44 R

OTHER PUBLICATIONS

Schoonjans et al., FEBSW Letters 452, 160-164 (1999).*
Anber, V et al., entitled "Interaction of Very-Low-Density, Intermediate-Density, and Low-Density Lipoproteins With Human Arterial Wall Proteoglycans," Arterioscler Thromb Vasc Biol. 1997;17:2507-2514.
Arai, Y et al., entitled "Lipid and Lipoprotein Profile of Japanese Centenarians-Hige Prevalence of Hypo Beta Lipoproteinemia," Nippon Ronen Igakkai Zasshi, Jpn J Geriat 1997; 34:202-208.
Arai, T et al., entitled "Particle size analysis of high density lipoproteins in patients with genetic cholesteryl ester transfer protein deficiency," Clinica Chimic Acta 301 (2000) 103-117.
Austin, M A, entitled "Triglyceride, Small, Dense-Low-density Lipoprotein, and the Atherogenic Lipoprotein Phenotype," Current Atherosclerosis Reports 2000, 2:200-207.
Atzmon, G et al., entitled "Plasma HDL Levels Highly Correlate With Cognitive Function in Exceptional Longevity," Journal of Gerontology: Medical Sciences, 2002, vol. 57A, No. 11, M712-M715.
Atzmon, G et al., entitled "Clinical Phenotype of Families with Longevity," J Am Geriatr Soc 52:274-277, 2004.
Atzmon, G et al., entitled "Clinical Phenotype of Families with Longevity," Mechanisms of Ageing and Development 126 (2005), 341-345.

Barzilai, N et al., entitled "Einstein's institute for aging research: collaborative and programmatic approaches in the search for successful aging," Experimental Gerontology 39 (2004) 151-157.
Barzilai, N et al., entitled "Offspring of Centenarians Have a Favorable Lipid Profile," J Am Geriatr Soc 49:76-79, 2001.
Barzilai, N entitled "Discovering the Secrets of Successful Longevity," Journal of Gerontology: Medical Sciences 2003, vol. 58A, No. 3, 225-226.
Barzilai, N et al., entitled "Searching for Human Longevity Genes: The Future History of Gerontology in the Post-genomic Era," Journal of Gerontology: Medical Sciences, 2001, vol. 56A, No. 2, M83-M87.
Barzilai, N et al., entitled "Unique Lipoprotein Phenotype and Genotype Associated with Exceptional Longevity," JAMA, Oct. 15, 2003, vol. 290, No. 15, 2030-2040.
Barbagallo, C M et al., entitled "Liporprotein Profile and High-Density Lipoproteins: Subfractions Distribution in Centenarians," Gerontology 1998;44:106-110.
Bjornheden, T et al., entitled "Accumulation of lipoprotein fractions and subfractions in the arterial wall, determined in an in vitro perfusion system," Atherosclerosis 123 (1996) 43-56.
Blake, G J et al., entitled "Low-Density Lipoprotein Particle Concentration and Size as Determined by Nuclear Magnetic Resonance Spectroscopy as Predictors of Cardiovascular Disease in Women," Circulation, 2002;106:1930-1937.
Campos, H et al., entitled "LDL Particle Size Distribution: Results from the Framingham Offspring Study," Arteriosclerosis and Thrombosis 1992;12:1410-1419.
Chait, A et al., entitled "Susceptibility of Small, Dense, Low-Density Lipoproteins to Oxidative Modification in Subjects with the Atherogenic Lipoprotein Phenotype, Pattern B," The American Journal of Medicine, Apr. 1993, vol. 94, 350-356.
Ettinger, W H. et al., entitled "High Density Lipoprotein Cholesterol Subfractions in Older People," Journal of Gerontology: Medical Sciences 1994, vol. 49, No. 3, M116-M122.
Evert, J et al., entitled "Mobidity Profiles of Centenarians: Survivors, Delayers, and Escapers," Journal of Gerontology: Medical Sciences, 2003, vol. 58A, No. 3, 232-237.
Ferrara, A et al., entitled "Total, LDL, and HDL Cholesterol Decrease With Age in Older Men and Women: The Rancho Bernardo Study 1984-1994," Circulation, 1997;96:37-43.
Gardner, C D et al., entitled "Association of Small Low-Density Lipoprotein Particles with the Incidence of Coronary Artery Disease in Men and Women," JAMA, Sep. 18, 1996, vol. 276, No. 11, 875-881.
Kamigaki, A S et al., entitled "Low Density Lipoprotein Particle Size and Risk of Early-Onset Myocardial Infarction in Women," American Journal of Epidemiology, 2001, vol. 153, No. 10, 939-945.
Lamarche, B et al., entitled "Small, Dense Low-Density Lipoprotein Particles as a Predictor of the Risk of Ischemic Heart Disease in Men: Prospective Results from the Quebec Cardiovascular Study," Circulation, 1997;95:69-75.

(Continued)

*Primary Examiner* — Chih-Min Kam
(74) *Attorney, Agent, or Firm* — Amster, Rothstein & Ebenstein LLP

(57) ABSTRACT

This invention provides methods of using of the sizes and levels of high-density lipoprotein (HDL) and low-density lipoprotein (LDL) particles, the −641 allele of the promoter of the gene encoding apolipoprotein C-3 (APOC-3), the 405 allele of the gene encoding cholesteryl ester transfer protein (CETP), and plasma levels of insulin-like growth factor-1 (IGF-1), adiponectin, CETP and APOC-3, for determining and increasing an individual's likelihood of longevity and of retaining cognitive function during aging, and for determining and decreasing an individual's likelihood of developing a cardiovascular-, metabolic- or age-related disease.

7 Claims, 25 Drawing Sheets

OTHER PUBLICATIONS

Libby, P, entitled "Managing the Risk of Atherosclerosis: The Role of High-Density Lipoprotein," Am J Cardiol 2001;88(suppl):3N-8N.

Malaguarnera, M et al., entitled "Lipid profile variations in a group of healthy elderly and centenarians," European Review for Medical and Pharmacological Sciences, 1998;2:75-79.

Merched, A et al., entitled "Decreased high-density lipoprotein cholesterol and serum apolipoprotein Al concentrations are highly correlated with the severity of Alzheimer's disease," Neurobiology of Aging 21 (2000) 27-30.

Pascot, A et al., entitled "HDL particle size: a marker of the gender difference in the metabolic risk profile," Atherosclerosis 160 (2002) 399-406.

Perls, T T et al., entitled "Siblings of centenarians live longer," The Lancet, vol. 351, May 23, 1998, 1560.

Perls, T T et al., entitled "Life-long sustained mortality advantage of siblings of centenarians," PNAS, Jun. 11, 2002, vol. 99, No. 12, 8442-8447.

Stampfer, M J et al., entitled "A Prospective Study of Triglyceride Level, Low-Density Lipoprotein Particle Diameter, and Risk of Myocardial Infarction," JAMA, Sep. 18, 1996, vol. 276, No. 11, 882-888.

Superko, R H, entitled "Small, Dense Low-Density Lipoprotein Subclass Pattern B: Issues for the Clinician," Current Atherosclerosis Reports 1999, 1:50-57.

Vakkilainen, J et al., entitled "Endothelial Dysfunction in Men with Small LDL Particles," Circulation, 2000,102:716-721.

Van Exel, E et al., entitled "Association between High-Density Lipoprotein and Cognitive Impairment in the Oldest Old," Ann Neurol 2002;51:716-721.

Von Eckardstein, A et al., entitled "Physiological role and clinical relevance of high-density lipoprotein subclasses," Current Opinion in Lipidology 1994, 5:404-416.

Wilson, P W F et al., entitled "Determinants of Change in Total Cholesterol and HDL-C With Age: The Framingham Study," Journal of Gerontology: Medical Sciences 1994, vol. 49, No. 6, M252-M257.

Yoshida, A et al., entitled "Variability in Cholesteryl Ester Transfer Protein in Healthy Japanese Hyper-HDL-cholesterolemic Subjects," Internal Medicine vol. 41, No. 5, May 2002, 357-359.

Arai Y et al., entitled "Deficiency of choresteryl ester transfer protein and gene polymorphisms of lipoprotein lipase and hepatic lipase are not associated with longevity," J Mol Med (2003) 81:102-109.

Olivieri O et al., entitled "ApoC-III gene polymorphisms and risk of coronary artery disease," Journal of Lipid Research, vol. 43, 2002, 1450-1457.

Holmes M D et al., entitled "Lifestyle correlates of plasma insulin-like growth factor I and insulin-like growth factor binding protein 3 concentrations," Cancer Epidemiology Biomakers & Prevention, vol. 11, Sep. 2002, 862-867.

Lamarche B et al., entitled "The small dense LDL phenotype and the risk of cornary heart disease: Epidemiology, Path-Physiology and Therapeutic Aspects," Diabetes & Metabolism (Paris), vol. 25, 1999, 199-211.

* cited by examiner

A. Male

Probands

Offspring

Control

A

B

```
                         SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cagtcctcta cacagctgga ac                                              22

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
cggggtccag gctttcttgg                                                 20

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
agcggtgatc attgactgca ggaagctctg gc                                   32

<210> SEQ ID NO 4
<211> LENGTH: 21
```

-continued

```
<212> TYPE: DNA
<213> ORGANISM: Artificial Sequence
<220> FEATURE:
<223> OTHER INFORMATION: primer

<400> SEQUENCE: 4 tattttttc acggatgggc a                                              21

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
atcctataag gcacaggg                                                 18

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cttttataga ggtacatgtt c                                             21

<210> SEQ ID NO 7
<211> LENGTH: 16
<212> TYPE: DNA
<213> ORGANISM: Artificial Sequence
<220> FEATURE:
<223> OTHER INFORMATION: primer

<400> SEQUENCE: 7
gtattaagtg acagtg                                                   16
```

BIOLOGICAL MARKERS FOR LONGEVITY AND DISEASES AND USES THEREOF

CROSS-REFERENCE TO RELATED APPLICATIONS

This application is a continuation of U.S. patent application Ser. No. 11/229,327, filed Sep. 16, 2005, now U.S. Pat. No. 7,491,543, which is a continuation-in-part of and claims priority of PCT International Patent Application No. PCT/US2004/008876, filed Mar. 19, 2004, which designates the United States of America and which claims the benefit of U.S. Provisional Patent Application No. 60/456,304, filed Mar. 20, 2003, and of U.S. Provisional Patent Application No. 60/508,420, filed Oct. 3, 2003, the contents of all of which are hereby incorporated by reference in their entirety into the subject application.

STATEMENT OF GOVERNMENT SUPPORT

This invention was made with government support under grant numbers RO1-AG-18728-01A1, MO1-RR12248-05, and DK 20541 awarded by the National Institutes of Health, U.S. Department of Health and Human Services. The government has certain rights in the invention.

FIELD OF THE INVENTION

The present invention relates to uses of the sizes and levels of high-density lipoprotein (HDL) and low-density lipoprotein (LDL) particles, the 405 allele of the gene encoding cholesteryl ester transfer protein (CETP), the −641 allele of the promoter of the gene encoding apolipoprotein C-3 (APOC-3), and plasma levels of insulin-like growth factor-1 (IGF-1), adiponectin, CETP and APOC-3, for determining an individual's likelihood of longevity, of developing a cardiovascular related disease (e.g., hypertension, diabetes mellitus, myocardial infarction, stroke, and/or transient ischemic attack), a metabolic syndrome and/or an age-related disease, and of retaining cognitive function with aging.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

Subjects with exceptional longevity have generally been spared from major age-related diseases, such as cardiovascular disease, diabetes mellitus, Alzheimer's and cancer, which are responsible for most deaths in the elderly (1). Various studies suggest that while the effect of genetics on life expectancy is minimal across ages, this is not the case with centenarians (a rare phenotype achieved by ~1/10,000 individuals). Siblings of current centenarians have odds ratios of 8-17 of achieving 100 years of age, and parents of centenarians (born at ~1870) had odds ratio of ~7 of achieving ages 90-99 than an appropriate control (2-4). Furthermore, the offspring of long-lived parents had significantly lower prevalence (~50%) of hypertension, diabetes mellitus, myocardial infarctions and strokes/transient ischemic attacks compared with several age-matched control groups (4-5). In support of the inheritance of longevity, the New England Centenarian Study reported a statistically significant linkage between a genetic locus on chromosome 4 and exceptional longevity among siblings of centenarians (3).

Since lipid profile is directly correlated to cardiovascular disease, a favorable lipid profile may play a pivotal role in longevity. The complexity of such an assumption is depicted with the example of high-density lipoprotein (HDL) levels. The Framingham (8-9) and NHANES III (10) studies have shown that cross-sectional, plasma HDL levels were comparable at different age groups both in males and females. However, looking prospectively, plasma HDL levels seemed to decrease by over 5 mg/dl per decade. These seemingly contradictory results may be explained by HDL being a 'survival' factor. A decrease in HDL levels to below a certain range may result in the loss of cardiovascular protection (and possibly protection from other age-related diseases), hence in increased mortality. A study in healthy elderly and centenarians revealed a small but statistically significant reduction in the ratios of cholesterol/HDL-cholesterol and LDL-cholesterol/HDL-cholesterol, and a significant increase in HDL-cholesterol and apoA1 (11). Offspring of centenarians have significant higher plasma levels of HDL levels compared to controls (7). Lipoprotein (a) levels have been reported to be elevated in centenarians at the threshold for atherogenic risk (11-13). Favorable biological markers that are unchanged or decreased in centenarians do not rule out their role in longevity, and some of the harmful lipoprotein profile in centenarians are compatible with healthy longevity, suggesting that other characteristics may protect 'down stream' of these pathways.

The metabolic syndrome (MS) of aging/syndrome of insulin resistance is most commonly associated with obesity (115), but may be inherited in lean individuals. This syndrome is commonly associated with dyslipidemia, with decreased HDL cholesterol and increased LDL cholesterol levels, and with decreases in HDL and LDL particle sizes (116). However, it is unclear if increased HDL levels have a role in preventing this syndrome. This syndrome is also associated with hypertension, the development of type 2 diabetes mellitus (117), and a markedly increased risk of developing arteriosclerosis, and is therefore linked to decreased life expectancy (118, 119). Insulin resistance has been identified as a risk factor for a variety of cancers (120-122), broadening its link to shorter life span in humans and to most causes of death (123).

HDL (71) and LDL (22) constitute heterogeneous groups of particles which differ in characteristics such as density, size, electrophoretic mobility, and chemical content. Most of the HDL particles have a globular shape, containing unesterified cholesterol distributed between the surface and the core, and proteins are found in outer parts of the lipoproteins, mainly apoA1 but also apo A-II, A-IV, Cs, E, J, and sphingomyelins (79). Out of five subgroups of HDL, levels of $HDL_{2b}$ have been reported to be increased in a group of 16 centenarian women, while levels of $HDL_{3a}$ are reduced in comparison with controls (72); males were not included in this study. Levels of HDL2-C have been reported to be increased in people 65 years and older (74).

Low blood levels of HDL are strongly related with risk of atherosclerotic cardiovascular disease (57). Overexpression of the major HDL protein, apoA, markedly inhibits progression and even induces regression of atherosclerosis in animal models (40). Decreased plasma HDL level is also a risk for stroke and transient ischemic attack (TIA), but clinical data regarding the effect of increasing HDL cholesterol on vascular events are limited, because its rise is minor and secondary to drugs that lower LDL cholesterol (58, 59).

Amongst the many effects of plasma HDL, it recently became apparent that it may protect from decreased cognitive function associated with Alzheimer's (41) and other forms of dementia (42, 43). In a group of elderly (>85 years of age), the associations between low Mini Mental State Exam (MMSE) scores and low HDL was significant. This relationship was maintained even after subjects with cardiovascular disease or stroke were excluded, supporting the association between HDL and cognitive function independent of atherosclerotic disease (44). Because HDL (and not LDL) has effects that were not clearly limited to the vascular bed, it was recently hypothesized that the very old brain of centenarians, who are not characterized by Alzheimer's disease, may be protected by HDL (14). Indeed, each decrease in plasma HDL tertile was associated with a significant decrease in MMSE.

Previous studies have reported that abnormalities in the LDL receptor are associated with a decreased length of life (60, 61). However, LDL cholesterol has not been reported to change significantly with age in prospective or cross sectional studies (10, 57), although increased age is associated with higher plasma LDL cholesterol and apoB levels in postmenopausal women (57). Studies in healthy elderly and centenarians revealed a small but statistically significant and progressive reduction with age, in total cholesterol, triglycerides (TG) and LDL concentrations, as well as a significant increase in apolipoprotein B100 and lipoprotein (a) values (11-13). Male offspring of centenarians had significant lower plasma levels of LDL-cholesterol and higher levels of HDL-cholesterol compared to controls (7).

LDL particles contain unesterified cholesterol distributes between the surface and the core, and proteins are found in outer parts of the lipoproteins (mainly apoB LDL containing particles). The distribution of mass among LDL subclasses in plasma is reflected by the particle diameter and buoyant density of the predominant LDL species. A distinct LDL subclass pattern characterized by a predominance of small, dense LDL particles (previously called LDL3) has been identified (80). The prevalence of this trait increases with aging, and the prevalence of small particle size LDL (previously called subclass pattern B) is 3-4 fold increased in older compared with young men and women (29, 30). Evidence from several studies is consistent with an autosomal dominant or codominant model for inheritance of the pattern B phenotype with varying additive and polygenic effects (66, 81). One study has reported a predominance of large, buoyant LDL particles in 75% of centenarians and a predominance of small dense LDL particles in 25% of centenarians (73).

The association of plasma LDL cholesterol with a significant risk factor for a variety of cardiovascular diseases is well established (57). The oxidation of LDL is commonly considered to be a major event in the initiation and development of atherosclerosis (62). The plasma lipoprotein profile accompanying a predominance of small, dense LDL3 particles is associated with a 2-3 fold increased risk of coronary heart disease (30, 63-64). More recently, nested case-control analyses in prospective studies of population cohorts have demonstrated that reduced LDL particle size is a significant predictor for the development of coronary heart disease (21, 65-67).

One of the pathways that has been implicated in aging is the insulin/insulin-like growth factor (IGF-1) signaling pathway, which is involved in many functions that are necessary for metabolism, growth, and fertility in animal models as varied as flies, nematodes and mammals (147). Disruption of the insulin/IGF-1 receptor in nematodes and flies increases lifespan significantly, and several mammalian dwarf models live significantly longer, including Snell and Ames dwarf mice and heterozygous knockout mice for the IGF-1 receptor (132, 144). Low IGF-1 levels may protect humans from diseases like cancer (136-140), while normal or high IGF-1 levels may protect humans from osteoporosis (135), diabetes (143), and cardiovascular disease (134). Therefore, based on such data, an overall beneficial effect of changes in IGF-1 levels on human longevity remains uncertain.

Another factor that has been associated with disease process is adiponectin, a protein produced exclusively in adipose tissue, which occurs in serum in relatively high concentration. The plasma concentration of adiponectin is decreased in obese and in type 2 diabetic humans and in patients with coronary artery disease, and low adiponectin levels are a predictor of type 2 diabetes (reviewed in 145, 146). Many clinical reports and genetic studies over the past few years demonstrate decreased circulating levels of this hormone in metabolic dysfunction, such as obesity and insulin resistance, in both humans and animal models. Pharmacologic adiponectin treatments in rodents increase insulin sensitivity, mainly by its hepatic action. This protein also suppresses the expression of adhesion molecules in vascular endothelial cells and cytokine production from macrophages, thus inhibiting the inflammatory processes that occur during the early phases of atherosclerosis.

Cholesteryl ester transfer protein (CETP) is a plasma glycoprotein that catalyzes an exchange of cholesteryl esters (CE) and TG between HDL and APOB containing lipoproteins (70). The atherogenic properties of CETP have been demonstrated by blockade of CETP in cholesterol-fed rabbits, an animal with elevated CETP activity and high atherosclerosis susceptibility (82, 83). However, studies in CETP-deficient patients did not clarify whether CETP is atherogenic (84). CETP exerts a strong and direct effect on HDL size. Expression of CETP in normolipidemic rodents has a profound effect on large sized HDL, which was suggested as a reliable index of low plasma CETP activity in vivo (48, 85). In humans, plasma levels of large HDL particles from patients homo- and hetrozygous for CETP deficiency increased two- and six-fold while levels of small HDL remained unchanged (45, 46). The CETP 405 valine allele is associated with increased levels of HDL (55, 86). The presence of the B2 allele at the Taq1B polymorphism in intron 1 of the CETP gene has been associated with increased HDL particle size (106). Complete CETP deficiency causes a small-sized LDL population with low affinity for the LDL receptor (47). However, because an up-regulation of the LDL receptor increases LDL clearance, CETP deficiency is characterized by lowered LDL levels (49). Conflicting observations have been reported between CETP mutations and the incidence of coronary heart disease (CHD). Increased HDL cholesterol levels caused by mutations in CETP were associated with a slight increased risk of CHD in white Danish women (53). Similar observation of increase in CHD was observed in Japanese-American men with hetrozygous CETP D442G missense mutation (87), though their HDL levels were 10% increased. However, recently the Veterans Affairs HDL Cholesterol Intervention Trial reported that CETP Taq1 B2B2 genotype is associated with higher HDL cholesterol levels and lower risk of CHD in men (54).

Other genes are also involved in lipoprotein metabolism. Of particular interest is the gene encoding apolipoprotein C-3 (APOC-3). Transgenic APOC-3 mice are hypertriglyceridemic, and 'knock out' of this gene results in hypotriglyceridemic mice (124). APOC-3 is an effective inhibitor of very low-density lipoprotein (VLDL) TG hydrolysis, has a regulating role on uptake of cholesteryl esters, and may have a role as an inhibitor for lipoprotein lipase (LPL), although its exact role is not fully understood. Polymorphisms in APOC-3 have been associated with strong effects on triglyceride levels (125-127). The APOC-3 promoter region has conferred protection against or susceptibility to severe hypertriglyceridemic. The cysteine (C) allele of the Cysteine (−641)Alanine (A) polymorphism, the C allele of the C-482Threonine (T) polymorphism, and the T allele of T(-455)C polymorphism are protective against hypertriglyceridemia (128-129). Increased incidence of the C allele in the T-455C polymorphism was noted with advanced age, indicating that this variant promoter is associated with longevity (130). Furthermore, APOC-3 has effects on lipoprotein size through displacement of apolipoprotein E (APO-E) (131).

Despite the advances in knowledge discussed above, there remains a clear need for markers of longevity which may be used to decrease the risk of developing age-related diseases including dementia and metabolic- and cardiovascular-related diseases.

SUMMARY OF THE INVENTION

The present application is directed to the use of the sizes and levels of high-density lipoprotein (HDL) and low-density lipoprotein (LDL) particles, the 405 allele of a gene encoding cholesteryl ester transfer protein (CETP), the −641 allele of a promoter of the gene encoding apolipoprotein C-3 (APOC-3), and plasma levels of insulin-like growth factor-1 (IGF-1), adiponectin, CETP and APOC-3, for determining an individual's likelihood of longevity, of retaining cognitive function during aging, and of developing a cardiovascular-related disease, a metabolic syndrome or other age-related disease.

The invention provides a method of determining a subject's likelihood of longevity which comprises comparing high density lipoprotein (HDL) particle size from the subject's plasma with the high density lipoprotein (HDL) particle size from a control population, a larger size of the subject's high density lipoprotein (HDL) particles compared to the control population indicating that the subject has an increased likelihood of longevity. The invention also provides a method of determining an individual's likelihood of longevity which comprises comparing low density lipoprotein (LDL) particle size from the subject's plasma with low density lipoprotein (LDL) particle size from a control population, a larger size of the subject's low density lipoprotein (LDL) particles compared to the control population indicating that the subject has an increased likelihood of longevity. The invention further provides a method of determining a subject's likelihood of longevity which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has an increased likelihood of longevity.

The invention provides a method of determining a subject's likelihood of developing a cardiovascular related disease, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has a decreased likelihood of developing a cardiovascular related disease. The invention also provides method of determining a subject's likelihood of developing a cardiovascular related disease, which comprises comparing high density lipoprotein (HDL) particle size from the subject's plasma with high density lipoprotein (HDL) particle size from a control population, a smaller size of the subject's high density lipoprotein (HDL) particles compared to the control population indicating that the subject has an increased likelihood of developing a cardiovascular related disease.

The invention also provides a method of determining a subject's likelihood of developing a cardiovascular related disease, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has a decreased likelihood of developing a cardiovascular related disease. The invention further provides a method of determining a subject's likelihood of developing a cardiovascular related disease, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, smaller sizes of both the subject's high density lipoprotein (HDL) and low density lipoprotein (LDL) particles compared to the control population indicating that the subject has an increased likelihood of developing a cardiovascular related disease.

The invention provides a method of determining a subject's likelihood of retaining cognitive function during aging, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has an increased likelihood of retaining cognitive function during aging.

The invention provides a method of determining a subject's likelihood of developing a metabolic syndrome, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has a decreased likelihood of developing a metabolic syndrome. Also provided is a method of determining a subject's likelihood of developing a metabolic syndrome, which comprises comparing high density lipoprotein (HDL) particle size from the subject's plasma with high density lipoprotein (HDL) particle size from a control population, a smaller size of the subject's high density lipoprotein (HDL) particles compared to the control population indicating that the subject has an increased likelihood of developing a metabolic syndrome. The invention provides a method of determining a subject's likelihood of developing a metabolic syndrome, which comprises comparing low density lipoprotein (LDL) particle size from the subject's plasma with low density lipoprotein (LDL) particle size from a control population, a larger size of the subject's low density lipoprotein (LDL) particles compared to the control population indicating that the subject has a decreased likelihood of developing a metabolic syndrome. Also provided is a method of determining a subject's likelihood of developing a metabolic syndrome, which comprises comparing low density lipoprotein (LDL) particle size from the subject's plasma with low density lipoprotein (LDL) particle size from a control population, a smaller size of the subject's low density lipoprotein (LDL) particles compared to the control population indicating that the subject has an increased likelihood of developing a metabolic syndrome. The invention further provides a method of determining a subject's likelihood of developing a metabolic syndrome, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has a decreased likelihood of developing a metabolic syndrome. Also provided is method of determining a subject's likelihood of developing a metabolic syndrome, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, smaller sizes of both the subject's high density lipoprotein (HDL) and low density lipoprotein (LDL) particles compared to the control population indicating that the subject has an increased likelihood of developing a metabolic syndrome.

The invention provides a method of determining a subject's likelihood of longevity which comprises determining if the subject has a mutation in the gene encoding cholesteryl ester transfer protein (CETP) where the mutation results in decreased CETP activity, the presence of said mutation indicating that the subject has an increased likelihood of longevity. The invention further provides a method of determining a subject's likelihood of longevity which comprises determining if the subject is homozygous for a codon 405 valine allele of a gene encoding cholesteryl ester transfer protein, the presence of a homozygous valine/valine genotype indicating that the subject has an increased likelihood of longevity.

The invention provides a method of determining a subject's likelihood of retaining cognitive function during aging which comprises determining if the subject has a mutation in a gene encoding cholesteryl ester transfer protein (CETP) where the mutation results in decreased CETP activity, the presence of said mutation indicating that the subject has an increased likelihood of retaining cognitive function during aging. The invention further provides a method of determining a subject's likelihood of retaining cognitive function during aging which comprises determining if the subject is homozygous for a codon 405 valine allele of a gene encoding cholesteryl ester transfer protein, the presence of a homozygous valine/valine genotype indicating that the subject has an increased likelihood of retaining cognitive function during aging.

The invention provides a method of determining a subject's likelihood of developing a cardiovascular related disease, which comprises determining if the subject has a mutation in the gene encoding cholesteryl ester transfer protein (CETP) where the mutation results in decreased CETP activity, the presence of said mutation indicating that the subject has an decreased likelihood of developing a cardiovascular related disease. The invention further provides a method of determining a subject's likelihood of developing a cardiovascular related disease which comprises determining if the subject is homozygous for a codon 405 valine allele of a gene encoding cholesteryl ester transfer protein, the presence of a homozygous valine/valine genotype indicating that the subject has a decreased likelihood of developing a cardiovascular related disease.

The invention provides a method of determining a subject's likelihood of developing a metabolic syndrome, which comprises determining if the subject has a mutation in the gene encoding cholesteryl ester transfer protein (CETP) where the mutation results in decreased CETP activity, the presence of said mutation indicating that the subject has a decreased likelihood of developing a metabolic syndrome. The invention further provides a method of determining a subject's likelihood of developing a metabolic syndrome which comprises determining if the subject is homozygous for a codon 405 valine allele of a gene encoding cholesteryl ester transfer protein, the presence of a homozygous valine/valine genotype indicating that the subject has a decreased likelihood of developing a metabolic syndrome.

The invention provides a method of increasing a subject's likelihood of longevity which comprises increasing the size of high density lipoprotein (HDL) particles in the subject's plasma. The invention also provides a method of increasing a subject's likelihood of longevity which comprises increasing the size of low density lipoprotein (LDL) particles in the subject's plasma. The invention further provides a method of increasing a subject's likelihood of longevity which comprises increasing the sizes of both high density lipoprotein (HDL) and low density lipoprotein (LDL) particles in the subject's plasma.

The invention provides a method of decreasing a subject's likelihood of developing a cardiovascular related disease which comprises increasing the size of high density lipoprotein (HDL) particles in the subject's plasma. The invention also provides a method of decreasing a subject's likelihood of developing a cardiovascular related disease which comprises increasing the sizes of both high density lipoprotein (HDL) and low density lipoprotein (LDL) particles in the subject's plasma.

The invention provides a method of decreasing a subject's likelihood of developing a metabolic syndrome which comprises increasing the size of high density lipoprotein (HDL) particles or of low density lipoprotein (LDL) particles in the subject's plasma. The invention also provides a method of decreasing a subject's likelihood of developing a metabolic syndrome which comprises increasing the sizes of both high density lipoprotein (HDL) and low density lipoprotein (LDL) particles in the subject's plasma.

The invention provides a method of increasing a subject's likelihood of retaining cognitive function during aging which comprises increasing the size of high density lipoprotein (HDL) particles in the subject's plasma.

The invention provides methods of increasing a subject's likelihood of longevity, increasing a subject's likelihood of retaining cognitive function during aging, decreasing a subject's likelihood of developing a cardiovascular-related disease, decreasing a subject's likelihood of developing a metabolic syndrome, and decreasing a subject's likelihood of developing a disease which is characterized by a reduced size of high density lipoprotein (HDL) particles in the subject's plasma, which comprise inhibiting the activity of the subject's cholesteryl ester transfer protein (CETP).

The invention provides a method of determining a subject's likelihood of longevity, or of retaining cognitive function during aging, which comprises determining if the subject is homozygous for a codon −641 cysteine allele of a promoter of a gene encoding apolipoprotein C-3 (APOC-3), the presence of a homozygous cysteine/cysteine genotype indicating that the subject has an increased likelihood of longevity and/or of retaining cognitive function during aging. The invention also provides a method of determining a subject's likelihood of developing a cardiovascular related disease or a metabolic syndrome, which comprises determining if the subject is homozygous for a codon −641 cysteine allele of a promoter of a gene encoding apolipoprotein C-3 (APOC-3), the presence of a homozygous cysteine/cysteine genotype indicating that the subject has a decreased likelihood of developing a cardiovascular related disease and/or a metabolic syndrome.

The invention provides a method of determining a subject's likelihood of longevity or of retaining cognitive function during aging which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has an increased likelihood of longevity and/or of retaining cognitive function during aging. The invention also provides a method of determining a subject's likelihood of developing a cardiovascular related disease or a metabolic syndrome which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has a decreased likelihood of developing a cardiovascular related disease and/or a metabolic syndrome.

The invention provides methods of increasing a subject's likelihood of longevity and/or of retaining cognitive function during aging which comprise inhibiting the activity of the subject's apolipoprotein C-3 (APOC-3). The invention also provides methods of decreasing a subject's likelihood of developing a cardiovascular-related disease and/or a metabolic syndrome which comprise inhibiting the activity of the subject's apolipoprotein C-3 (APOC-3).

The invention provides a method of determining a subject's likelihood of longevity, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an increased likelihood of longevity. The invention also provides a method of determining a subject's likelihood of retaining cognitive function during aging, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an increased likelihood of retaining cognitive function during aging. The invention further provides a method of determining a subject's likelihood of developing a cardiovascular related disease, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an decreased likelihood of developing a cardiovascular related disease. The invention still further provides a method of determining a subject's likelihood of developing a metabolic syndrome, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an decreased likelihood of developing a metabolic syndrome.

The invention provides methods of increasing a subject's likelihood of longevity, increasing a subject's likelihood of retaining cognitive function during aging, and/or of decreasing a subject's likelihood of developing a cardiovascular-related disease, a metabolic syndrome, and/or an age-related disease, which comprise increasing the subject's plasma level of insulin-like growth factor-1 (IGF-1).

The invention provides a method of determining a subject's likelihood of longevity, which comprises comparing the subject's plasma level of adiponectin with the plasma level of adiponectin from a control population, a higher level of adiponectin in the subject's plasma than in plasma from the control population indicating that the subject has an increased likelihood of longevity. The invention also provides a method of determining a subject's likelihood of retaining cognitive function during aging, which comprises comparing the subject's plasma level of adiponectin with the plasma level of adiponectin from a control population, a higher level of adiponectin in the subject's plasma than in plasma from the control population indicating that the subject has an increased likelihood of retaining cognitive function during aging. The invention further provides a method of determining a subject's likelihood of developing a cardiovascular related disease, which comprises comparing the subject's plasma level of adiponectin with the plasma level of adiponectin from a control population, a higher level of adiponectin in the subject's plasma than in plasma from the control population indicating that the subject has an decreased likelihood of developing a cardiovascular related disease. The invention still further provides a method of determining a subject's likelihood of developing a metabolic syndrome, which comprises comparing the subject's plasma level of adiponectin with the plasma level of adiponectin from a control population, a higher level of adiponectin in the subject's plasma than in plasma from the control population indicating that the subject has an decreased likelihood of developing a metabolic syndrome.

The invention provides methods of increasing a subject's likelihood of longevity, increasing a subject's likelihood of retaining cognitive function during aging, and/or of decreasing a subject's likelihood of developing a cardiovascular-related disease, a metabolic syndrome, and/or an age-related disease, which comprise increasing the subject's plasma level of adiponectin.

The invention provides an assay for identifying a compound that increases a subject's likelihood of longevity, increases a subject's likelihood of retaining cognitive function during aging, decreases a subject's likelihood of developing a cardiovascular-related disease, decreases a subject's likelihood of developing a metabolic syndrome, and/or decreases a subject's likelihood of developing an age-related disease, which comprises identifying a compound which:
  (a) increases HDL particle size in the subject's plasma,
  (b) increases LDL particle size in the subject's plasma,
  (c) increases both HDL and LDL particle size in the subject's plasma,
  (d) increases the percentage of large size HDL particles in the subject's plasma,
  (e) increases the percentage of large size LDL particles in the subject's plasma,
  (f) increases the percentage of both large size HDL particles and large size LDL particles in the subject's plasma,
  (g) increases the subject's plasma level of HDL,
  (h) increases the subject's plasma level of insulin-like growth factor-1 (IGF-1),
  (i) increases the subject's plasma level of adiponectin,
  (j) inhibits the activity of the subject's cholesteryl ester transfer protein (CETP), and/or,
  (k) inhibits the activity of the subject's apolipoprotein C-3 (APOC-3).

BRIEF DESCRIPTION OF THE DRAWINGS

FIG. 1A, large HDL; FIG. 1B, small HDL; FIG. 1C, large LDL; FIG. 1D, small LDL. *Significant differences (p<0.001) between Probands and Offspring versus the two Control groups.

DETAILED DESCRIPTION OF THE INVENTION

Figure 1A:
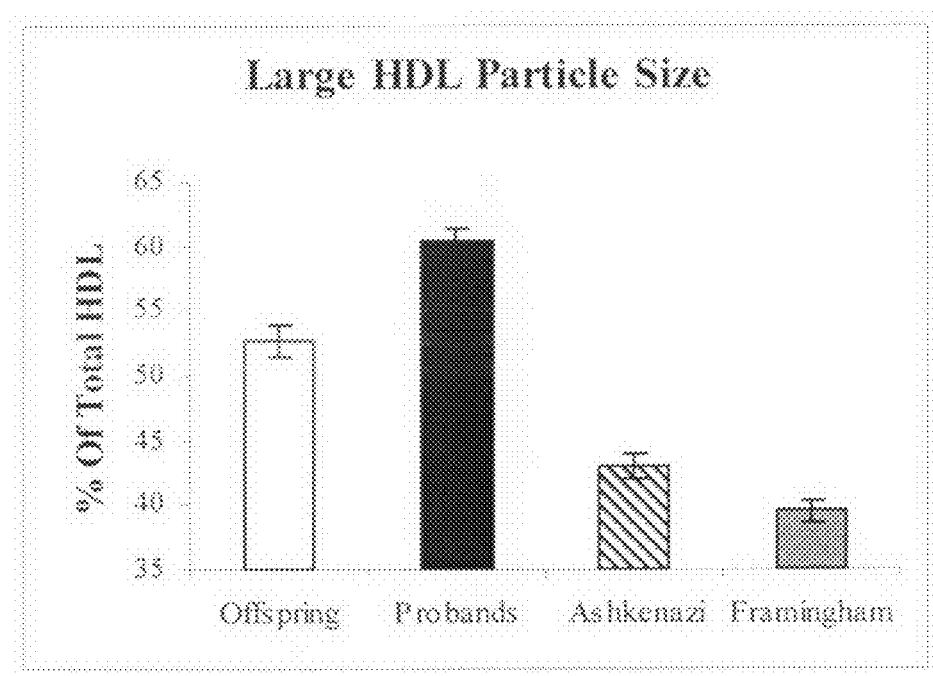
FIG. 1A-1D. Percentage of large and small HDL and LDL particles in Proband, Offspring, Ashkenazi Controls, and age-matched Framingham Controls.
Figure 1B:
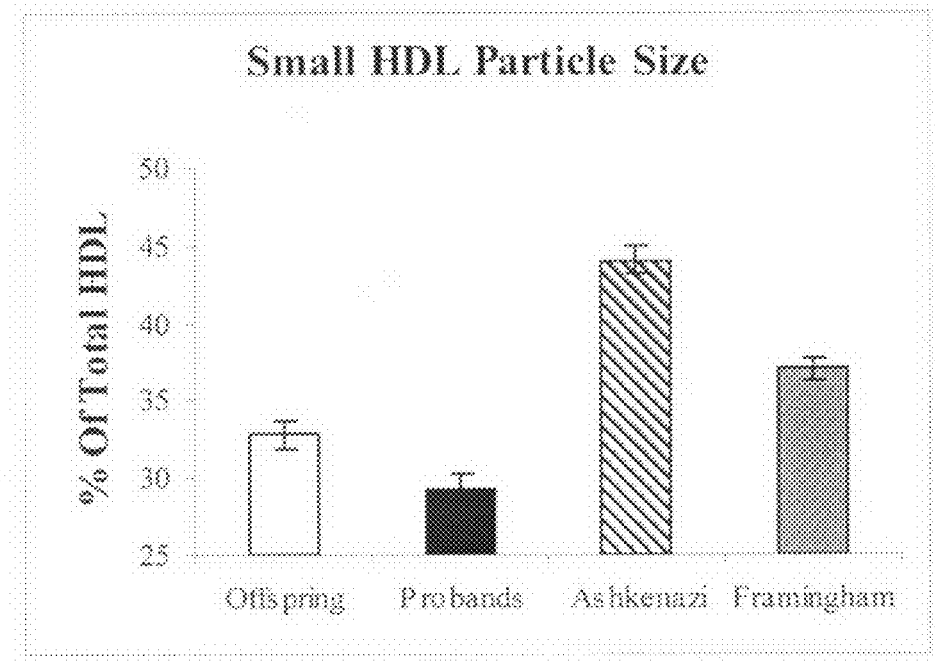
Figure 1C:
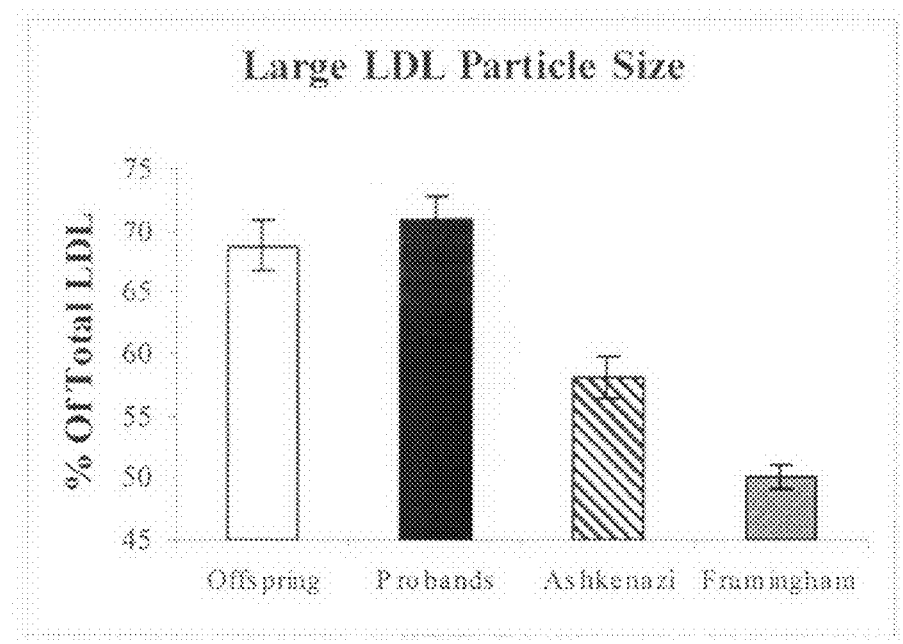
Figure 1D:
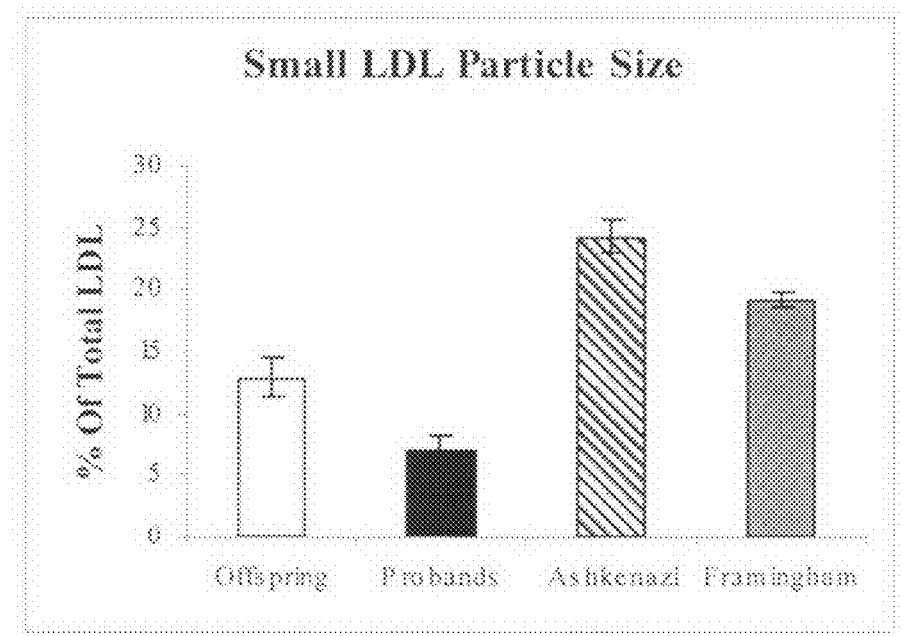

The subject invention is directed to a method of determining a subject's likelihood of longevity which comprises comparing high density lipoprotein (HDL) particle size from the subject's plasma with the high density lipoprotein (HDL) particle size from a control population, a larger size of the subject's high density lipoprotein (HDL) particles compared to the control population indicating that the subject has an increased likelihood of longevity. The invention also provides a method of determining an individual's likelihood of longevity which comprises comparing low density lipoprotein (LDL) particle size from the subject's plasma with low density lipoprotein (LDL) particle size from a control population, a larger size of the subject's low density lipoprotein (LDL) particles compared to the control population indicating that the subject has an increased likelihood of longevity. The invention further provides a method of determining a subject's likelihood of longevity which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has an increased likelihood of longevity.

One embodiment of the method further comprises comparing the number of large size HDL particles as a percentage of total HDL particles from the subject with the percentage of large size HDL particles from the control population, a larger percentage of large size HDL particles from the subject than from the control population indicating that the subject has an increased likelihood of longevity. A further embodiment comprises comparing the number of medium size HDL particles as a percentage of total HDL particles from the subject with the percentage of medium size HDL particles from the control population, a smaller percentage of medium size HDL particles from the subject than from the control population indicating that the subject has an increased likelihood of longevity. One embodiment comprises comparing the number of large size LDL particles as a percentage of total LDL particles from the subject with the percentage of large size LDL particles from the control population, a larger percentage of large size LDL particles from the subject than from the control population indicating that the subject has an increased likelihood of longevity. A further embodiment comprises comparing the number of small size LDL particles as a percentage of total LDL particles from the subject with the percentage of small size LDL particles from the control population, a smaller percentage of small size LDL particles from the subject than from the control population indicating that the subject has an increased likelihood of longevity.

In different embodiments of the method, the average size of the subject's high density lipoprotein (HDL) particles can be at least 2%, 3% or 4% greater than the average size of the high density lipoprotein (HDL) particles from a control population of the same gender as the subject. The average size of the subject's low density lipoprotein (LDL) particles can be at least 2% or 3% greater than the average size of the low density lipoprotein (LDL) particles from a control population of the same gender as the subject.

In different embodiments, the average size of the subject's high density lipoprotein (HDL) particles can be at least 0.2 nm, 0.3 nm or 0.4 nm larger in diameter than the average size of the high density lipoprotein (HDL) particles from a control population of the same gender as the subject. The average size of the subject's low density lipoprotein (LDL) particles can be at least 0.4 nm, 0.5 nm or 0.6 nm larger in diameter than the average size of the low density lipoprotein (LDL) particles from a control population of the same gender as the subject.

HDL and LDL particle size can be determined by a number of methods including nuclear magnetic resonance spectroscopy, gel electrophoresis, and electron microscopy measurement.

The invention provides a method of determining a subject's likelihood of longevity which comprises determining if the subject has a mutation in the gene encoding cholesteryl ester transfer protein (CETP) where the mutation results in decreased CETP activity, the presence of said mutation indicating that the subject has an increased likelihood of longevity. As used herein, "decreased CETP activity" includes decreased levels of CETP and/or decreased activity of the protein itself. The CETP gene is known to be highly polymorphic, and many mutations have been described in its coding and non-coding regions (86, 102-108). The presence of the B2 allele at the Taq1B polymorphism in intron 1 of the CETP gene has been reported to be associated with reduced CETP levels (103-106) and activity (107). A more recent study concluded that Taq1B polymorphism is not instrumental in determining CETP levels, but is a marker for a promoter variant of the CETP gene at position −629 relative to the transcription start, and furthermore that the −2708 and −971 polymorphisms are likely to play a role in determining CETP concentration (102). In one embodiment, the invention provides a method of determining a subject's likelihood of longevity which comprises determining if the subject is homozygous for a codon 405 valine allele of a gene encoding cholesteryl ester transfer protein, the presence of a homozygous valine/valine genotype indicating that the subject has an increased likelihood of longevity. The incidence of the homozygous allele can be increased about 2-3 fold in a subject with longevity compared to a control population.

The subject can be a mammalian subject or a human subject. A human subject with longevity can live to be at least 95 years of age. A subject with longevity can also be considered to be a subject in whom aging is delayed.

The invention provides a method of determining a subject's likelihood of developing a cardiovascular related disease, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has a decreased likelihood of developing a cardiovascular related disease. The invention also provides a method of determining a subject's likelihood of developing a cardiovascular related disease, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has a decreased likelihood of developing a cardiovascular related disease. One embodiment of the method further comprises comparing the number of large size HDL particles as a percentage of total HDL particles from the subject with the percentage of large size HDL particles from the control population, a larger percentage of large size HDL particles from the subject than from the control population indicating that the subject has a decreased likelihood of developing a cardiovascular related disease.

In one embodiment, the average size of the subject's high density lipoprotein (HDL) particles can be at least 2% larger than the average size of the high density lipoprotein (HDL) particles from a control population of the same gender as the subject. The average size of the subject's high density lipoprotein (HDL) particles can be at least 0.2 nm larger in diameter than the average size of the high density lipoprotein (HDL) particles from a control population of the same gender as the subject. The average size of the subject's low density lipoprotein (LDL) particles can be at least 0.3 nm larger in diameter than the average size of the low density lipoprotein (LDL) particles from a control population of the same gender as the subject.

The invention also provides method of determining a subject's likelihood of developing a cardiovascular related disease, which comprises comparing high density lipoprotein (HDL) particle size from the subject's plasma with high density lipoprotein (HDL) particle size from a control population, a smaller size of the subject's high density lipoprotein (HDL) particles compared to the control population indicating that the subject has an increased likelihood of developing a cardiovascular related disease. The invention further provides a method of determining a subject's likelihood of developing a cardiovascular related disease, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, smaller sizes of both the subject's high density lipoprotein (HDL) and low density lipoprotein (LDL) particles compared to the control population indicating that the subject has an increased likelihood of developing a cardiovascular related disease. One embodiment of the method further comprises comparing the number of large size HDL particles as a percentage of total HDL particles from the subject with the percentage of large size HDL particles from the control population, a smaller percentage of large size HDL particles from the subject than from the control population indicating that the subject has an increased likelihood of developing a cardiovascular related disease.

In one embodiment, the average size of the subject's high density lipoprotein (HDL) particles is at least 2% smaller than the average size of the high density lipoprotein (HDL) particles from a control population of the same gender as the subject. The average size of the subject's high density lipoprotein (HDL) particles can be at least 0.2 nm smaller in diameter than the average size of the high density lipoprotein (HDL) particles from a control population of the same gender as the subject. The average size of the subject's low density lipoprotein (LDL) particles can be at least 0.3 nm smaller in diameter than the average size of the low density lipoprotein (LDL) particles from a control population of the same gender as the subject.

A subject is defined as having a "metabolic syndrome" according to the guidelines of the National Cholesterol Education Program (NCEP), Adult Treatment Panel III (ATP III) (113), if the subject has three or more of the following five risk factors: 1) increased waist girth (>94 cm for women, >102 cm for men), 2) increased blood pressure (>130//85 or treatment for hypertension), 3) increased fasting glucose (>110 mg/dl or drug treatment for diabetes), 4) low plasma HDL cholesterol (<40 mg/dl), and 5) elevated fasting triglyceride levels (>150 mg/dl). In one embodiment of the methods described herein, the subject is defined as having a metabolic syndrome if the subject has three or more of the following four risk factors: 1) increased waist girth (>94 cm for women, >102 cm for men), 2) increased blood pressure (>130//85 or treatment for hypertension), 3) increased fasting glucose (>110 mg/dl or drug treatment for diabetes), and 4) elevated fasting triglyceride levels (>150 mg/dl).

The invention provides a method of determining a subject's likelihood of developing a metabolic syndrome, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has a decreased likelihood of developing a metabolic syndrome. The invention also provides a method of determining a subject's likelihood of developing a metabolic syndrome, which comprises comparing low density lipoprotein (LDL) particle size from the subject's plasma with low density lipoprotein (LDL) particle size from a control population, a larger size of the subject's low density lipoprotein (LDL) particles compared to the control population indicating that the subject has a decreased likelihood of developing a metabolic syndrome. The invention further provides a method of determining a subject's likelihood of developing a metabolic syndrome, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, larger sizes of both the subject's high density lipoprotein (HDL) and low density lipoprotein (LDL) particles compared to the control population indicating that the subject has a decreased likelihood of developing a metabolic syndrome. One embodiment of the methods further comprises comparing the number of large size HDL particles as a percentage of total HDL particles from the subject with the percentage of large size HDL particles from the control population, a larger percentage of large size HDL particles from the subject than from the control population indicating that the subject has a decreased likelihood of developing a metabolic syndrome. One embodiment further comprises comparing the number of large size LDL particles as a percentage of total LDL particles from the subject with the percentage of large size LDL particles from the control population, a larger percentage of large size LDL particles from the subject than from the control population indicating that the subject has a decreased likelihood of developing a metabolic syndrome.

In one embodiment, the average size of the subject's high density lipoprotein (HDL) particles is at least 3% greater than the average size of the high density lipoprotein (HDL) particles from the control population. In another embodiment, the average size of the subject's high density lipoprotein (HDL) particles is at least 4% greater than the average size of the high density lipoprotein (HDL) particles from the control population. In one embodiment, the average size of the subject's low density lipoprotein (LDL) particles is at least 2% greater than the average size of the low density lipoprotein (LDL) particles from the control population.

In one embodiment, the average size of the subject's high density lipoprotein (HDL) particles is at least 0.3 nm larger in diameter than the average size of the high density lipoprotein (HDL) particles from the control population. In another embodiment, the average size of the subject's high density lipoprotein (HDL) particles is at least 0.4 nm larger in diameter than the average size of the high density lipoprotein (HDL) particles from the control population. In one embodiment, the average size of the subject's low density lipoprotein (LDL) particles is at least 0.3 nm larger in diameter than the average size of the low density lipoprotein (LDL) particles from the control population. In another embodiment, the average size of the subject's low density lipoprotein (LDL) particles is at least 0.5 nm larger in diameter than the average size of the low density lipoprotein (LDL) particles from the control population.

The invention provides a method of determining a subject's likelihood of developing a metabolic syndrome, which comprises comparing high density lipoprotein (HDL) particle size from the subject's plasma with high density lipoprotein (HDL) particle size from a control population, a smaller size of the subject's high density lipoprotein (HDL) particles compared to the control population indicating that the subject has an increased likelihood of developing a metabolic syndrome. The invention also provides a method of determining a subject's likelihood of developing a metabolic syndrome, which comprises comparing low density lipoprotein (LDL) particle size from the subject's plasma with low density lipoprotein (LDL) particle size from a control population, a smaller size of the subject's low density lipoprotein (LDL) particles compared to the control population indicating that the subject has an increased likelihood of developing a metabolic syndrome. The invention further provides a method of determining a subject's likelihood of developing a metabolic syndrome, which comprises comparing sizes of both high density lipoprotein (HDL) and low density lipoprotein (LDL) particles from the subject's plasma with the sizes of both high density lipoprotein (HDL) and low density lipoprotein (LDL) particles from a control population, smaller sizes of both the subject's high density lipoprotein (HDL) and low density lipoprotein (LDL) particles compared to the control population indicating that the subject has an increased likelihood of developing a metabolic syndrome. One embodiment of the methods further comprises comparing the number of large size HDL particles as a percentage of total HDL particles from the subject with the percentage of large size HDL particles from the control population, a smaller percentage of large size HDL particles from the subject than from the control population indicating that the subject has an increased likelihood of developing a metabolic syndrome. One embodiment further comprises comparing the number of large size LDL particles as a percentage of total LDL particles from the subject with the percentage of large size LDL particles from the control population, a smaller percentage of large size LDL particles from the subject than from the control population indicating that the subject has an increased likelihood of developing a metabolic syndrome.

In one embodiment, the average size of the subject's high density lipoprotein (HDL) particles is at least 3% smaller than the average size of the high density lipoprotein (HDL) particles from the control population. In another embodiment, the average size of the subject's high density lipoprotein (HDL) particles is at least 4% smaller than the average size of the high density lipoprotein (HDL) particles from the control population. In one embodiment, the average size of the subject's low density lipoprotein (LDL) particles is at least 2% smaller than the average size of the low density lipoprotein (LDL) particles from the control population.

In one embodiment, the average size of the subject's high density lipoprotein (HDL) particles is at least 0.3 nm smaller in diameter than the average size of the high density lipoprotein (HDL) particles from the control population. In another embodiment, the average size of the subject's high density lipoprotein (HDL) particles is at least 0.4 nm smaller in diameter than the average size of the high density lipoprotein (HDL) particles from the control population. In one embodiment, the average size of the subject's low density lipoprotein (LDL) particles is at least 0.3 nm smaller in diameter than the average size of the low density lipoprotein (LDL) particles from the control population. In another embodiment, the average size of the subject's low density lipoprotein (LDL) particles is at least 0.5 nm smaller in diameter than the average size of the low density lipoprotein (LDL) particles from the control population.

The invention provides a method of determining a subject's likelihood of retaining cognitive function during aging, which comprises comparing high density lipoprotein (HDL) particle size from the subject's plasma with high density lipoprotein (HDL) particle size from a control population, a larger size of the subject's high density lipoprotein (HDL) particles compared to the control population indicating that the subject has an increased likelihood of retaining cognitive function during aging. One embodiment of the method further comprises comparing the number of large size HDL particles as a percentage of total HDL particles from the subject with the percentage of large size HDL particles from the control population, a larger percentage of large size HDL particles from the subject than from the control population indicating that the subject has an increased likelihood of retaining cognitive function during aging.

In one embodiment of the method, the average size of the subject's high density lipoprotein (HDL) particles can at least 2% larger than the average size of the high density lipoprotein (HDL) particles from a control population of the same gender as the subject. The average size of the subject's high density lipoprotein (HDL) particles can be at least 0.2 nm larger in diameter than the average size of the high density lipoprotein (HDL) particles from a control population of the same gender as the subject.

The invention provides a method of determining a subject's likelihood of retaining cognitive function during aging which comprises determining if the subject has a mutation in a gene encoding cholesteryl ester transfer protein (CETP) where the mutation results in decreased CETP activity, the presence of said mutation indicating that the subject has an increased likelihood of retaining cognitive function during aging. The invention further provides a method of determining a subject's likelihood of retaining cognitive function during aging which comprises determining if the subject is homozygous for a codon 405 valine allele of a gene encoding cholesteryl ester transfer protein, the presence of a homozygous valine/valine genotype indicating that the subject has an increased likelihood of retaining cognitive function during aging.

The invention provides a method of increasing a subject's likelihood of longevity which comprises increasing the size of high density lipoprotein (HDL) particles in the subject's plasma. The invention also provides a method of increasing a subject's likelihood of longevity which comprises increasing the size of low density lipoprotein (LDL) particles in the subject's plasma. The invention further provides a method of increasing a subject's likelihood of longevity which comprises increasing the sizes of both high density lipoprotein (HDL) and low density lipoprotein (LDL) particles in the subject's plasma. One embodiment of the method further comprises increasing the number of large size HDL particles as a percentage of total HDL particles. One embodiment further comprises decreasing the number of medium size HDL particles as a percentage of total HDL particles. One embodiment further comprises increasing the number of large size LDL particles as a percentage of total LDL particles. One embodiment further comprises decreasing the number of small size LDL particles as a percentage of total LDL particles.

The invention provides a method of decreasing a subject's likelihood of developing a cardiovascular related disease which comprises increasing the size of high density lipoprotein (HDL) particles in the subject's plasma. The invention also provides a method of decreasing a subject's likelihood of developing a cardiovascular related disease which comprises increasing the sizes of both high density lipoprotein (HDL) and low density lipoprotein (LDL) particles in the subject's plasma.

The invention provides a method of increasing a subject's likelihood of retaining cognitive function during aging which comprises increasing the size of high density lipoprotein (HDL) particles in the subject's plasma.

The invention provides a method of decreasing a subject's likelihood of developing a metabolic syndrome which comprises increasing the size of high density lipoprotein (HDL) particles in the subject's plasma. The invention also provides a method of decreasing a subject's likelihood of developing a metabolic syndrome which comprises increasing the size of low density lipoprotein (LDL) particles in the subject's plasma. The invention further provides a method of decreasing a subject's likelihood of developing a metabolic syndrome which comprises increasing the sizes of both high density lipoprotein (HDL) and low density lipoprotein (LDL) particles in the subject's plasma.

One embodiment of the methods further comprises increasing the number of large size HDL particles as a percentage of total HDL particles. One embodiment comprises increasing the number of large size LDL particles as a percentage of total LDL particles.

Several methods are known for increasing the sizes of high density lipoprotein (HDL) and low density lipoprotein (LDL) particles. For example, HDL and LDL particle size can be increased by exercise (20). Increased HDL sub-fractions with exercise training seemed dependent on CETP genotype (56). HDL particle size and the concentration of large HDL particles can be increased by administering a combination of estradiol and medroxyprogesterone (68). LDL particle size can be increased by some lipid lowering drugs, e.g. fenofibrate and atorvastatin (69).

The invention provides a method of increasing a subject's likelihood of longevity which comprises inhibiting the activity of the subject's cholesteryl ester transfer protein (CETP). The invention also provides a method of increasing a subject's likelihood of retaining cognitive function during aging which comprises inhibiting the activity of the subject's cholesteryl ester transfer protein (CETP). The invention further provides a method of decreasing a subject's likelihood of developing a cardiovascular-related disease which comprises inhibiting the activity of the subject's cholesteryl ester transfer protein (CETP). The cardiovascular-related disease can be any one or more of, for example, hypertension, diabetes mellitus, myocardial infarction, stroke and transient ischemic attack. In one embodiment, the cardiovascular-related disease is characterized by a reduced size of high density lipoprotein (HDL) particles in the subject's plasma. The invention provides a method of decreasing a subject's likelihood of developing a metabolic syndrome which comprises inhibiting the activity of the subject's cholesteryl ester transfer protein (CETP). The invention further provides a method of decreasing a subject's likelihood of developing a disease which is characterized by a reduced size of high density lipoprotein (HDL) particles in the subject's plasma which comprises inhibiting the activity of the subject's cholesteryl ester transfer protein (CETP). The disease may be a cardiovascular-related disease.

The activity of cholesteryl ester transfer protein (CETP) can be inhibited by manipulations at any one or more of the levels of the protein itself, the protein target, or nucleic acids that encode the protein, and/or by decreasing the plasma level of CETP. Human CETP and nucleic acid encoding it have been described (89-91, 101-102). Possible methods of inhibiting CETP include use of antisense oligonucleotides, RNA aptamers (96), RNA interference (97), and antibodies to CETP (e.g., 98-100). In addition, inhibitors to CETP and methods of making them have been described (92-94). Also, a method has been described for eliciting an immune response against CETP activity (95).

The invention provides a method of determining a subject's likelihood of longevity, which comprises comparing the subject's plasma level of cholesteryl ester transfer protein (CETP) with the plasma level of cholesteryl ester transfer protein (CETP) from a control population, a lower level of cholesteryl ester transfer protein (CETP) in the subject's plasma than in plasma from the control population indicating that the subject has an increased likelihood of longevity. The invention also provides a method of determining a subject's likelihood of retaining cognitive function during aging, which comprises comparing the subject's plasma level of cholesteryl ester transfer protein (CETP) with the plasma level of cholesteryl ester transfer protein (CETP) from a control population, a lower level of cholesteryl ester transfer protein (CETP) in the subject's plasma than in plasma from the control population indicating that the subject has an increased likelihood of retaining cognitive function during aging. The invention further provides a method of determining a subject's likelihood of developing a cardiovascular related disease, which comprises comparing the subject's plasma level of cholesteryl ester transfer protein (CETP) with the plasma level of cholesteryl ester transfer protein (CETP) from a control population, a lower level of cholesteryl ester transfer protein (CETP) in the subject's plasma than in plasma from the control population indicating that the subject has a decreased likelihood of developing a cardiovascular related disease. In one embodiment, the cardiovascular-related disease is characterized by a reduced size of high density lipoprotein (HDL) particles in the subject's plasma. The invention still further provides a method of determining a subject's likelihood of developing a metabolic syndrome, which comprises comparing the subject's plasma level of cholesteryl ester transfer protein (CETP) with the plasma level of cholesteryl ester transfer protein (CETP) from a control population, a lower level of cholesteryl ester transfer protein (CETP) in the subject's plasma than in plasma from the control population indicating that the subject has a decreased likelihood of developing a metabolic syndrome.

The invention provides a method of determining a subject's likelihood of developing a cardiovascular related disease, which comprises determining if the subject is homozygous for a codon 405 valine allele of a gene encoding cholesteryl ester transfer protein (CETP), the presence of a homozygous valine/valine genotype indicating that the subject has a decreased likelihood of developing a cardiovascular related disease. In one embodiment, the cardiovascular-related disease is characterized by a reduced size of high density lipoprotein (HDL) particles in the subject's plasma. The invention also provides a method of determining a subject's likelihood of developing a metabolic syndrome which comprises determining if the subject is homozygous for a codon 405 valine allele of a gene encoding cholesteryl ester transfer protein (CETP), the presence of a homozygous valine/valine genotype indicating that the subject has a decreased likelihood of developing a metabolic syndrome.

The invention provides a method of determining a subject's likelihood of developing a cardiovascular related disease, which comprises determining if the subject has a mutation in the gene encoding cholesteryl ester transfer protein (CETP) where the mutation results in decreased CETP activity, the presence of said mutation indicating that the subject has a decreased likelihood of developing a cardiovascular related disease. In one embodiment, the cardiovascular-related disease is characterized by a reduced size of high density lipoprotein (HDL) particles in the subject's plasma. The invention also provides a method of determining a subject's likelihood of developing a metabolic syndrome, which comprises determining if the subject has a mutation in the gene encoding cholesteryl ester transfer protein (CETP) where the mutation results in decreased CETP activity, the presence of said mutation indicating that the subject has a decreased likelihood of developing a metabolic syndrome.

The invention provides a method of determining a subject's likelihood of longevity which comprises determining if the subject is homozygous for a codon −641 cysteine allele of a promoter of a gene encoding apolipoprotein C-3 (APOC-3), the presence of a homozygous cysteine/cysteine genotype indicating that the subject has an increased likelihood of longevity. The invention also provides a method of determining a subject's likelihood of retaining cognitive function during aging which comprises determining if the subject is homozygous for a codon −641 cysteine allele of a promoter of a gene encoding apolipoprotein C-3 (APOC-3), the presence of a homozygous cysteine/cysteine genotype indicating that the subject has an increased likelihood of retaining cognitive function during aging. The invention further provides a method of determining a subject's likelihood of developing a cardiovascular related disease, which comprises determining if the subject is homozygous for a codon −641 cysteine allele of a promoter of a gene encoding apolipoprotein C-3 (APOC-3), the presence of a homozygous cysteine/cysteine genotype indicating that the subject has a decreased likelihood of developing a cardiovascular related disease. The invention still further provides method of determining a subject's likelihood of developing a metabolic syndrome which comprises determining if the subject is homozygous for a codon −641 cysteine allele of a promoter of a gene encoding apolipoprotein C-3 (APOC-3), the presence of a homozygous cysteine/cysteine genotype indicating that the subject has a decreased likelihood of developing a metabolic syndrome.

The invention provides a method of determining a subject's likelihood of longevity which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has an increased likelihood of longevity. The invention also provides a method of determining a subject's likelihood of retaining cognitive function during aging which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has an increased likelihood of retaining cognitive function during aging. The invention further provides a method of determining a subject's likelihood of developing a cardiovascular related disease which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has a decreased likelihood of developing a cardiovascular related disease. The invention still further provides a method of determining a subject's likelihood of developing a metabolic syndrome which comprises determining if the subject has a mutation in a gene encoding apolipoprotein C-3 (APOC-3), or a mutation in a promoter of a gene encoding apolipoprotein C-3 (APOC-3), where the mutation results in decreased APOC-3 activity, the presence of said mutation indicating that the subject has a decreased likelihood of developing a metabolic syndrome. In one embodiment, the mutation is in a gene encoding apolipoprotein C-3 (APOC-3). In one embodiment, the mutation is in a promoter of a gene encoding apolipoprotein C-3 (APOC-3).

The invention provides a method of increasing a subject's likelihood of longevity which comprises inhibiting the activity of the subject's apolipoprotein C-3 (APOC-3). The invention also provides a method of increasing a subject's likelihood of retaining cognitive function during aging which comprises inhibiting the activity of the subject's apolipoprotein C-3 (APOC-3). The invention further provides a method of decreasing a subject's likelihood of developing a cardiovascular-related disease which comprises inhibiting the activity of the subject's apolipoprotein C-3 (APOC-3). The invention still further provides a method of decreasing a subject's likelihood of developing a metabolic syndrome which comprises inhibiting the activity of the subject's apolipoprotein C-3 (APOC-3). The activity of apolipoprotein C-3 (APOC-3) can be inhibited by manipulations at any one or more of the levels of the protein itself, the protein target, or nucleic acids that encode the protein, and/or by decreasing the plasma level of apolipoprotein C-3 (APOC-3). Mammalian apolipoprotein C-3 (APOC-3) and nucleic acid encoding it have been described (150). Possible methods of inhibiting apolipoprotein C-3 (APOC-3) include use of antisense oligonucleotides, RNA aptamers (96), RNA interference (97), and antibodies to apolipoprotein C-3 (APOC-3).

The invention provides a method of determining a subject's likelihood of longevity, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an increased likelihood of longevity. The invention also provides a method of determining a subject's likelihood of retaining cognitive function during aging, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an increased likelihood of retaining cognitive function during aging. The invention further provides a method of determining a subject's likelihood of developing a cardiovascular related disease, which comprises comparing the subject's plasma level of insulin-like growth factor-1 (IGF-1) with the plasma level of insulin-like growth factor 1(IGF-1) from a control population, a higher level of insulin-like growth factor-1 (IGF-1) in the subject's plasma than in plasma from the control population indicating that the subject has an decreased likelihood of developing a cardiovascular related disease. The invention still further provides a method of determining a subject's likelihood of developing a metabolic syndrome, which comprises comparing the subject's plasma level of insulin-like growth factor-1 (IGF-1) with the plasma level of insulin-like growth factor-1 (IGF-1) from a control population, a higher level of insulin-like growth factor-1 (IGF-1) in the subject's plasma than in plasma from the control population indicating that the subject has an decreased likelihood of developing a metabolic syndrome.

The invention provides a method of increasing a subject's likelihood of longevity, which comprises increasing the subject's plasma level of insulin-like growth factor-1 (IGF-1). The invention also provides a method of increasing a subject's likelihood of retaining cognitive function during aging, which comprises increasing the subject's plasma level of insulin-like growth factor-1 (IGF-1). The invention further provides a method of decreasing a subject's likelihood of developing a cardiovascular related disease, which comprises increasing the subject's plasma level of insulin-like growth factor-1 (IGF-1). The invention still further provides a method of decreasing a subject's likelihood of developing a metabolic syndrome, which comprises increasing the subject's plasma level of insulin-like growth factor-1 (IGF-1). IGF-1 plasma levels could be increased by giving a subject IGF-1 or by giving a substance that increases the synthesis or release of IGF-1. IGF-1 is commercially available.

The invention provides a method of determining a subject's likelihood of longevity, which comprises comparing the subject's plasma level of adiponectin with the plasma level of adiponectin from a control population, a higher level of adiponectin in the subject's plasma than in plasma from the control population indicating that the subject has an increased likelihood of longevity. The invention also provides a method of determining a subject's likelihood of retaining cognitive function during aging, which comprises comparing the subject's plasma level of adiponectin with the plasma-level of adiponectin from a control population, a higher level of adiponectin in the subject's plasma than in plasma from the control population indicating that the subject has an increased likelihood of retaining cognitive function during aging. The invention further provides a method of determining a subject's likelihood of developing a cardiovascular related disease, which comprises comparing the subject's plasma level of adiponectin with the plasma level of adiponectin from a control population, a higher level of adiponectin in the subject's plasma than in plasma from the control population indicating that the subject has an decreased likelihood of developing a cardiovascular related disease. The invention still further provides a method of determining a subject's likelihood of developing a metabolic syndrome, which comprises comparing the subject's plasma level of adiponectin with the plasma level of adiponectin from a control population, a higher level of adiponectin in the subject's plasma than in plasma from the control population indicating that the subject has an decreased likelihood of developing a metabolic syndrome.

The invention provides a method of increasing a subject's likelihood of longevity, which comprises increasing the subject's plasma level of adiponectin. The invention also provides a method of increasing a subject's likelihood of retaining cognitive function during aging, which comprises increasing the subject's plasma level of adiponectin. The invention further provides a method of decreasing a subject's likelihood of developing a cardiovascular related disease, which comprises increasing the subject's plasma level of adiponectin. The invention still further provides a method of decreasing a subject's likelihood of developing a metabolic syndrome, which comprises increasing the subject's plasma level of adiponectin. Adiponectin is also known as Acrp30 and AdipoQ. The amino acid and DNA sequences for human Acrp30 have been described (151).

The invention provides an assay for identifying a compound that increases a subject's likelihood of longevity, increases a subject's likelihood of retaining cognitive function during aging, decreases a subject's likelihood of developing a cardiovascular-related disease, decreases a subject's likelihood of developing a metabolic syndrome, and/or decreases a subject's likelihood of developing an age-related disease, which comprises identifying a compound which:

(a) increases HDL particle size in the subject's plasma,
(b) increases LDL particle size in the subject's plasma,
(c) increases both HDL and LDL particle size in the subject's plasma,
(d) increases the percentage of large size HDL particles in the subject's plasma,
(e) increases the percentage of large size LDL particles in the subject's plasma,
(f) increases the percentage of both large size HDL particles and large size LDL particles in the subject's plasma,
(g) increases the subject's plasma level of HDL,
(h) increases the subject's plasma level of insulin-like growth factor-1 (IGF-1),
(i) increases the subject's plasma level of adiponectin,
(j) inhibits the activity of the subject's cholesteryl ester transfer protein (CETP), and/or,
(k) inhibits the activity of the subject's apolipoprotein C-3 (APOC-3).

In one embodiment of the assay, the compound increases a subject's likelihood of longevity. In one embodiment, the compound increases a subject's likelihood of retaining cognitive function during aging. In one embodiment, the compound decreases a subject's likelihood of developing a cardiovascular-related disease. In one embodiment, the compound decreases a subject's likelihood of developing a metabolic syndrome. In one embodiment, the compound decreases a subject's likelihood of developing an age-related disease. In one embodiment, the compound increases HDL particle size in the subject's plasma. In one embodiment, the compound increases LDL particle size in the subject's plasma. In one embodiment, compound increases both HDL and LDL particle size in the subject's plasma. In one embodiment, the compound increases the percentage of large size HDL particles in the subject's plasma. Large HDL particles range in size from 8.8-13 nm. In one embodiment, the compound increases the percentage of large size LDL particles in the subject's plasma. Large LDL particles range in size from 21.3-23 nm. In one embodiment, the compound increases the percentage of both large size HDL particles and large size LDL particles in the subject's plasma. In one embodiment, the compound increases the subject's plasma level of HDL. In one embodiment, the compound increases the subject's plasma level of insulin-like growth factor-1 (IGF-1). In one embodiment, the compound increases the subject's plasma level of adiponectin. In one embodiment, the compound inhibits the activity of the subject's cholesteryl ester transfer protein (CETP). In one embodiment, the compound inhibits the activity of the subject's apolipoprotein C-3 (APOC-3).

In any of the methods or assays described herein, the cardiovascular-related disease can be hypertension, diabetes mellitus, myocardial infarction, stroke and/or transient ischemic attack.

Since an increased likelihood of longevity also correlates with a decreased likelihood of developing an age related disease, the present invention also provides methods of determining a subject's likelihood of developing such age related diseases, as well as methods of decreasing a subject's likelihood of developing such diseases. Age related diseases include, but are not limited to, forms of cancer and Parkinson's disease.

In any of the methods described herein, the subject can be a human subject or a mammalian subject. The subject can be a male subject or a female subject. In one embodiment, the subjects are male subject. In another embodiment, the subjects are female subjects.

In any of the methods described herein, the control population can be a normal healthy population or a patient population, as appropriate for the particular method being carried out. Differences between the control population and the test group or subject can be assessed using any of the appropriate statistical measures known to those skilled in the art.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

1. Methods and Materials

Study design: The study was designed to characterize the phenotype and genotype of exceptional longevity, as well as certain disease states. Because subjects with exceptional longevity do not have a control group, important in the design was the recruitment of the offspring generation and appropriate control group. A complete description of the design of the study has been published (1, 4, 14). Informed written consent was obtained in accordance with the policy of the Committee on Clinical Investigation of the Albert Einstein College of Medicine. Subjects were recruited by word of mouth and through advertisement in Jewish aging centers and homes. Informed written consent was obtained in accordance with the policy of the Committee on Clinical Investigation of the Albert Einstein College of Medicine.

Study Subjects: Two hundred and thirteen subjects with exceptional longevity (proband) 95-107 years of age (157 females and 56 males, average age 98.2±5.3 (S.D.) years) were recruited to participate in the study. The participant's age was defined by their birth certificate or date of birth as stated in their passport. Proband had to be living independently at 95 years of age, to reflect relatively good health, although at the time of recruitments they could be at any institution or dependency. A population of Ashkenazi Jews, which originate from relatively few founders, was chosen for study. Ashkenazi Jewish founders lived in the 16th-17th centuries in the 'Pale of Settlement' of eastern and central Europe. They were subjected to isolation, inbreeding and then rapid expansion. There is much evidence to support the use of this unique population as a resource to discover important genes, the breast cancer (BRCA) gene being a prominent example (15). This population is also considered homogeneous from socio-economical and educational perspectives; however, this population is comparable to non-Jewish populations in regard to longevity, prevalence of atherosclerotic cardiovascular diseases, and dementia (4). In addition, proband had to have at least one offspring who was willing to be recruited to the study (122 females and 94 males, average age 68.3±6.7 years, range 51-89 years). A case-control study was designed to control for the offspring group. Two different control groups were used. The first control group consisted of the spouses of the offspring (n=75, mean age 70.2±10.2 years, 53% female). Fewer spouses of offspring were recruited than offspring of centenarians because 22 spouses had died, 18 were divorced/separated, 10 were not Ashkenazi Jews, and 55 spouses elected not to participate, leaving the total number of participating spouses at 75. The first control group also consisted of age-matched Ashkenazi Jewish control from the Einstein Aging Study (16) (n=183; 73±2 years of age, 57% female), for a total of 258 subjects. The second control group was an age-matched Caucasian population from the Framingham study (n=589; 67.8±3.5 years, 48% female), to confirm the differences with a non-related population.

Procedures: A single nurse practitioner was sent to all probands in the morning to draw venous blood sample, conduct a physical examination, and obtain a medical history report, including review of the questionnaire, determining weight and body mass index, and administrating the Mini Mental Standard Exam (MMSE) test (17). At that visit the offspring and the participating spouses underwent similar procedures. The control group from the Einstein Aging Study underwent these procedures at their clinical site in the University, and all blood samples were assigned and handled by the General Clinical Research Center at Albert Einstein College of Medicine.

The guidelines of the National Cholesterol Education Program (NCEP), Adult Treatment Panel III (ATP III) (113) were followed in defining "metabolic syndrome" as the presence of three or more of the following five risk factors: 1) increased waist girth (>94 cm for women, >102 cm for men), 2) increased blood pressure (>130//85 or treatment for hypertension), 3) increased fasting glucose (>110 mg/dl or drug treatment for diabetes), 4) low plasma HDL cholesterol (<40 mg/dl), and 5) elevated fasting triglyceride levels (>150 mg/dl). Bioelectric impedance analysis (BIA) was performed with a Tanita BIA body fat analyzer (Body Fat Monitor Scale, BF-625; Tanita Corporation of America Inc., Arlington Heights, Ill., USA).

Lipids and Lipoproteins: Total plasma cholesterol, triglycerides, HDL, LDL, very low-density lipoprotein (VLDL), apolipoprotein AI (apo-AI) and apolipoprotein B (apo-B) concentrations were performed at the laboratories of Montefiore Medical Center—Moses division, where the intra and interassay variations ranged between 2.5 and 3.5% in all these determinations. These measurements were performed for the Framingham study in the central Framingham laboratory as previously described (109). Lipoprotein profiling by nuclear magnetic resonance spectroscopy was analyzed by LipoScience, Raleigh, N.C., as previously described (18, 19). Each NMR measurement produces the concentrations of: intermediate density lipoprotein (IDL), three LDL subclasses, and five HDL subclasses of varying size, given in mg/dL cholesterol concentration units. From the LDL and HDL subclass levels are calculated weighted-average LDL and HDL particle sizes (nm diameter) and LDL particle concentrations (nmol/L). After grouping the 5 individual HDL subclasses into 3 size categories (large, intermediate, small), the following lipoprotein subclasses were considered in the analyses: IDL (23-27 nm), large LDL (21.3-23 nm), intermediate LDL (19.8-21.2 nm), small LDL (18.3-19.7 nm), large HDL (8.8-13 nm), intermediate HDL (8.2-8.8 nm), and small HDL (7.3-8.2 nm). LDL and HDL subclass distributions and particle sizes determined by NMR are highly correlated with those measured by gradient gel electrophoresis (67, 110) and density gradient ultracentrifugation (20). LDL subclass diameters, which are consistent with those measured by electron microscopy, are uniformly ~5 nm smaller than those estimated by gradient gel electrophoresis (111).

As described by LipoScience (76, 78), LipoScience's clinical research service employs proton nuclear magnetic resonance (NMR) spectroscopy to simultaneously quantify subclasses of LDL and HDL. The NMR method exploits the fact that each lipoprotein particle in plasma of a given size broadcasts its own characteristic lipid NMR signal. The signal intensity is directly proportional to the lipoprotein's bulk lipid mass and particle concentration. Larger particles give rise to signals at a different point in a resonance spectrum compared to those from smaller particles, and the shape of each signal is distinct. Measured signal intensities give the particle numbers, since there is a direct proportionality between signal size and the number of particles giving rise to the signal. The increased efficiency of the NMR method is apparent because each lipoprotein subclass in plasma broadcasts its own characteristic lipid NMR signal, analogous to the different sounds produced by bells of different size. Using proprietary spectral software, the lipid methyl group signals are decomposed to give the spectral contributions made by separate sub-populations of lipoprotein particles. A detailed description of the NMR analytical process employed by LipoScience is given in the Handbook of Lipoprotein Testing (77).

IGF-1 and adiponectin assays. IGF-1 was measured using commercial enzyme-linked immunosorbent assay (ELISA): 2-site immunoassays based on paired mouse monoclonal antibodies (DSL, Inc.) after acid/ethanol extraction of the samples (148). These assays do not detect mouse IGF-1. Sensitivity for both is estimated at 0.03 ng/mL at a 1:100 sample dilution post-extraction (149). IGF binding protein assays were carried out using commercial ELISA kits from DSL (133). These assays are based on mouse monoclonal antibodies to the human proteins and display no cross-reactivity with the mouse counterparts. Adiponectin levels were determined using a radioimmunoassay kit (Linco Research, St. Charles, Mo.) or a human ADIPOQ ELISA kit (ALPCO Diagnostics, Windham, N.H. 03087).

Genotyping assay for Cholesterol Esther Transfer Protein (CETP), Hepatic Lipase (HL), Apolipoprotein C-3 (APOC-3), and Adiponectin (ADIPOQ): DNA was extracted from whole blood from all patients. A total of 50 µl PCR amplifications were performed using 100 ng of DNA, 10 pmol of primers and 50 mM dNTPs. The promoter region for HL and CETP gene regions containing polymorphic sites, including nucleotides 250 and 514 for HL and 405 and 442 for CETP were sequenced and analyzed. A 667 bp fragment was amplified using the following primers: HL—(Forward) 5'CAGTC-CTCTACACAGCTGGAAC3' (SEQ ID NO:1) and (Reverse) 5' CGGGGTCCAGGCTTTCTTGG3' (SEQ ID NO:2), CETP—(Forward) 5'AGCGGTGAT CATTGACTGCAG-GAAGCTCTGGC3' (SEQ ID NO:3) and (Reverse) 5'TATTTTTTT CACGGATGGGCA3' (SEQ ID NO:4). PCR conditions were: 3' at 94° C. for one cycle, 45s at 94° C., I' at 66C, I' at 72° C., for 30 cycles conclude with 10' at 72° C., for one cycle. The product than was sent to sequencing using ABI3700 capillary sequencers, and a basic sequencing process consisting of template preparation, reaction, clean up, electrophoresis, and sequence trimming was carried out. Analysis of the sequence outputs was done both manually on the print out and electronically comparing sequences to standard sequences using BLAST software. In addition, several other known CETP multiallelic polymorphic markers (CETP AC(-631)(-629), CEPT D442G, CEPT G(+1), CEPT I405V) were studied, using a multilocus PCR-based genotyping assay (75). Briefly, DNA was extracted from whole blood and amplified using two multiplex 'cocktails' of biotinylated primer pairs to target genomic fragments ranging from 75 to 375 base pairs in size. Amplified fragments within each PCR product pool were then detected colorimetrically with sequence-specific oligonucleotide probes immobilized in a linear array on nylon membranes. Probe specificities have previously been confirmed by sequencing and through use of DNA genotyped independently through other methods such as restriction length polymorphism analysis (75). CETP concentrations in human serum were measured by Elisa (Wako Chemicals USA, Inc. Richmond, Va.).

In addition, several multiallelic polymorphic markers were analyzed for apolipoprotein C-3 (APOC-3) and its promoter, in particular APOC-3 C(−641)A. A multilocus polymerase chain reaction (PCR)-based assay was utilized to genotype known polymorphisms of APOC-3 on chromosome 11q: (−641) C/A, (-482) C/T, (-455) T/C, 1100 C/T, 3175 C/G, 3206 T/G. Briefly, DNA was amplified using multiplex reaction containing biotinylated primer pairs. Amplified fragments within each PCR product pool were then detected calorimetrically with sequence-specific oligonucleotide probes immobilized in a linear array on nylon membranes stripes. Probe specificities had previously been confirmed by sequencing and by use of DNA genotyped independently through other methods such as restriction length polymorphism analysis (73). APOC3 concentrations in human serum were measured by ELISA with a commercially available kit (Wako Chemicals USA, Inc.; Richmond, Va.).

The SNP +2019 insertion/deletion polymorphism in the 3' untranslated region of adiponectin (ADIPOQ) was genotyped using the PSQ HS 96A Pyrosequencer according to the manufacturer's methods (Pyrosequencing, Uppsala, Sweden). Briefly, a PCR product was generated from a primer pair that included one primer covalently coupled to biotin, the biotinylated template was bound to streptavidin-coated Sepharose HP beads, and this mixture was then annealed to a sequencing primer (Forward primer, 5'-ATCCTATAAGGCACAGGG-3' (SEQ ID NO:5), Reverse biotinylated primer, 5'-CTTT-TATAGAGGTACATGTTC-3' (SEQ ID NO:6) and Sequencing primer, 5'-GTATTAAGTGACAGTG-3' (SEQ ID NO:7)). Stepwise elongation of the sequencing primer strand upon sequential addition of a specified sequence of deoxynucleotide triphosphates and the degradation of nucleotides by apyrase were carried out simultaneously. As the sequencing reaction progressed, the DNA strand was extended and the sequence was determined from the measured signal output of light upon nucleotide incorporation. The resulting peaks in the pyrogram were analyzed using Pyrosequencing software.

Statistical analyses: Statistical analysis of the data was performed using PROC MIXED in SAS System Version 6.12 (SAS Institute, Cary, N.C.) and Stata version 8.0SE (Stata Corp., College Station, Tex.). Since the distribution of lipoproteins and sizes were non-normal in many cases, the non-parametric Mann-Whitney test was used for comparisons. Additionally, a multinomial logistic regression was performed to determine which of the incommensurable predictor variables most strongly predicts the phenotype of longevity. Each variable's contribution to predicting longevity was represented by its t-statistic in the multinomial logit model output. Pearson's Correlation Coefficient was also used to express the correlation between variables. Narrow sense heritability ($h^2$) was estimated from the slope of the linear regression of the traits of each parent on the mean value of offspring (12). For a comparison of the difference in allele frequency between the groups, Hardy-Weinberg equilibrium was tested, and the chi-square test was performed. A p-value less than 0.05 was considered to indicate a significant difference. Bonferroni correction for multiple comparisons was applied for the analysis of gene polymorphisms. Subjects' survival distribution was calculated by the Kaplan-Meier method, and the significance of the difference in survival distribution among the groups was tested by means of a log rank test. Wilcoxon statistics were calculated to test homogeneity between the groups. Survival was analyzed by genotype using the Kaplan-Meier survival function estimator and comparisons were made using the log rank test.

2. Results

Lipoprotein properties in families with exceptional longevity (Tables 1 and 2, FIG. 1A-1D): Four groups of subject are represented: centenarians, offspring of centenarians, and 2 controls (Ashkenazi Jews and age-matched Framingham Offspring study). The first group consists entirely of people endowed with a propensity to extreme longevity. The second group should be a mixture of those with and without a propensity to extreme longevity. The two control groups should contain few, if any, people destined to survive in good health to age 95. There were no significant differences between the groups for routine blood chemistries including electrolytes, liver function, and kidney function tests. Body mass index (BMI) was similar in offspring and control groups, which were both significantly greater than in probands. Total cholesterol levels are determined mainly by levels of HDL, LDL, and very low-density lipoprotein (VLDL), which are presented in the Table 1. Particles sizes were directly measured, enabling their assessment independently of the measurements of their plasma apoA, and apoB levels. While probands had lower levels of HDL cholesterol and apo-AI than either their offspring or control groups, their HDL particle size was markedly increased. The number of LDL particles and their size were also increased in probands, and were associated with decreased plasma LDL and apo-B levels.

Differences among the probands, offspring, and controls in the proportions of total LDL and HDL contributed to by the large and small subclasses of these lipoproteins are shown in FIG. 1A-1D. In both probands and offspring, the large HDL subclass accounted for a much greater proportion of total HDL than in the controls, whereas the relative amounts of small HDL were much less than in controls. Similarly, the large LDL subclass was relatively much more abundant in probands and offspring than in controls, while the opposite was true for the small LDL subclass.

Because it was predicted that strong biological markers may be inherited in families with exceptional longevity, studies were conducted of the offspring (likely to inherit biological markers) and control groups, matching their age, total cholesterol, LDL cholesterol, and body mass index (BMI). When offspring are compared with control, the offspring are also remarkable for the large sizes of their LDL and HDL particles. In this case however, HDL and apo-A1 levels were increased, in addition to the decreased plasma LDL and apo-B levels. Because offspring and Jewish control were matched for BMI and VLDL, differences in these variables did not seem to be required for the effects of particle size on longevity. The age-matched Framingham group had higher BMI and cholesterol levels and their lipoprotein profile seems to be worse than the Ashkenazi Jewish control. These differences decreased when adjusted for BMI. Thus, both proband and offspring lipoprotein particle sizes were significantly different than control groups. Females, at any of the lipoprotein characteristic presented, have better profile than males.

A relationship exists between HDL particle sizes to high HDL levels, high apo-A levels, low LDL and VLDL levels and low BMI, and between LDL particle sizes to low LDL and VLDL levels, low apo-B levels, high HDL levels and low BMI. A multinomial logistic regression was performed to determine which predictor variables contribute most strongly to distinguish proband, offspring, and control (Table 2). The predictor variables studied were HDL size, LDL size, HDL, LDL Apo-A1, Apo-B, and BMI. The relative importance of these predictors cannot be assessed by comparing regression coefficients because the variables are not measured in common units or dimensions. Instead, the t-statistics were compared for each variable's contribution to the multinomial logi model. LDL-size and HDL-size were found to consistently exhibit the strongest contribution to this model across all three levels of the subject grouping. In fact, each other variable was non-significant in one or two of the other groups.

Figure 4A:
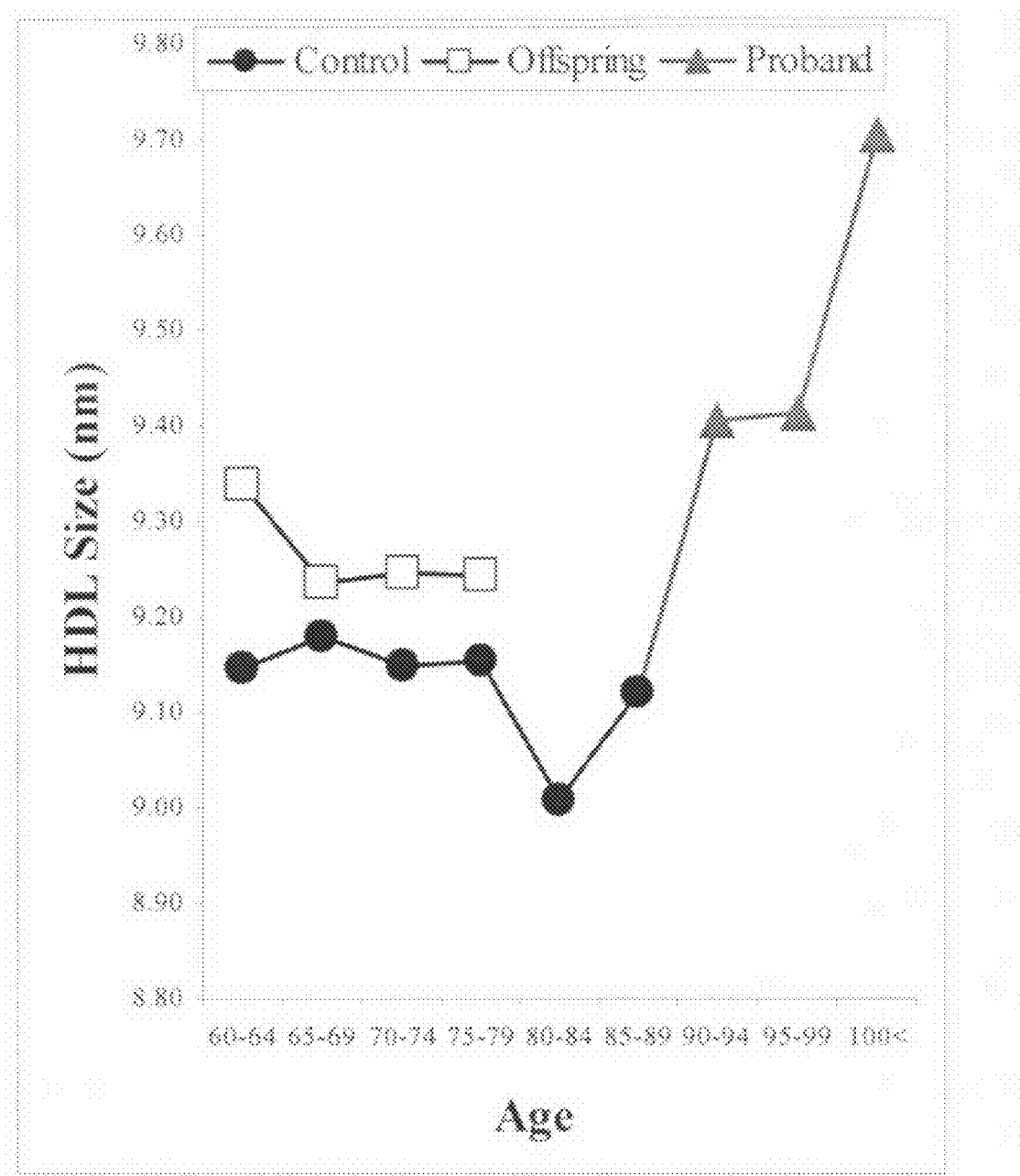
FIG. 4A-4B. HDL (FIG. 4A) and LDL (FIG. 4B) particle size as a function of age. Cross-sectional data from control (closed circles) ages 60-95 (n=878; Ashkenazi and Framingham Study control), proband (triangles) with exceptional longevity ages 95-108 (n=191), and their offspring (open squares) ages 60-80 (n=206).
Figure 4B:
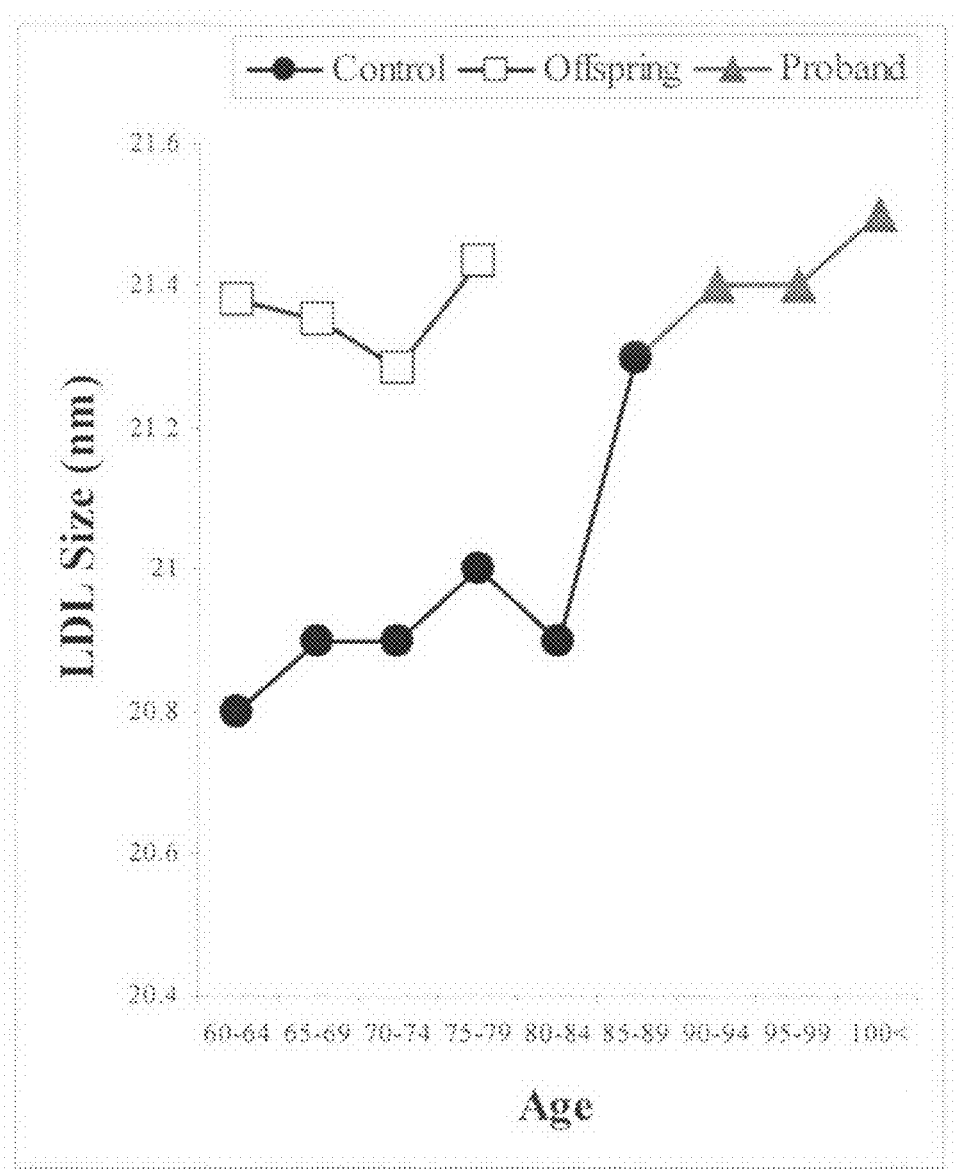

HDL and LDL particle sizes as a function of age (FIGS. 4A-4B). When HDL and LDL particle sizes of all the population are drawn by age, sizes are relatively unchanged until age 85, and then the particles sizes of HDL and LDL increase ($p<0.001$ between centenarians and their offspring compared to either control group, Table 1). The offspring as a group have increased particle size for both LDL and HDL. The same relationship is demonstrated when male and female are considered separately (not shown). Largest HDL particle sizes are greater than 20-fold more likely to belong to proband than to control (FIG. 4A). Similarly largest LDL particle sizes are more than 10-fold more likely to belong to proband than to control (FIG. 4B).

The percent of large, medium and small and LDL and HDL particles (Table 3). The levels of small, medium and large LDL (L1-L3) and HDL (H1-H2, H3, H4-H5) particles were determined (not shown), but since study sub-groups had different total levels of lipoprotein (Table 1), the data represent these particles as a percentage of the total levels of LDL and HDL. Proband HDL particle size increased significantly ($p<0.001$), mostly due to a ~40% increase in the subfraction of large size and a ~50% decrease in the subfraction of medium size HDL particles ($p<0.001$ for both). In parallel, proband LDL particle size was also significantly increased primarily due to a ~20% increase in the fraction of large size LDL particles and a ~50% decrease in the fraction of small size LDL particles ($p<0.001$ for both). Offspring also had increased large HDL and decreased medium HDL particle sizes and increased large LDL and decreased small LDL particle sizes.

The percentage of large HDL was also compared in people aged 85 years and older who had died in a seven year period following collection of the blood samples versus survivors. People who were alive at the end of the seven year period had a higher percentage of large HDL than did those who died during the seven year period (average % large HDL: alive, 67.5%, n=60; died, 60.5%, n=16; p 0.01; large HDL (mg/dL): alive, 32.7, died 25, p 0.002).

Figure 2A:
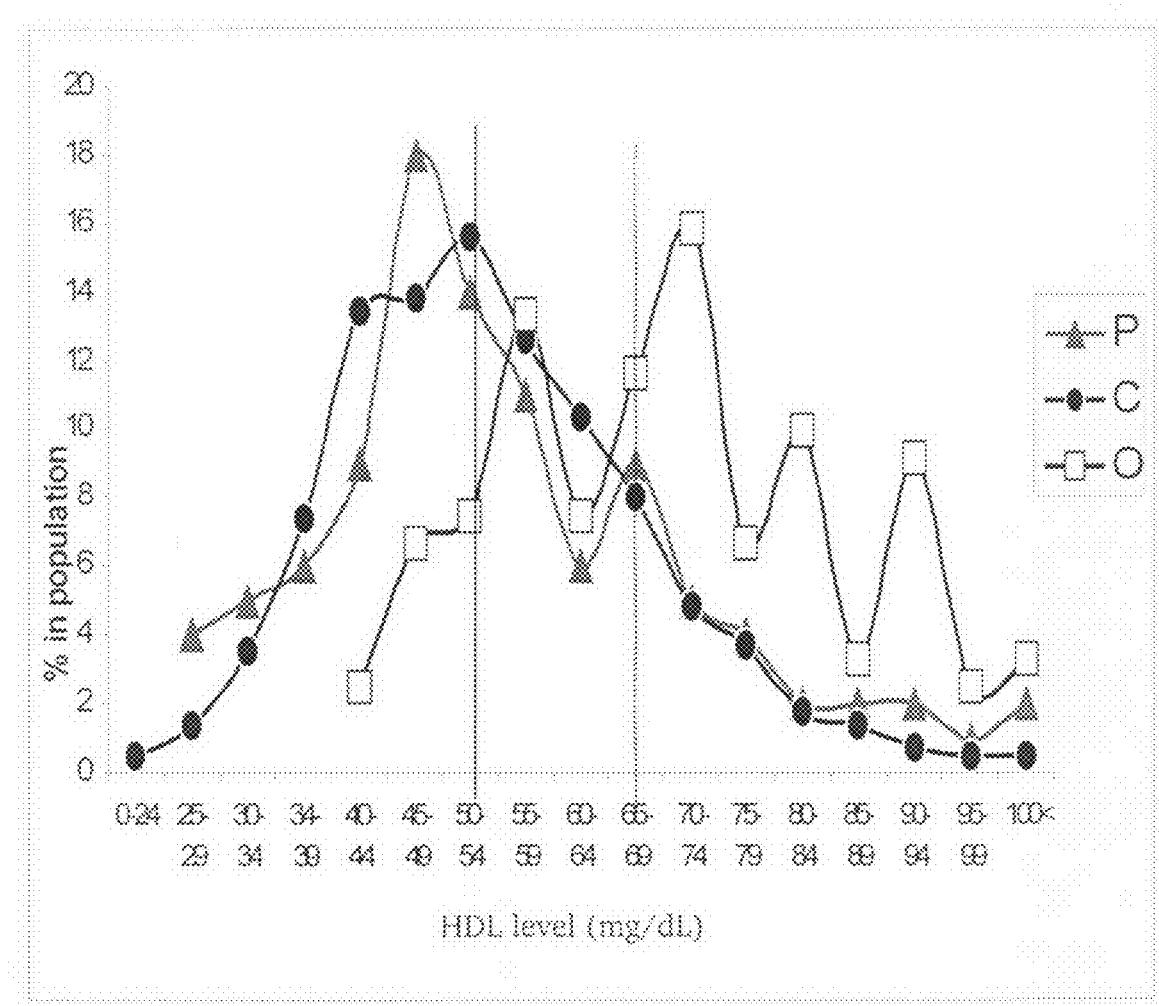
FIG. 2A-2C. Frequency distribution of lipoprotein properties in families of centenarians. The frequency distribution of plasma HDL levels (FIG. 2A), HDL particle size (FIG. 2B), and LDL particle size (FIG. 2C) in female proband (P), their offspring (O), and a control (C) population. Solid lines represent the mean and dashed lines represents 1 Standard Deviation of control. Mean plasma HDL level is similar to control in the proband, but nearly half of the offspring population has plasma HDL levels above 1 Standard Deviation of control, supporting an inherited pattern for a trait that is in decline in the proband. HDL particle size is shifted in the proband to increased size, and it is intermediate in the offspring (bi-modal pattern). Finally, LDL particle size frequency distribution is non-parametric and shifted to larger sizes in proband and offspring.
Figure 2B:
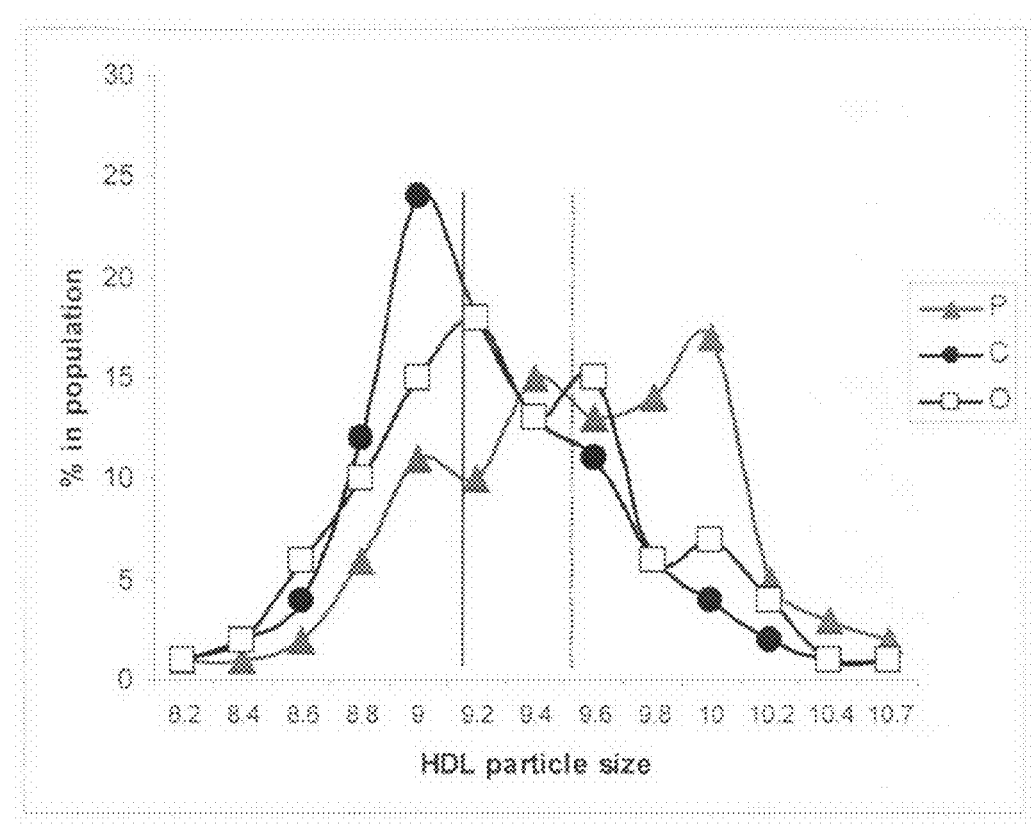
Figure 2C:
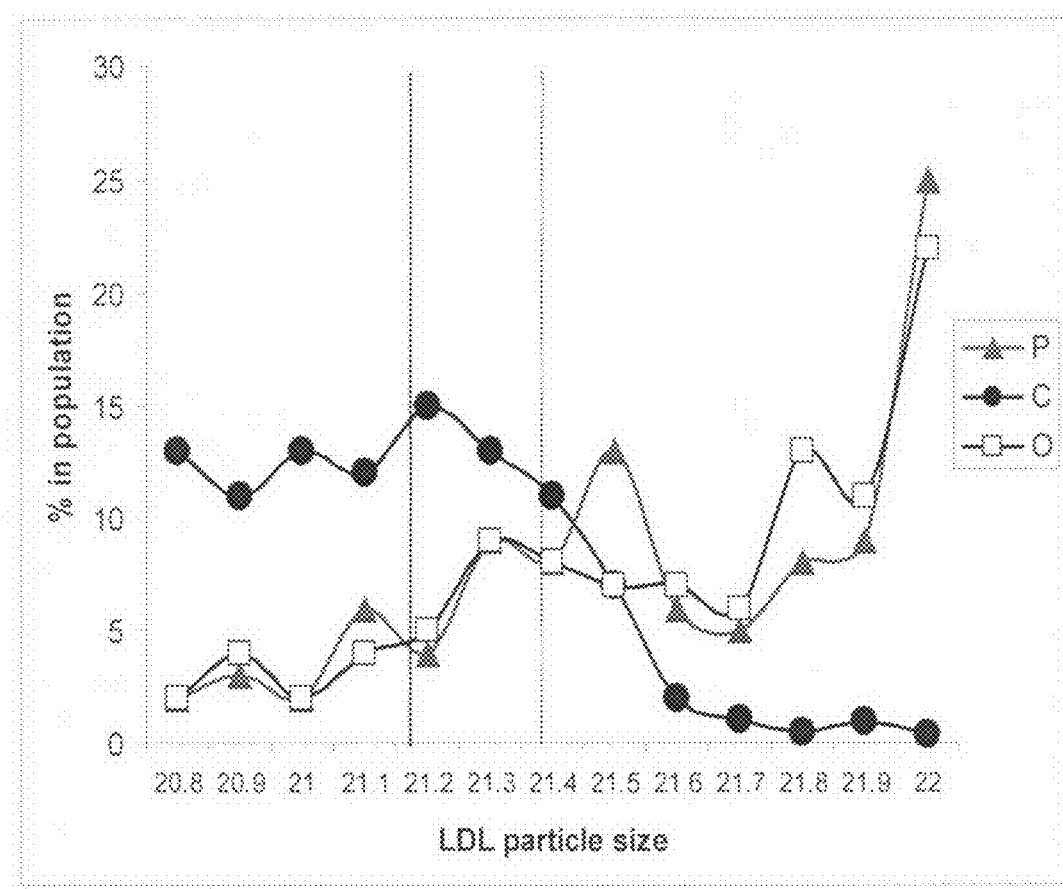
Figure 3A:
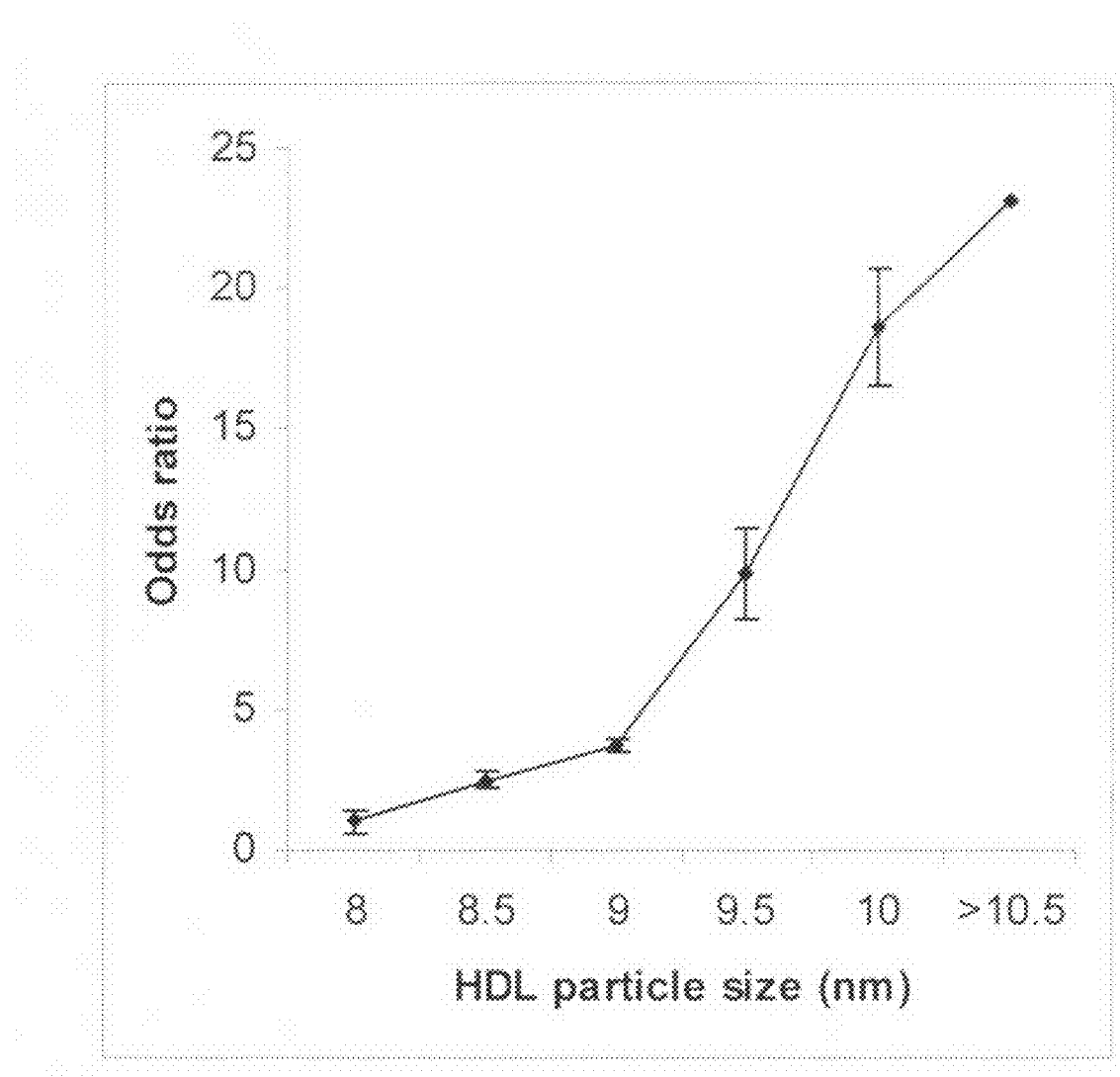
FIG. 3A-3B. Odds ratio of HDL and LDL particle size to belong to proband over control. Large size particles are more likely to come from centenarians than from controls for both HDL (FIG. 3A) and LDL (FIG. 3B).
Figure 3B:
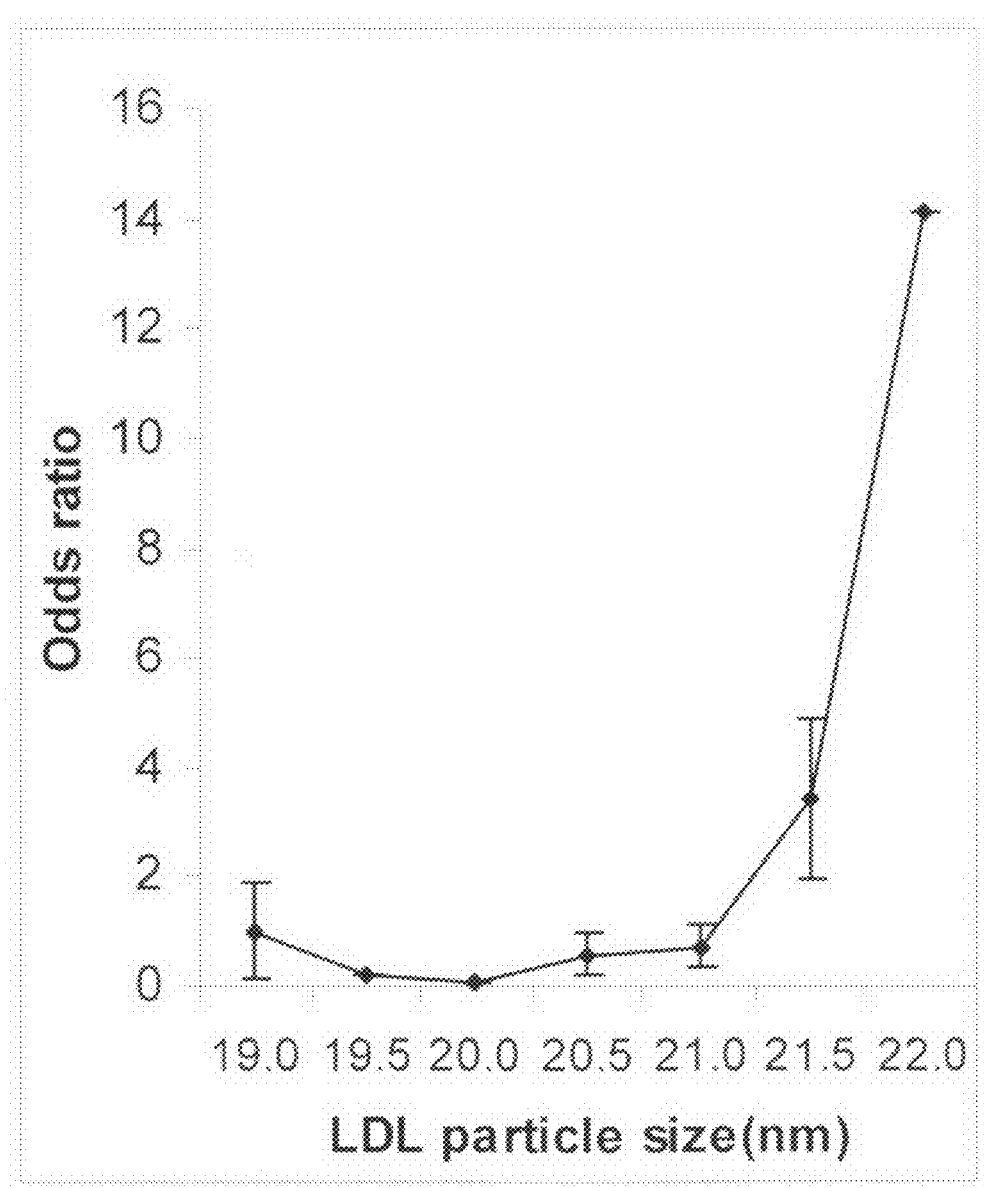

Frequency distribution of lipoproteins properties in families of centenarians (FIG. 2A-2C). The frequency distribution reveals whether the variable is parametric (important for the appropriate statistical test), and also as revealed here, important to suggest patterns of inheritance. The plasma HDL frequency distribution is parametric in female (FIG. 2A) and male (not shown) control with mean values of ~50-60 mg/dl for female and 40-50 mg/dl for male. Offspring have a peak near the mean but other peaks are seen on the right, demonstrating that 46% of the female offspring and 42% of the males (not shown) have plasma HDL levels that are above 1 standard deviation of normal. This pattern is consistent with inheritance of this trait. However, while many probands have unusually high plasma levels of HDL, their distribution is non-parametric, and the mean is approximately averaged. Thus, while plasma HDL levels may prove to be a good marker for longevity in the offspring, proband often do not have, or maintain this characteristic. As with the example for HDL levels above, offspring have a bi-modal frequency distribution of HDL particles size, shifting the distribution to the right, suggesting inheritance of large size HDL particles, as described for plasma HDL levels. However, the most striking feature is that most proband have large particle size. Lastly, the frequency distribution of LDL particle size is non-parametric, and demonstrates that LDL particle size is greater in probands and their offspring than in controls (FIG. 2C). Data for males are similar, although average HDL and LDL particle sizes are lower than in females. When the offspring who had the upper tertile for HDL or LDL particle size were compared with their parents, each of the individual proband had smaller particle sizes than the respective offspring ($p<0.001$). This may indicate that although particle size is higher on average in proband, it may be on the decrease, and their real size and effects may be underestimated here.

Since proband variance was equal between genders while the offspring variance was not equal between genders, heritability of lipoprotein traits was performed in the two offspring genders separately. The heritability ($h^2$) of HDL size is 0.32 (0.16-SD) in female and 0.70 (0.22) in male offspring.

Similarly, the heritability ($h^2$) of LDL size is 0.46-(0.20) in females and 0.6 (0.26) in males. All were statistically significant (p<0.01), supporting a genetic linkage with lipoprotein sizes.

LDL and HDL particles size and cardiovascular disease (CVD) and metabolic syndrome (Tables 4-6). LDL and HDL particle size, and the percent of large particles comprising total levels of the lipoproteins, in the control and offspring with and without hypertension, diabetes mellitus, myocardial infarctions, and strokes/transient ischemic attack (TIA), are presented in Table 4. Subjects without these risks had significantly increased LDL and HDL particle size and higher percent of large particles comprising total levels of the lipoproteins. Similar observation was noted when analyzed only for the offspring with and without CVD risks. Increased HDL levels and decreased LDL levels were also associated with CVD protection, whereas VLDL level was not. The same trend was noted for each individual disease risk, but the numbers were too small to reach statistical significance. This suggests a link between the size of lipoprotein particles and age-related CVD.

Similar results were obtained upon analyzing the relationship between lipoprotein particle size, hypertension, and history of CVD (defined as myocardial infarction, stroke, or transient ischemic attack) in the combined group of offspring and control (Table 5). Significantly higher percentage of large HDL particles, HDL particle size, percentage of large LDL, and LDL particle size where observed in healthy subjects compared to those with hypertension. Moreover, significantly higher percentage of large HDL particles (32%), HDL particle size, percentage of large LDL (54%), and LDL particle size where observed in healthy subjects compared to those with a history of CVD. Interestingly, the lower LDL levels in the hypertension and CVD groups are probably accounted for by use of cholesterol-lowering drugs (18% in the healthy group, 38% in the hypertension group and 60% in the CVD group). Significantly higher levels of HDL in the hypertension and CVD groups were observed compared to the healthy group, but VLDL levels were not significantly different. This observation is also striking when healthy offspring only are analyzed vs. those with hypertension and history of CVD (data not shown). In total, these findings suggest a link between the size of lipoprotein particles and age-related hypertension and CVD.

The metabolic syndrome (a.k.a. insulin resistance syndrome, syndrome X, dysmetabolic syndrome X) (113) is a risk factor for many causes of death (114). Thus, the frequency of metabolic syndrome according to the NECP III guidelines was determined. Since the frequency of the metabolic syndrome increases with age, probands would be expected to have a much higher frequency of the metabolic syndrome than the younger control group. However, the frequency of the metabolic syndrome in probands was 44%, similar to a frequency of 39% in the much younger control group. Most important, offspring had a significantly lower frequency of the metabolic syndrome (26%; p<0.03 vs. control), although these groups were well matched for BMI and age. Subjects with and without the metabolic syndrome were tested to determine their lipoprotein sizes (Table 6). Indeed, larger HDL and LDL particle sizes were apparent in healthy subject than in age-matched subjects with the metabolic syndrome. This effect was not noted for LDL levels, perhaps because of the widespread use of statin therapy. Because reduced HDL level is one of the criteria for having the metabolic syndrome, and is associated with HDL particle size, the analysis was repeated with subjects whose metabolic syndrome was re-defined by 3 criteria other than plasma HDL levels. Lipoprotein particle sizes were still significantly larger in those without the metabolic syndrome. These findings suggest a lower frequency of metabolic syndrome-related traits in subjects genetically predisposed to longevity.

Offspring of centenarians are healthier (Table 7). The prevalence of selected chronic age-related diseases was evaluated in probands and their offspring (n=180, 55% female), compared to three control groups. The first control group consisted of their spouses. The second control group were age group-matched Whites from the National Health and Nutrition Examination Survey III (NHANES III) (n=6728, sample mean 64.7±4.6 years of age). The third control group included all Ashkenazi Jews living in Israel and insured by the largest HMO-type health insurer in Israel (Clalit Health Services; n=219,042, mean age 64.4±2.8 years). Each participant in the offspring case control study completed a questionnaire including questions (worded similarly to the ones used in the Israeli data set, and in NHANES III) regarding a personal history of hypertension, type 2 diabetes mellitus, heart attack and stroke. Because increased body mass index (BMI) is a major determinant of death from cardiovascular, cancer, and all causes of death (88), all subjects underwent a physical examination, which included measurements for BMI, and body fat mass (BFM, using a RJL System for bioelectrical impedance analysis). Offspring of centenarians had significantly better health in all disease categories than did controls (Table 7).

HDL particle size and cognitive function (Tables 8 and 9). Subjects with exceptional longevity usually escape forms of dementia; however, at the end of life many of these subjects have decreases in their cognitive function. LDL and HDL particle sizes and percentage of large particles comprising total levels of the lipoproteins were assessed in the proband with (MMSE<25) and without (MMSE>25) cognitive dysfunction. While LDL particle size had no relationship with MMSE scoring, HDL particle size and HDL levels demonstrated a significant relationship. Coupled with the apparent protective effects of higher HDL levels and large HDL-particle size on CVD described above, these findings suggest pleiotropic effects of large HDL-particle size. Because the offspring of this population almost always score maximally in this test, an assessment of the effect of their lipoprotein sizes on their cognitive function could not be done.

To better assess the significance of this observation, the percentage of subjects with exceptional longevity according to specific clinical criteria for favorable lipoprotein profile are presented in Table 9. Favorable lipoprotein is common in this population, as exemplified by the fact that equal percent of those with cognitive decline had low or high HDL levels. However, better HDL levels, HDL size, and LDL size was observed in more subjects (74, 92, and 75%; respectively) of these with good cognitive function, significantly more than those with a decline. Again, this does not hold true for plasma LDL levels.

Figure 5:
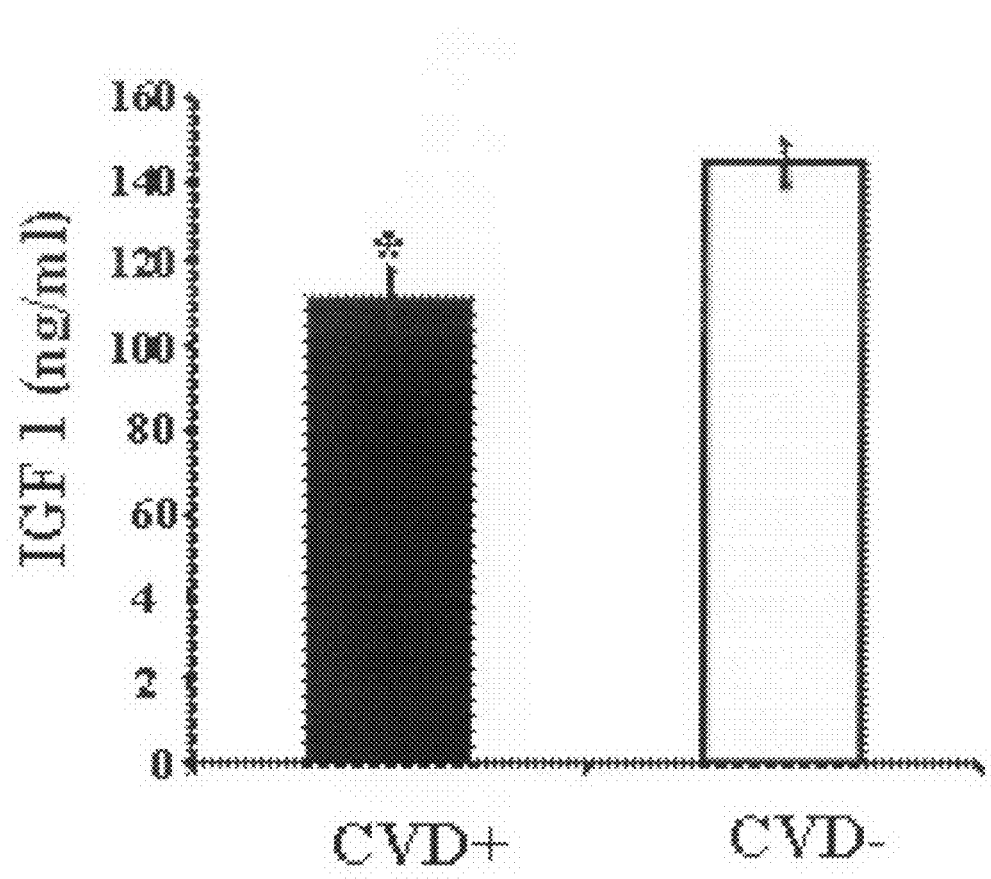
FIG. 5. Plasma IGF-1 levels in offspring with (CVD+) and without (CVD−) cardiovascular-related disease.
Figure 6:
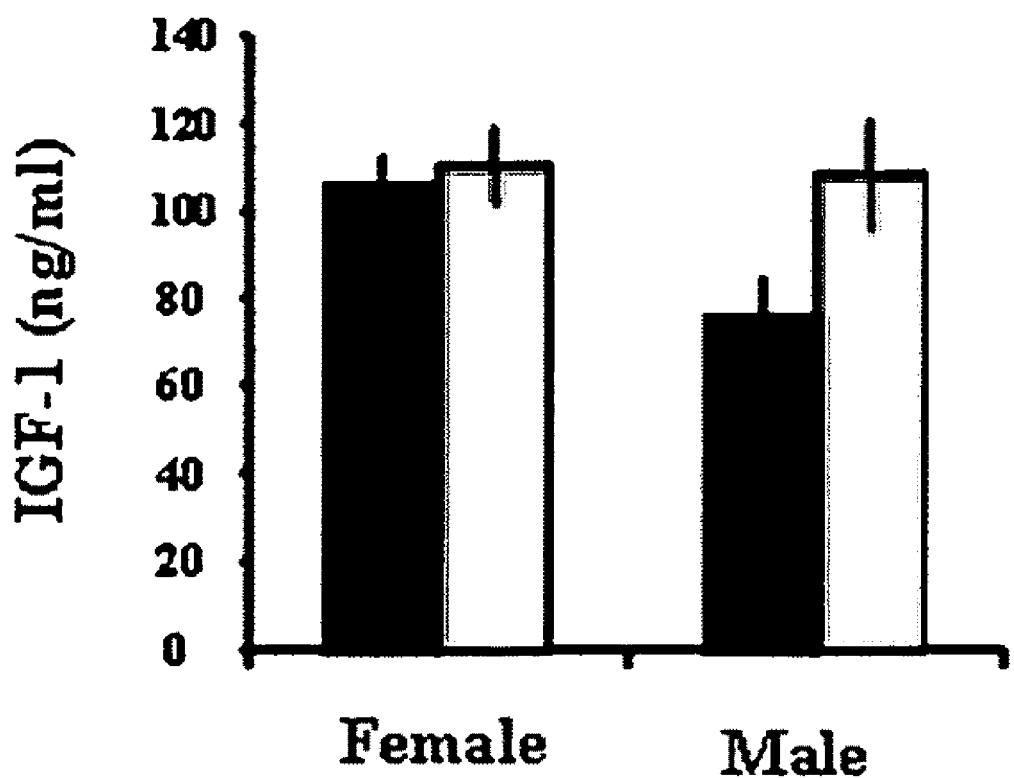
FIG. 6. Plasma IGF-1 levels and cognitive function in proband. Normal cognitive function (MMSE>25) indicated by black columns; impaired cognitive function (MMSE≦25) indicated by open columns.

IGF-1 levels correlate positively with protection from cognitive decline and cardiovascular disease (Table 10, FIGS. 5 and 6). As demonstrated in Table 10, offspring and control, matched by gender, reported similar maximal heights. Proband maximal height was compared to a white population height of U.S. men and women who were 55-64 years of age in 1960-1962, as reported in the National Health Examination Survey of 1960-62 ("General Control" in Table 10, on average less than ~10 years younger than the present cohort). As a group, proband are not shorter than the NHANES control. Because IGF-1 levels decrease with age, it is difficult to assess the meaning of low IGF-1 levels in proband compared with ~30 years younger control. However, female offspring have higher IGF-1 levels than controls (P<0.01), while male offspring have IGF-1 levels similar to controls (Table 10). Strikingly, offspring without cardiovascular disease (CVD−) have significantly higher IGF-1 levels than offspring with cardiovascular disease (CVD+) (FIG. 5). Similarly, male probands with normal cognitive function (MMSE>25) have significantly higher IGF-1 levels than male probands with impaired cognitive function (MMSE≦25) (FIG. 6).

Figure 7:
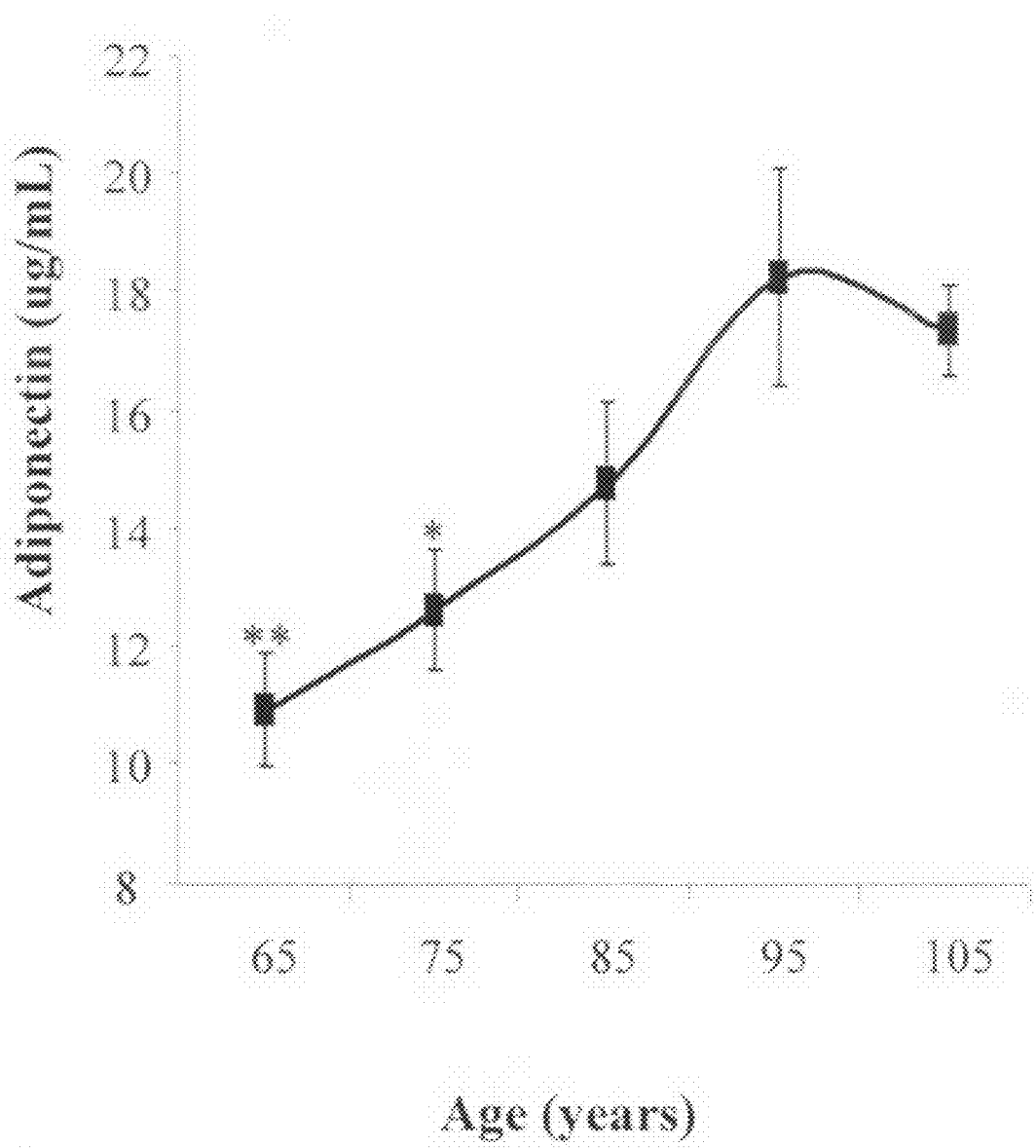
FIG. 7. Adiponectin levels in subjects age 60-108 years. Adiponectin levels, adjusted for gender and BMI in long-lived probands and controls. This group represents a continuous age group of age of unrelated individuals from 60 to 108 years of age. * p<0.01, **p<0.001 vs. 95 and 105 years old FIG. 8A-8B. Distribution of adiponectin levels in probands, their offspring and controls. Panel A: female; Panel B: male. The solid line represents the mean and the dashed lines represent 1 SD of age-matched control.
Figure 8A:
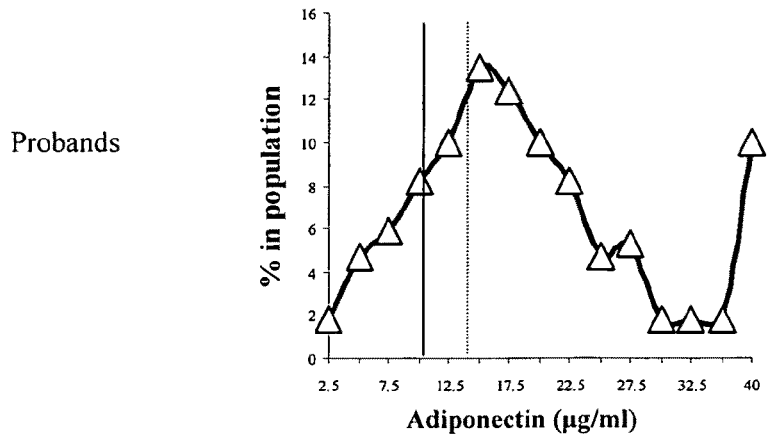
Figure 8A:
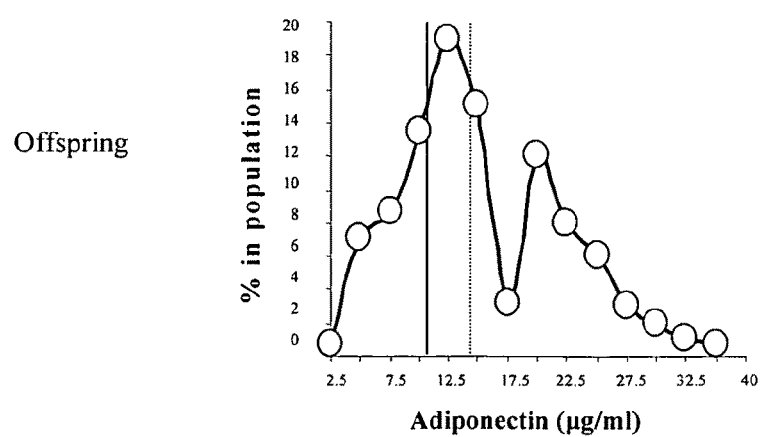
Figure 8A:
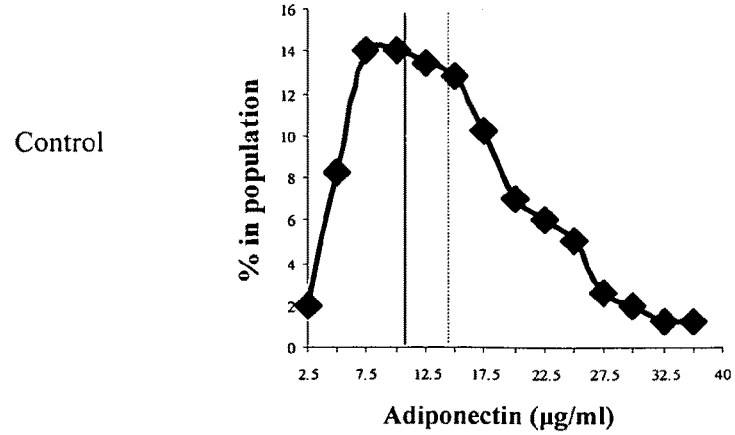
Figure 8B:
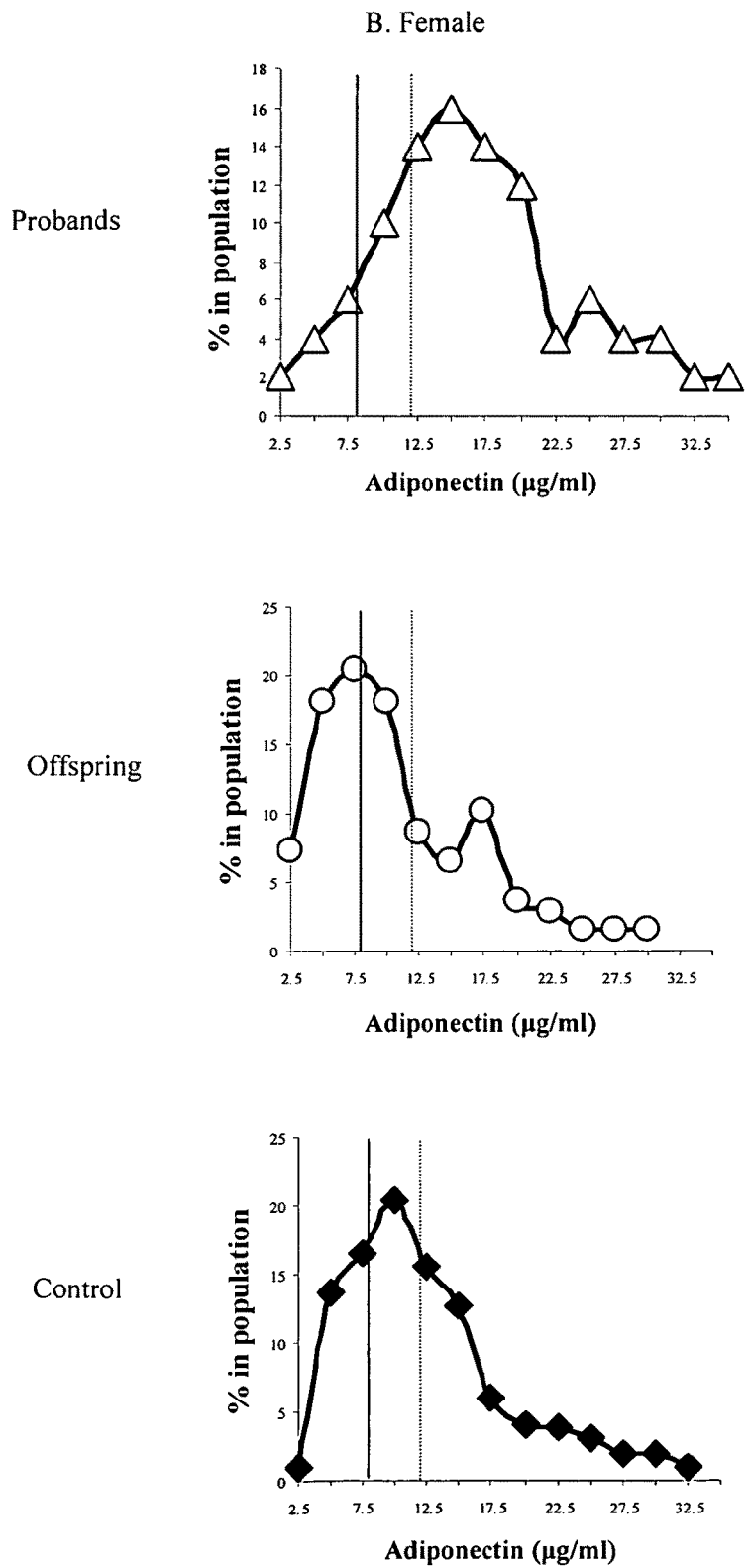
Figure 9:
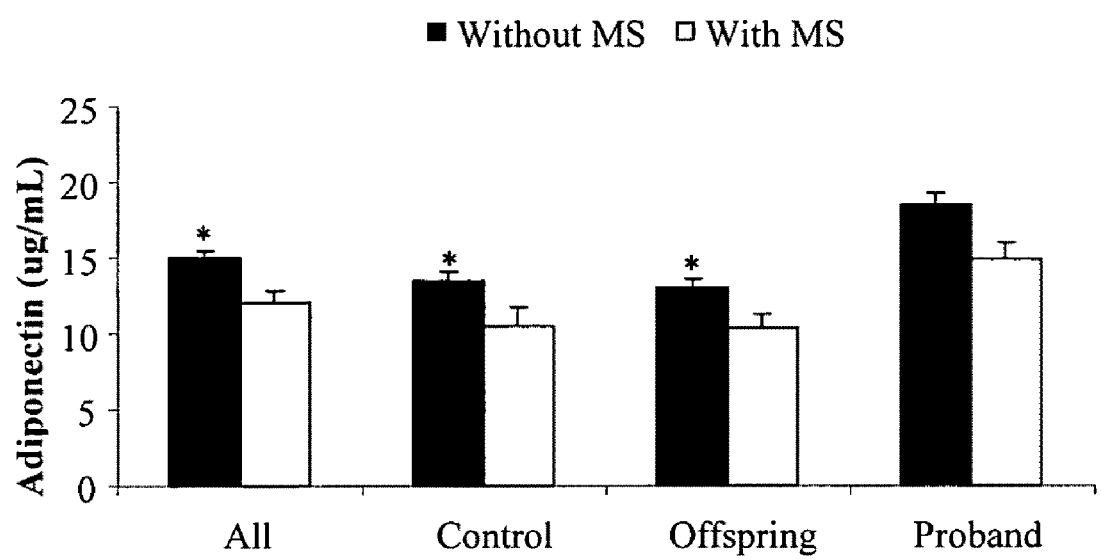
FIG. 9. Adiponectin levels according to genotype and the presence of the metabolic syndrome in probands, their offspring and controls. Adiponectin levels according to metabolic syndrome by NECPIII. *p<0.01.

High levels of adiponectin in families with exceptional longevity (Table 11, FIGS. 7-9). Adiponectin (ADIPOQ) levels were higher in women than men (16.5±0.5 µg/mL vs. 12.5±0.7 µg/mL, respectively, p<0.0001) and were negatively correlated with BMI (r=−0.29, p<0.0001) and percent body fat (r=−0.41, p<0.0001) in both groups, after adjusting for gender, consistent with reports of others (163). Linear regression analysis revealed similar results, namely that ADIPOQ levels were most closely related to gender (F=9.5; p=0-0.002) BMI (F=8.3; p=0.004), HDL particle size (F=5.7; p=0.01) and LDL particles size (F=4.1; p=0.04), but there was no relationship to HDL or LDL levels.

FIG. 7 shows the relationship between age and ADIPOQ levels, adjusted for gender and BMI, in centenarians and control subjects. This group represents a continuous age group of unrelated individuals from 60 to 108 years of age. There is a linear increase of ADIPOQ levels with age that plateaus after age 95 years, suggesting a significant contribution of high ADIPOQ levels to longevity, i.e., a possible survivor effect in those with higher ADIPOQ levels.

The frequency distribution of plasma ADIPOQ levels in probands (centenarians), their offspring and control subjects are shown in FIGS. 8A and 8B for males and females, respectively. Probands had a skewed distribution of ADIPOQ levels that was 1 standard deviation above the mean of the control subjects, reflecting their high ADIPOQ levels. Interestingly, ADIPOQ levels in both male and female offspring demonstrated a bimodal distribution, suggesting that a subset of offspring may have inherited the high ADIPOQ trait. Differences between offspring with high (OADIPOQH) and low (OADIPOQL) ADIPOQ levels are shown in Table 11. The OADIPOQH groups (ADIPOQ level>1 SD above mean for the control group) showed significantly higher HDL levels and larger HDL particle size in both females and males. Large LDL particle size was more frequent and prevalence of the metabolic syndrome was lower in the OADIPOQH group. The female OADIPOQH group was also significantly more insulin sensitive (as measured by HOMA) than the OADIPOQL group. The female OADIPOQH group had lower BMI and percent body fat, which may partly explain the observed differences in lipoprotein particle size, HOMA and metabolic syndrome prevalence. However, similar differences were observed in the male offspring groups, who did not differ significantly in degree of adiposity. Similar results are obtained when the nadir between the 2 peaks was used rather than 1 SD. In addition, subjects who met criteria for the metabolic syndrome had lower levels of ADIPOQ (FIG. 9); this pattern was consistent in probands, offspring and controls. While the OADIPOQL group demonstrated the expected negative correlation between ADIPOQ and both percentage of body fat and BMI (r=−0.27, p=0.02 and r=−0.23, p=0.03 respectively), no correlation between ADIPOQ and body fat or BMI was observed (r=0.1, p=0.58 and r=−0.05, p=0.78 respectively). ADIPOQ levels were significantly heritable ($h^2$=0.36, p=0.05).

Genes regulating lipoprotein sizes in families with longevity (Tables 12-13, FIGS. 10-18). The enzymes cholesteryl ester transfer protein (CETP) and hepatic lipase (HL) have been shown to modulate HDL and LDL levels and sizes. CETP mediates the transfer of cholesteryl ester from HDL in exchange for triglycerides in apolipoprotein B-containing lipoproteins. Analysis was carried out of several of the common polymorphic alleles of CETP (CETP AC(-631)(-629), CEPT asp442, CEPT G(+1)), along with sequencing of most of the HL promoter in these cohorts (negative results not shown), as well as polymorphic sites in apolipoprotein C-3 (APOC-3) and its promoter and a common adiponectin (ADIPOQ) variant that has been shown to influence ADIPOQ levels (164).

Figure 10:
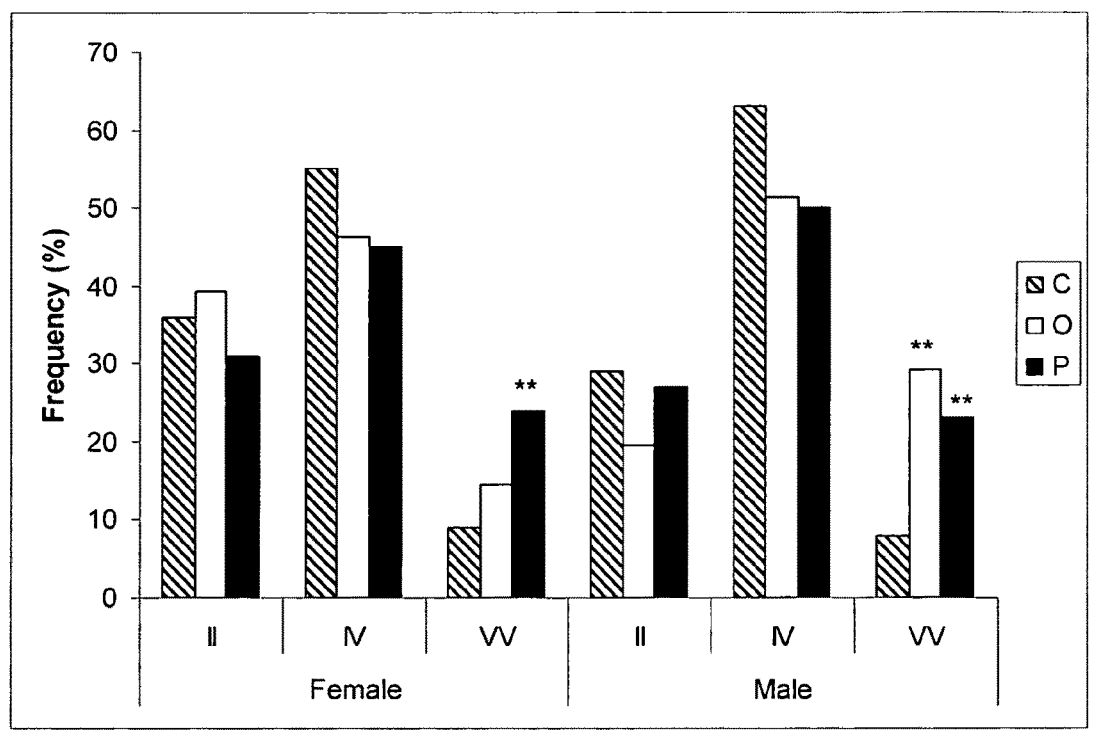
FIG. 10. CETP 405 valine (V) allele in families with longevity. Frequency (%) of homozygosity for the codon 405 valine (V) allele of cholesteryl ester transfer protein (CETP) in female (F) and male (M) probands (P, n=156), offspring (0, n=163), and Ashkenazi controls (C, n=129). The frequency of the VV genotype is ~2-3 fold increased in probands (P) and offspring (O) compared to Ashkenazi controls (C). **p<0.001. I, isoleucine. II—denotes subjects homozygous for isoleucine at position 405. VV—denotes subjects homozygous for valine at position 405. IV—denotes subjects heterozygous at position 405.
Figure 11:
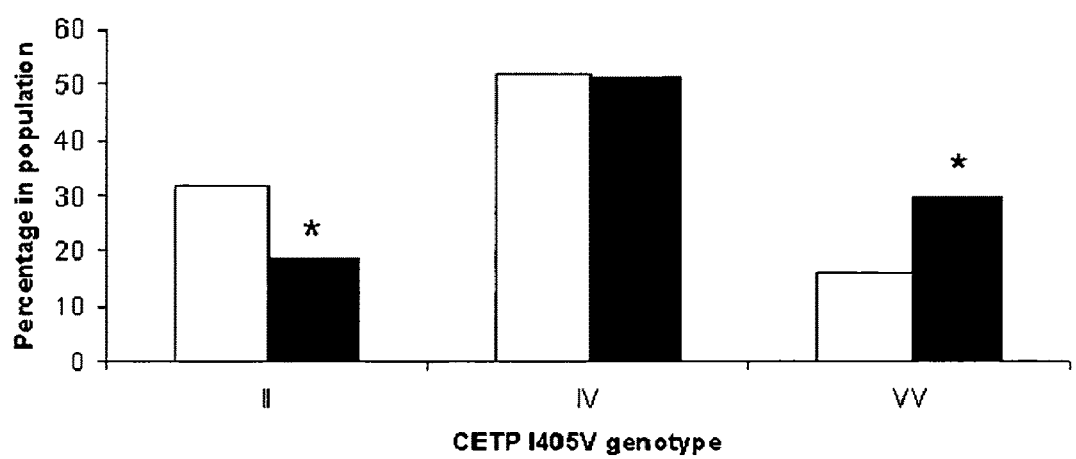
FIG. 11. Relationship between CETP I405V genotype and cognitive function in proband. Normal cognitive function (MMSE>25) indicated by black columns; impaired cognitive function (MMSE≦25) indicated by open columns. II—denotes subjects homozygous for isoleucine at position 405. VV—denotes subjects homozygous for valine at position 405. IV—denotes subjects heterozygous at position 405.

CETP: Allele frequencies of the Isoleucine (I) 405 Valine (V) allele of CETP were 0.46, 0.43 and 0.29 in probands, offspring and Ashkenazi controls, respectively (p<0.01). Strikingly, the frequency of homozygosity for the codon 405-valine allele (VV genotype) was 24.8% in female and male probands compared to only 8.6% in Ashkenazi controls. These differences were statistically significant (p<0.0003) in both males and females (FIG. 10). The offspring of probands had a VV genotype frequency of 20.7%, intermediate between probands and controls and also significantly greater than in controls (p<0.004). The frequency of II, IV and VV genotypes of the CETP Ile405Val mutation in the control is similar to that in other reports (53, 55). The relationships were assessed between the CETP I405V genotype and lipoprotein particle sizes and CETP activity in the control, offspring and proband, respectively. The VV phenotype was associated with significantly larger LDL and HDL particle sizes (Table 12). Furthermore, subjects with the VV genotype had 17% lower CETP concentrations compared to those with II or IV genotype, and HDL level and CETP levels were negatively correlated (r=−0.29, p=0.03; Spearman's rho). These findings suggest a survival advantage for individuals with the VV genotype, perhaps mediated through decreased levels of CETP and its effects on lipoproteins and their particle sizes. No other alleles in CETP or HL had changes in frequency compared to control.

In regard to cognitive function, probands with the CETP VV genotype had an average MMSE score of 27 (95% CI 28.1, 29.4; normal MMSE score being>25). Probands with the II genotype had an average MMSE score of 22 (95% CI 19.4, 25.5; P<0.0004), and probands with the IV genotype had an average MMSE that was intermediate between those with the VV and II genotypes (average for IV=24, 95% CI 22.5, 26.4; p<0.01 vs. VV). As FIG. 11 demonstrates, proband who scored >25/30 (consistent with good cognitive function) had lower frequency of the II genotype (20 vs. 36%) and increased frequency in the VV genotype (33 vs. 15%), with no influence by the IV genotype. Indeed proband with MMSE≦25 are more likely to have the I allele as oppose to subjects with MMSE>25 who are more likely to have V allele (58% and 55% respectively, p<0.05). Thus, proband with CETP VV had significantly better cognitive function than these without. In fact, they were the only proband subgroup with mini mental scores above 25, which is the threshold for cognitive dysfunction.

Probands with the VV CETP genotype have significant lower levels of CETP compare with the II genotype (1.73±0.11 vs. 2.12±0.10 µg/mL respectively; p<0.04). In addition, CETP levels were significantly lower in those with MMSE>25 (1.70±0.07 vs. 1.90±0.06; µg/mL respectively, p=0.03). Similar plasma albumin level (3.89±0.05 and 3.73±0.04 g/dl) and urea nitrogen (25±1 and 28±2 meq/L) in those with MMSE≦25 and MMSE>25, suggest that nutritional status and poor hydration did not influence MMSE testing in this population.

Apo E genotype has been shown to be associated with risk for Alzheimer and CVD risk in the elderly (162), and thus its impact on cognitive function was also assessed in this population. Comparing cognitively impaired subjects (MMSE≦25) to normal subjects (MMSE>25), similar frequencies of Apo E2 allele (4% vs. 9%; p=0.09), Apo E3 (88% vs. 81%) and the 'at risk' Apo E4 allele (7% vs. 10%) were noted.

In regard to cardiovascular disease, subjects with the CETP VV genotype also show a trend toward having a lower incidence of cardiovascular-related disease. No differences in codon 405 CETP genotype were observed between high and low ADIPOQ offspring groups suggesting that the effect of the VV CETP genotype on lipoprotein particle size is not mediated via effects on ADIPOQ levels.

Figure 12:
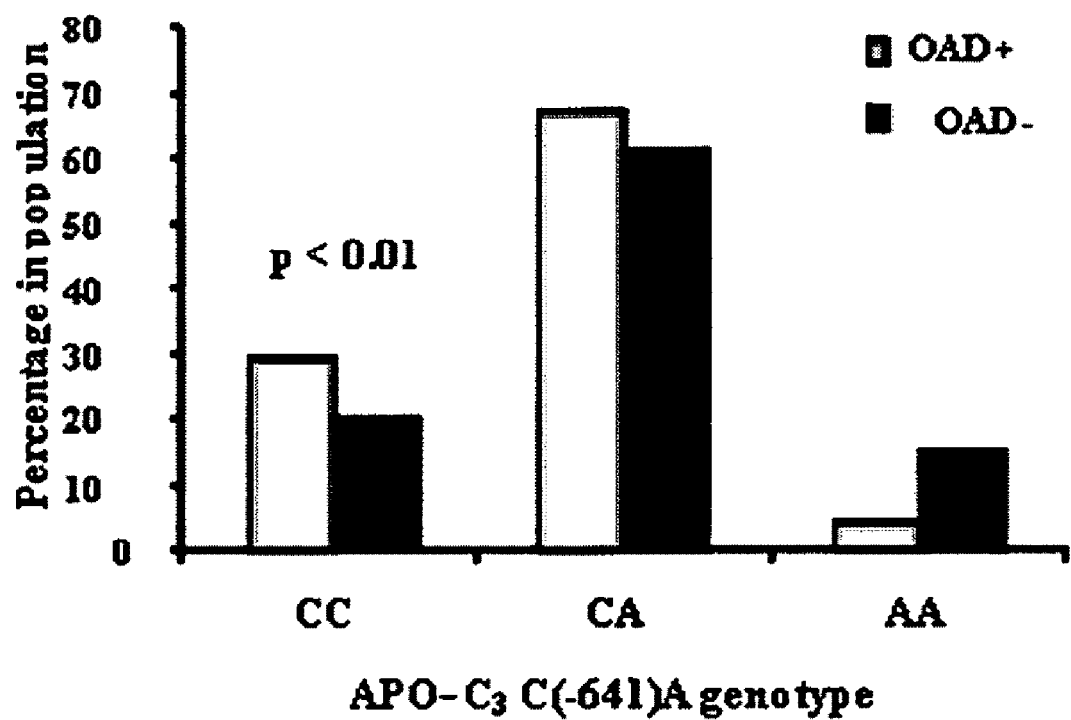
FIG. 12. Relationship between apolipoprotein C-3 (APO-C3) genotype and adiponectin phenotype in offspring with (OAD+) and without (OAD−) high plasma levels of adiponectin.

APOC-3: In regard to apolipoprotein C-3 (APOC-3), there is a striking increase in proband and their offspring, compared to controls, in the frequency of the homozygous cysteine/cysteine (CC) genotype at the C(−641)A promoter site (Frequency=25% in proband versus 10% in controls). The favorable CC genotype was associated with significant higher LDL size (21.39 vs. 21.21 nm; p=0.01). In particular, female offspring with the CC genotype had larger LDL particle size than controls (21.66 vs. 20.97; p=0.0001). Furthermore, HDL levels (72.7 vs. 62.0; p=0.009), but not HDL size, were increased in subjects with the CC genotype. The incidence of the CC genotype was also higher in offspring with high levels of adiponectin (OAD+) than in offspring without high adiponectin levels (OAD−) (FIG. 12). In contrast, CETP did not show any relationship to adiponectin in the OAD+group. Only 5% of subjects with CETP VV and APOC-3 CC have overlapping genotypes.

Figure 13:
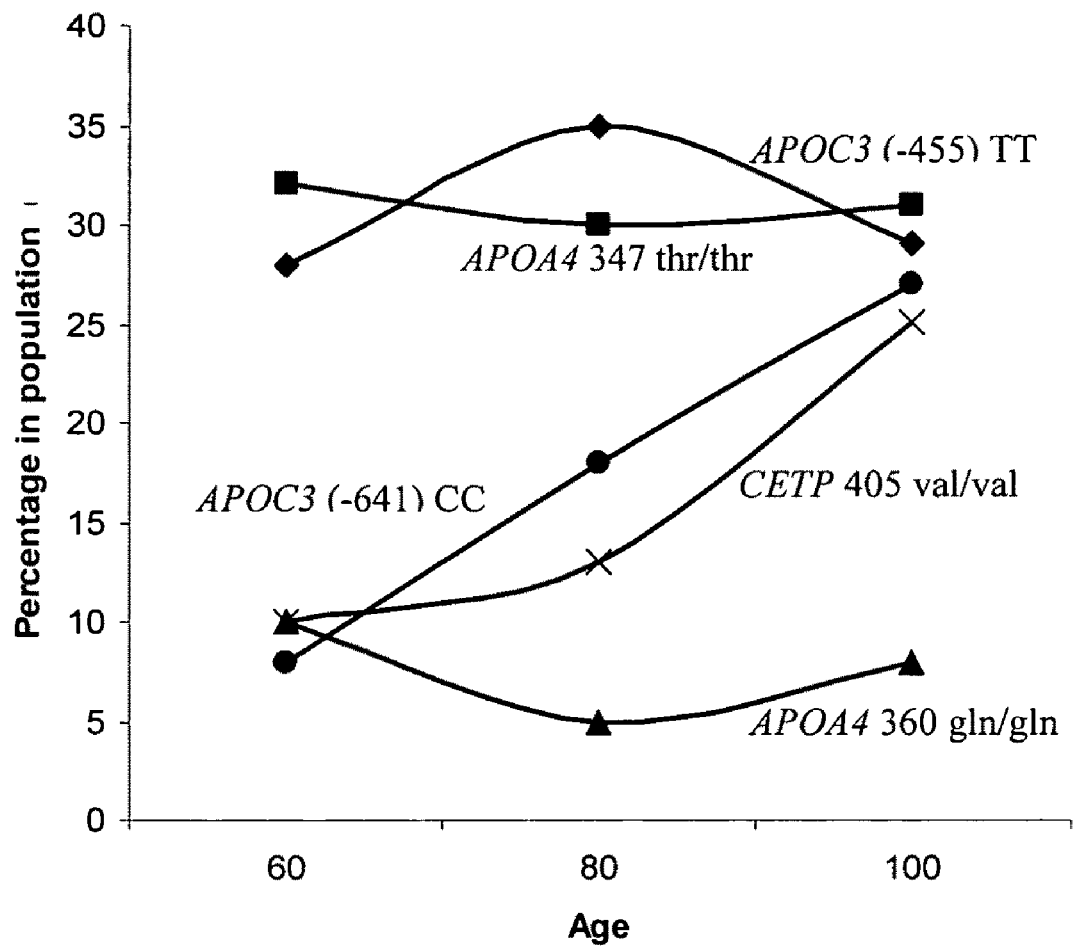
FIG. 13. Distribution of 'favorable' gene polymorphisms of APOC-3, APOA4 and CETP in the study population. The frequency of the favorable gene polymorphisms of APOC-3 (−641) and CETP 405 was analyzed in controls and probands (60 to 100 years old). This figure demonstrates that the frequency of these two variants is higher among centenarians, with monotonic increase with age. Other closely related favorable polymorphisms [APOC3 (−455) TT, APOA4 347 YY, and APOA4 360 HH] were analyzed for control, showing no differences with age.

The APOC-3(−641)CC polymorphism in the APOC-3 gene promoter was substantially over-represented in centenarian probands as shown in FIG. 13. A statistically significant (P=0.03) regression coefficient for both CETP VV and APOC-3 CC genotypes was observed [β=1.89 (95% CI, 0.2 to 3.6) and β=3.06 (95% CI, 0.33 to 5.8) respectively] (FIG. 13). Haplotype analysis of probands and controls resulted with two haplotypes significantly more frequent in each of the groups. First, a CA haplotype, corresponding to two closely located (2 base pairs apart) single nucleotide polymorphisms (SNPs) associated with the CETP gene, was found to be statistically significantly higher among individuals in the control group compared to probands (0.355 vs. 0.278, P<0.004). A significant association was also found between SNPs linked to the APOA4 and APOC-3 genes. An AA haplotype (corresponding to SNP rs675 associated with APOA4, and SNP rs2542052 associated with APOC-3, respectively) is significantly higher among the control group compared to probands (0.483 vs. 0.307, P<10$^{-10}$). An AC haplotype in the same SNPs was found to be significantly higher among the probands compared to controls (0.498 vs. 0.344, P<10$^{-8}$).

Figure 14A:
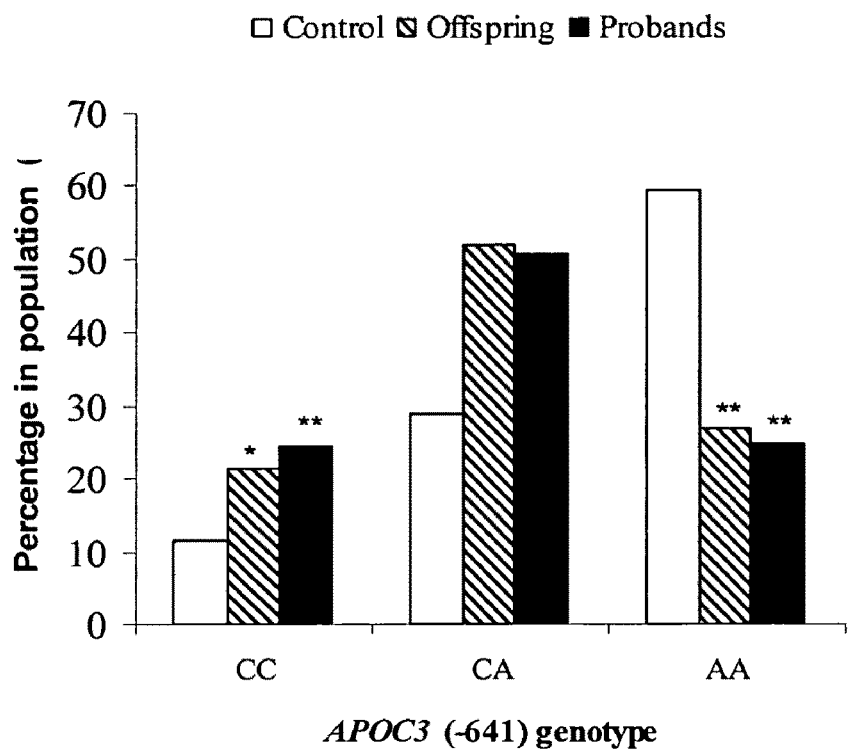
FIG. 14A-14B. Genotype distribution of (A) APOC-3 (−641) and (B) APOC3 plasma concentrations (µg/ml). CC: homozygous for −641 C; AA: homozygous for −641 A; CA: heterozygous for −641; p=0.001, **p=0.0001 vs. control. Bars represent standard errors.

Known variants of the APOC-3 gene were also considered, i.e.: C(-482)T, T(−455)C, C(−641)A, C1100T, C3175G and T3206G. All these polymorphisms have been associated with hypertriglyceridemia, metabolic syndrome and premature coronary artery disease in population based studies (127, 130, 152). The frequencies of all but one of the APOC-3 polymorphisms were similar between the controls and long-lived probands, and were not associated with lipoprotein levels or particle sizes. Those less prevalent polymorphisms of the APOC-3 gene (−482, −455, 1100, 3175 and 3206) were also assessed for associations with TG levels, insulin sensitivity and blood pressure, showing no significant improvement in the subjects with the favorable variants. In marked contrast, the CC genotype at position −641 had a greater prevalence of 25% among the centenarians (p=0.0001) and 20% in their offspring (p=0.001) compared to only 10% in controls. Conversely, the prevalence of the AA genotype was reduced in both centenarians (p=0.0001) and their offspring (p=0.002) compared to controls (FIG. 14A).

Figure 14B:
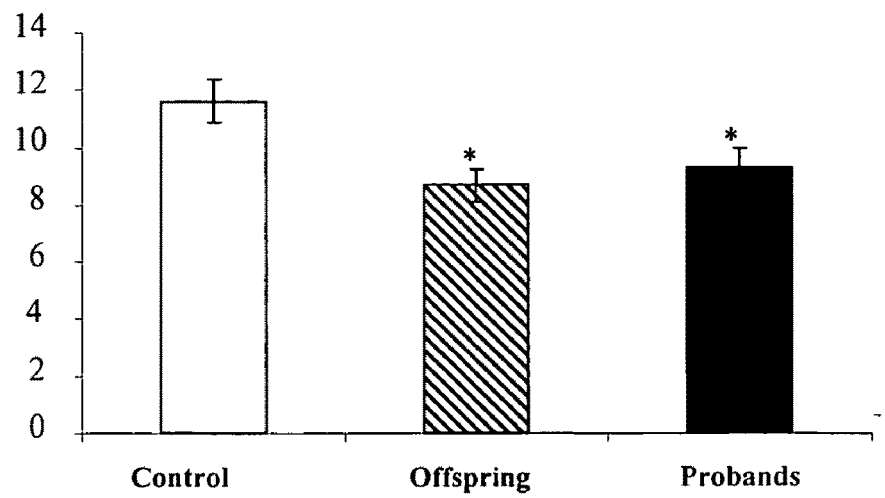

Subjects carrying the CC genotype had lower plasma levels of APOC-3 compared to those carrying either CA or AA (CA/AA) genotype [10.1 (1.1) vs. 13.2 (1.1) μg/ml, p=0.05]. Plasma levels of APOC-3 were significantly lower in centenarians and their offspring than in controls [mean (SE): 9.8 (0.6), 9.3(0.5) vs. 11.7(0.7) μg/ml, respectively; p=0.01 and 0.09] (FIG. 14B).

A variety of lipoprotein parameters were assessed in a subset of the genotyped population of offspring (n=156) and controls (n=129). An analysis of their lipid profile according to their APOC-3 genotype is shown in Table 13. To determine if other apolipoproteins are modified by the APOC-3 genotype and whether or not they could predispose to a favorable or unfavorable phenotype, plasma levels of apoA-1 and apoB were measured. Plasma levels of apoA-1 were significantly higher only in male offspring with the CC variant compared to those with the CA/AA variant, however, the apoA-1 level did not predict their HDL size or concentrations (Table 13). There were no significant differences in the apoB plasma levels between the groups when corrected for genotype (Table 13). Therefore, the effect of the APOC-3−641 genotype is largely unrelated to apoA-1 and apoB phenotypes.

Among female controls, all lipoprotein parameters other than HDL particle size were shifted in the direction associated with lower CVD risk among those with the CC genotype compared to the CA/AA genotypes (p-values ranging from 0.007 to 0.04). The same comparisons were not statistically significant among males. Among offspring, the CC genotype was not associated with any advantage in the lipoprotein phenotype compared to CA/AA carriers in either sex (Table 13).

Because probands and their offspring had significantly lower-risk lipoprotein profiles than controls, an additional underlying protective genotype, specifically CETP VV, may be 'masking' the effect of the CC genotype on the favorable phenotype. Therefore, a comparison was made of the female CA/AA control group to the CA/AA female offspring with and without the favorable CETP VV genotype. Among the 70 APOC-3 CA or AA female offspring, 55 were not carriers of the CETP VV genotype. Female offspring with CA/AA, who were also VV positive had significantly greater HDL particle size (p=0.04), HDL level (p=0.009), LDL particle size (p=0.0006) and LDL level (p=0.01) compared to controls. Furthermore, when comparing controls and offspring with the CA/AA genotype there are significantly better lipoprotein levels and sizes in the latter group (Table 13). Thus, the lack of convincing lipoprotein phenotype in offspring with the CC variant or the better lipid profile in offspring with the CA/AA compared to controls CA/AA can be explained in part by genetic heterogeneity with CETP VV.

Figure 15:
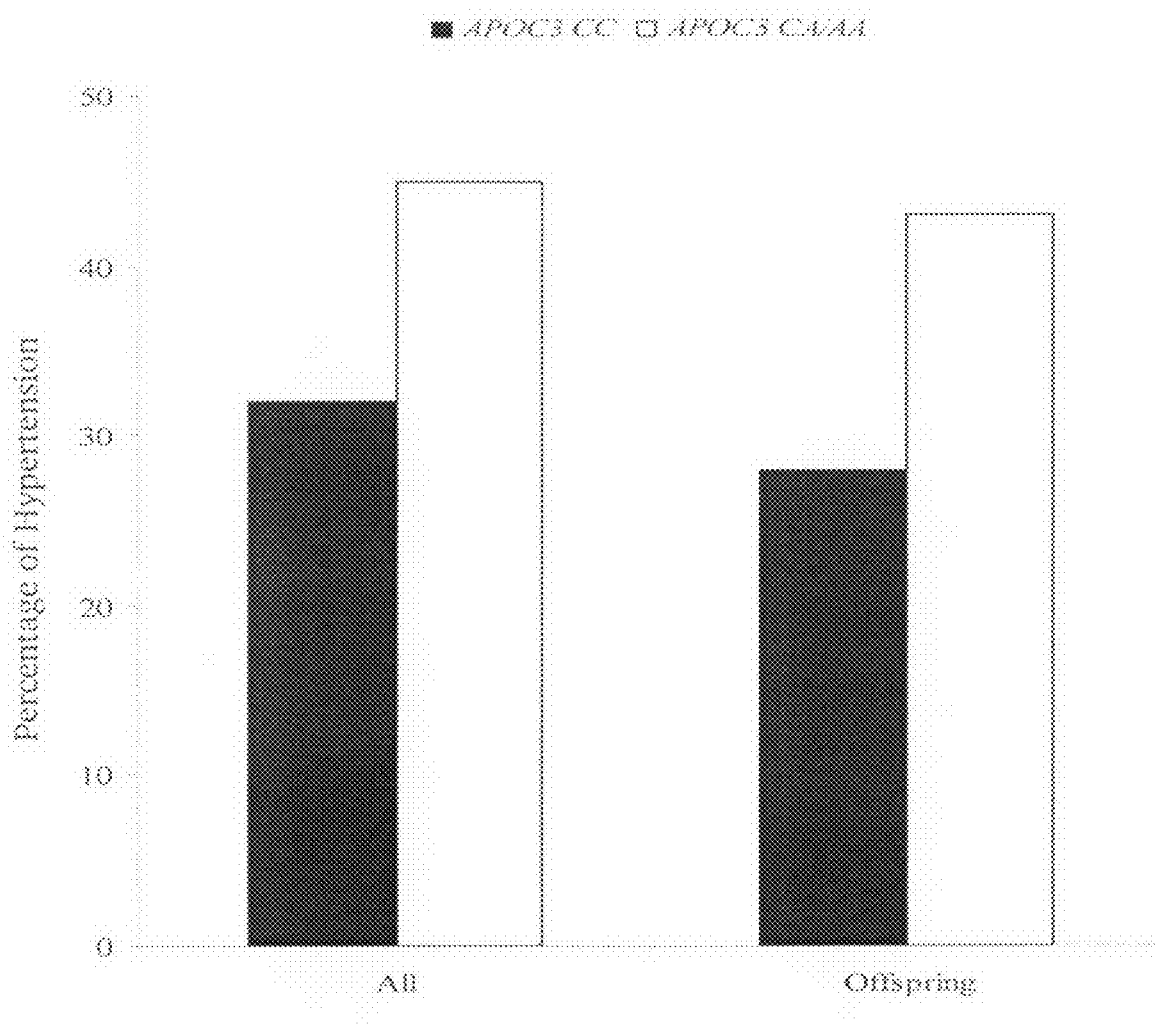
FIG. 15. Prevalence of hypertension in controls and offspring according to APOC-3 genotype. All: includes offspring plus control; CC: homozygous for −641 C; CA/AA: homozygous and heterozygous for −641 A; *p=0.05.
Figure 16:
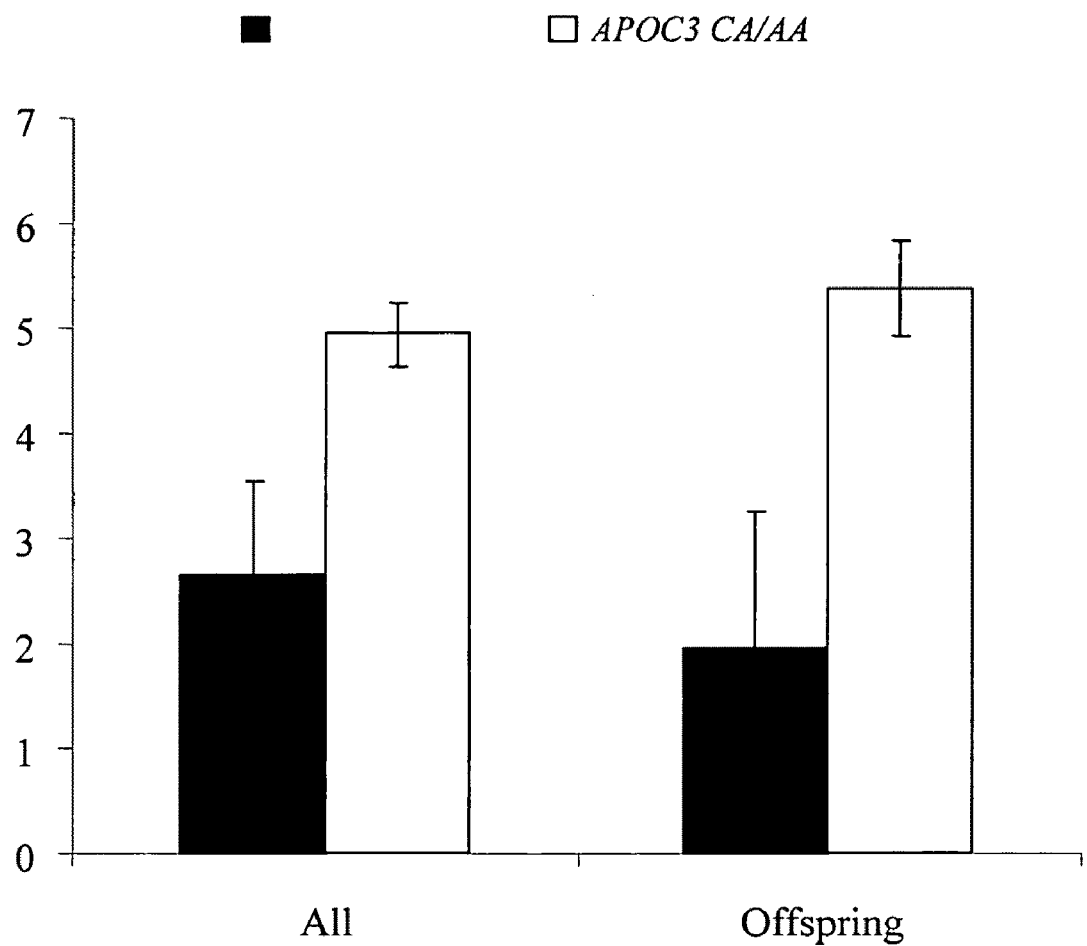
FIG. 16. Insulin sensitivity using homeostatic model assessment (HOMA) in controls and offspring according to APOC3 genotype. Filled bar—APOC-3 CC; open bar—APOC-3 CA/AA. All: includes offspring plus control; CC: homozygous for −641 C; CA/AA: homozygous and heterozygous for −641 A; *p=0.05.
Figure 17:
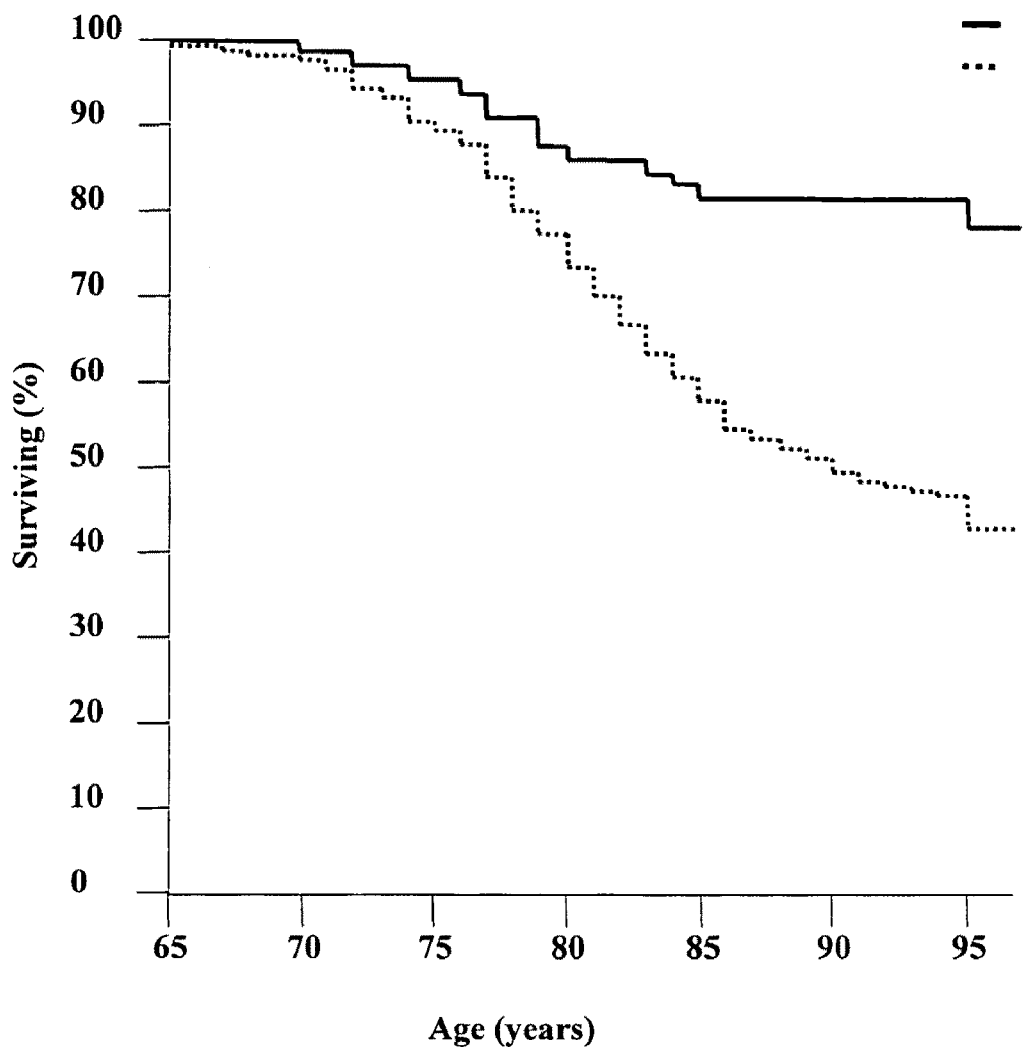
FIG. 17. Survival of the retrospective cohort according to APOC3 genotypes. Analysis conducted with 186 subjects≦95 years of age, from the centenarians and control groups. Offspring were excluded in this analysis because all subjects are currently alive. Solid line—APOC-3 CC; dotted line—APOC-3 CA/AA. CC: homozygous for −641 C; CA/AA: homozygous and heterozygous for −641 A. Test: Log-Rank (p=0.0001); Wilcoxon (p=0.0001).

The most prevalent CVD marker in an aging population is high blood pressure, which was therefore examined in subjects as a surrogate variable for vascular aging. The prevalence of hypertension (as defined in the VII Report of the Joint National Commission on Prevention, Detection, Evaluation, and Treatment of High Blood Pressure) (153) was significantly lower among the carriers of the CC genotype than among those with CA/AA genotypes (p=0.04), especially in the offspring (p=0.03) (FIG. 15). Given that insulin resistance is associated with lipid abnormalities, CVD and death in the elderly (115), insulin sensitivity was measured using the homeostatic model assessment (HOMA) (154). The favorable CC genotype was strongly associated with better insulin sensitivity (FIG. 16). Controls carrying the CC variant also had a greater insulin sensitivity compared to their CA/AA counterparts. The HOMA values among the offspring were significantly better in the CC carriers compared to the CA/AA carriers (p=0.0001, both male and female) and also better than that of the CC controls (FIG. 16). Of 381 subjects genotyped since 1998, 64 had the CC genotype. To describe the relationship between genotype and death, survival of study subjects was plotted by APOC-3 genotype, censoring at age 95 (FIG. 17). Survival is significantly greater among CC genotype carriers (p=0.0001).

Figure 18A:
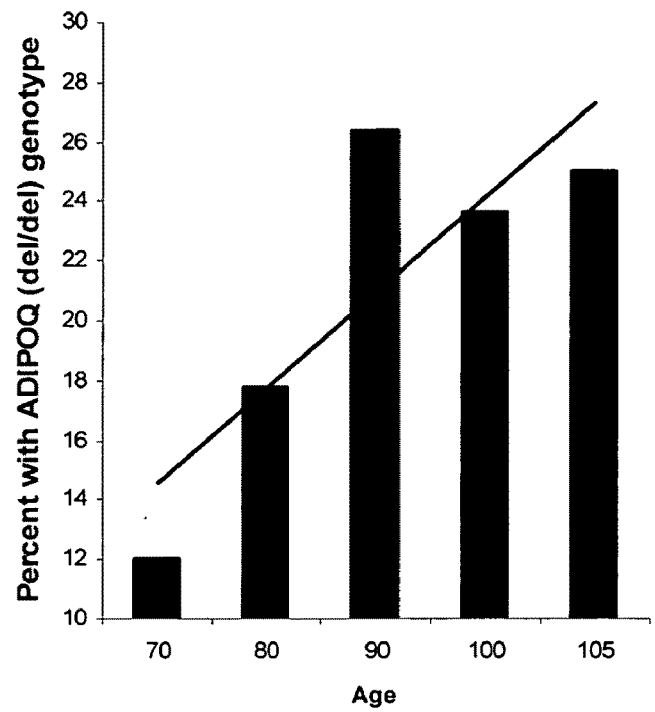
FIG. 18A-18C. Effects of ADIPOQ+2019 del/del genotype. A: Distribution of ADIPOQ (del/del) genotype in subjects age 60-108. Percentage of subjects with the ADIPOQ (del/del) genotype by age group. Regression line β=0.35, p=0.05. B: Adiponectin levels according to ADIPOQ genotype. Significantly higher adiponectin levels were found among the ADIPOQ del/del vs. del/ins and ins/ins genotypes. *p<0.01 for control, offspring, and all groups combined. C: Frequency distribution of ADIPOQ levels according to ADIPOQ genotypes in unrelated subjects age 60-108.
Figure 18B:
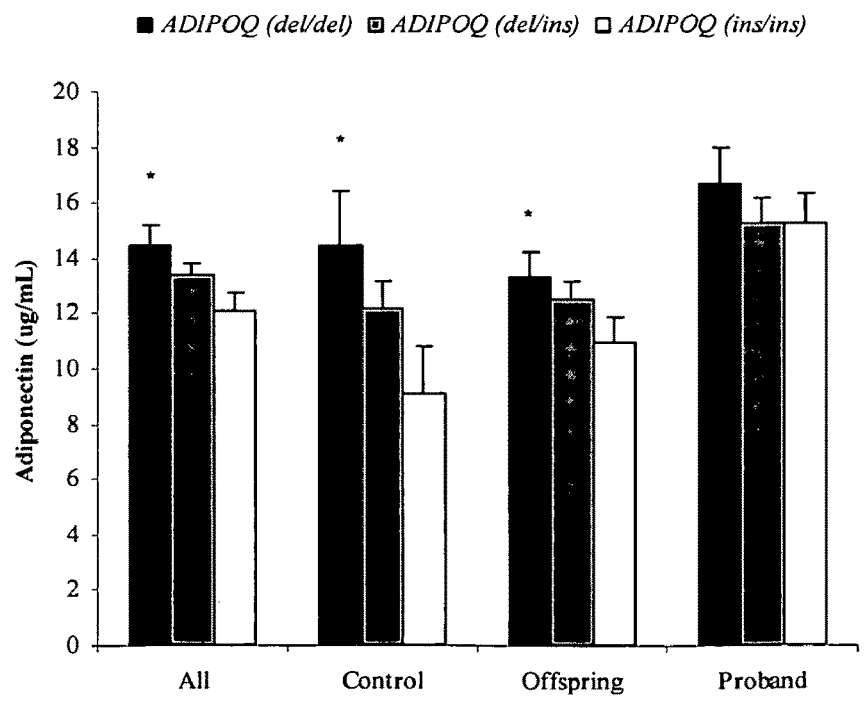

Adiponectin: The frequency of the ADIPOQ +2019 del/del genotype is ~12% in elderly, unrelated subjects between the ages 65-75. At this age mortality is accelerating and by 75-85 over half of the population has not survived, but survivors have increased representation of this genotype (FIG. 18A). Indeed, subject with rare survival to ages 90, 100, and above have a 3 fold over-representation of this genotype. This over-representation in the rare survivors is characteristic for a "longevity gene." Since long-lived parents are enriched with the ADIPOQ +2019 del allele, the frequency of ADIPOQ +2019 (del/del) genotype was significantly enriched in the offspring compared to controls (27% vs. 20%, p=0.04, respectively).

Figure 18C:
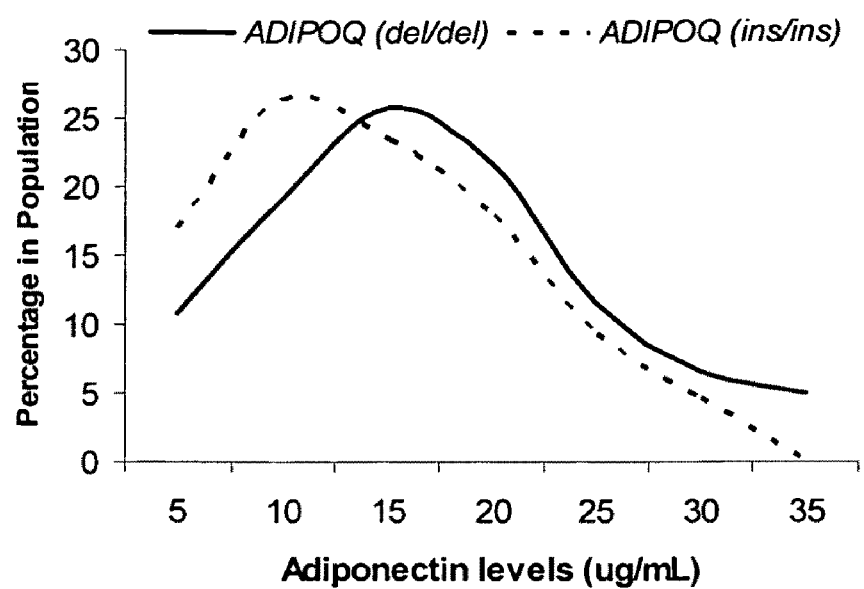

The favorable ADIPOQ +2019 genotype, ADIPOQ (del/del), was present in a greater percentage of OADIPOQH than OADIPOQL subjects (34% vs. 29%, p=0.03). ADIPOQ levels were significantly higher in subjects with the ADIPOQ (del/del) genotype (FIG. 18B), although this difference was less apparent among probands, suggesting that other factors may also contribute to high ADIPOQ levels in those with exceptional longevity. Likewise, the frequency distribution of adiponectin levels according to ADIPOQ +2019 (del/del) genotype, suggests a shift in the distribution to the 'left', further demonstrating a functional effect (FIG. 18C).

Within the ADIPOQ ins/ins the correlation between BMI and ADIPOQ was highly significant (r=−58, p=0.002). However, in the population with ADIPOQ del/del the correlation was not significant (r=−27, p=0.13), suggesting modulation on adiponectin expression or secretion.

3. Discussion

The present application discloses that families with exceptional longevity have a biological marker in the form of increased particle sizes of HDL and LDL, which is largely independent of the levels of their lipoprotein and apolipoproteins. This particular phenotype is associated with a lower prevalence of risk of hypertension, cardiovascular related disease, and metabolic syndrome in their offspring and improved cognitive function in the probands, supporting a functional role in their longevity. The pattern of distribution in the offspring and the markedly increased frequency of homozygosity for the codon 405 valine. CETP allele and for the codon −641 cysteine APOC-3 allele support the inheritability of this phenotype and exceptional longevity.

Because subjects with exceptional longevity escape many other age-related diseases, such as several forms of dementia, infections, and forms of cancer, one may ask whether large HDL and LDL particles are only markers for exceptional longevity or do they have a causative role? Current knowledge and the data disclosed herein support the possibility of causation between lipoprotein particle sizes and exceptional longevity, for several reasons which are discussed below.

In population studies there is usually a strong, mechanistically linked, inverse correlation between plasma levels of LDL and VLDL to HDL levels and HDL and LDL particle size. However, there is compelling evidence implicating LDL lipoprotein particle size as a stronger predictor of cardiovascular disease than LDL levels (21-23). Small LDL particles were shown to penetrate more readily into arterial tissue (24), bind more tightly to arterial proteoglycans (25), and oxidize more rapidly than larger LDL particles (26, 27), and are associated with endothelial dysfunction (28), all mechanisms involved in the development of cardiovascular related diseases. Therefore, large LDL particle size may be important in protecting the vascular bed, and ensuring cardiovascular longevity in the proband. Considering that the prevalence of small particle size LDL (previously called subclass pattern B) is 3-4 fold increased in older compared with young men and women (29, 30), aging effects seem to be reversed in the proband and their offspring. In regard to HDL particle size, small HDL particle size has been demonstrated in patients with cardiovascular related disease (32). In addition, some lipid lowering drugs may shift the HDL particles to bigger sizes in patients with cardiovascular disease, to sizes similar to those seen in patients without cardiovascular disease (31). However, causality between HDL particle size and cardiovascular disease has been debated because of the association of cardiovascular disease with small LDL particles and increased triglycerides (32).

HDL has been thought to exert its effects through reverse cholesterol transport. This ability to clear cholesterol from the endothelial and other peripheral cells may lead to improved organ function. Thus, HDL may have protective effects from 'lipotoxicity' similar to that obtained in caloric restricted rodents, whose life span is dramatically prolonged (33). In addition, other biological properties of HDL have been described including anti-inflammatory (34), anti-oxidative (36), anti-aggregatory (35), anti-coagulant (37), and pro-fibrinolytic activities (38), which are exerted by HDL particles and other components, including interactions with apolipoproteins, enzymes, and even specific phospholipids (39-40). This complexity emphasizes that changes in the functionality of HDL, which could occur through changes in mass or size, may determine the anti-aging effects of HDL. Indeed, the effects of exercise imposed on an elderly population increase lipoprotein size, in the absence of change in lipoprotein levels (20). Such data support the notion that lipoprotein sizes may also be mediating protection from a variety of age-related diseases, down stream to environmental factors such as exercise.

The strongest support for a clinical role for lipoprotein size in exceptional longevity is derived from the data presented herein. The elderly subjects in this study who escaped hypertension, type 2 diabetes mellitus, myocardial infarction, or stroke/transient ischemic attack (TIA) have significantly larger LDL and HDL particle sizes. These data lead to the hypothesis that cardiovascular protection achieved by increased particle size of HDL and LDL is important for exceptional longevity. While centenarians' brain are chronologically old, post-mortem analysis suggests they are free from the typical pathology of Alzheimer's or vascular dementia. Surprisingly, upon testing the cognitive function of proband with exceptional longevity, large HDL, but not LDL, particle size seemed protective from cognitive decline. This may be due to the fact that the large particle size of HDL lipoprotein may play an additional or different role than LDL particle size, and that such a role is unique in the brain. Indeed, increased plasma levels of HDL (which is correlated with HDL particle size in ~70 year old subjects) may offer protection from Alzheimer's (41) and other forms of dementia (42, 43). Furthermore, in a group of elderly, low cognitive function was significantly associated with low HDL levels even after subjects with cardiovascular disease or stroke were excluded, supporting the association between HDL and cognitive function independent of cardiovascular disease (44). As is the case for HDL levels, HDL and LDL particle sizes are significantly larger in women than in men, and may explain why out of 100 people reaching the age of 100 years, 85 are women. It is possible that in order for men to get to 100 years old, VLDL levels also need to be very low.

Because lipoprotein particle sizes correlate with their levels and with their respective apolipoprotein, it is possible that particle size is a marker for another variable that may exert the actual effect. However, the normal plasma levels of HDL and apo-A1, in the face of the largest HDL particle size in proband, strongly challenge this possibility. Moreover, a careful analysis of the data demonstrates that in each of the groups studied (proband, offspring and control), LDL and HDL sizes were markedly and strongly correlated with each other in all groups; however, the other variables assessed by regression had weaker effect and significantly contributed to the phenotype in only one or two of the groups. Furthermore, adjusting for lipoprotein levels, apolipoprotein and BMI, still left lipoprotein particle sizes as the most prominent finding in this study.

The implication of CETP in the genetic analysis also supports the role of HDL particle size rather than its levels in exceptional longevity. In plasma from patients homo- and heterozygous with CETP deficiency, levels of large HDL particles increase two- and six fold, while levels of small HDL remain unchanged with apoE-containing and CE-rich HDL (45, 46). Complete CETP deficiency causes a small-sized LDL population with low affinity for the LDL receptor (47). However, because an upregulation of the LDL receptor increases LDL clearance, CETP deficiency is characterized by lowered LDL levels (49). Interestingly, because cholesteryl ester is not transferred off the HDL particle when CETP activity is low, it may indicate that reverse cholesterol transport may not be the main benefit exerted by HDL and its large particles, and this may have implications for relevant drug development. The support for CEPT involvement in HDL size and its association with exceptional longevity derives from the markedly increased frequency of homozygosity for the codon 405 valine in families with longevity. While this mutation was observed in only ~30% of the proband, it implicates that pathway in the phenotype of longevity. In fact, it represents a 2-3 fold increase in the frequency of this polymorphic allele compared with several control groups. Female offspring of proband had intermediate frequency, and those with the valine allele had the highest HDL and HDL sizes. Interestingly, increased HDL cholesterol levels caused by mutations in CETP were associated with a slight increased risk of ischemic heart disease in white Danish women (53); however, recently the Veterans Affairs HDL Cholesterol Intervention Trial reported that CETP Taq1 B2B2 genotype is associated with higher HDL cholesterol levels and lower risk of coronary heart disease in men (54). It has been suggested that this polymorphic allele in codon 405 valine, which on its own may not be functional, is a marker for another functional mutation in the Taq1 B2B2 (55). Nevertheless, there is no other example for polymorphic allele whose frequency has so dramatically increased in centenarians. As mentioned above, exercise training increases HDL and LDL particle size (20), an effect that seems dependent on CETP genotype (56). Delipidation of HDL by hepatic lipase leads to the generation of smaller HDL subclasses in most subjects (50-52), but increased rates of known or new mutations in the promoter of hepatic lipase were not observed in the present study.

Finally, there is strong evidence for the inheritance of exceptional longevity (2-4). While the increased frequency of the homozygous valine allele in the CETP gene in proband and their offspring support inheritance, so does the pattern of distribution of HDL and HDL particle size in the offspring. While the distribution of this trait is near-normal in controls, offspring have bi-modal distribution for HDL levels and HDL particle size. For plasma HDL levels, 46% of the offspring have levels above 1 standard deviation of the normal, and this proportion is also increased for HDL particle size, supporting the inheritance of a very marked effecter. Plasma HDL levels was shown to decrease with aging, a fact that may explain why levels are slightly low or normal in the proband. Furthermore, the parents of the offspring with the largest HDL and LDL particle sizes had significantly lower particle sizes than their offspring, suggesting that the life-time size of these particles may be underestimated. Following longitudinally the offspring with increased HDL and LDL particle sizes may provide the best evidence for their importance. While these results were obtained in Ashkenazi Jews, the similarity between the control and the Framingham Offspring confirms that this population is not different than other Caucasian populations in the United States. Furthermore, the rates of age-related diseases and life expectancy of the Ashkenazi population of Israel is similar to that of the United States (4), suggesting that the longevity of the subjects of this population is not unique. However, even if the mechanism for exceptional longevity of this population is unique, its applicability may be universal.

In recent years genetic experiments have extended lifespan in lower species by mechanisms that sometimes seem unlikely to be relevant for humans (1). Because humans aging is long and is associated with specific diseases, the relevant mechanisms for longevity should be universal. It is interesting that from all mammalians, CETP is one enzyme that is lacking in rodents, and may have been evolutionary dropped to ensure the longevity of rodents. While the proband have nearly doubled their life expectancy at birth, they are unique in staying healthy until very late age, certainly at the age where their friends got sick and died. The present application indicates that larger HDL and LDL particle sizes are important for longevity, maybe by ensuring protection of the cardiovascular system and the aging brain. It is still to be determined if these particle sizes are sufficient to ensure exceptional longevity, protecting from all causes of death. The CETP 405 valine genotype results in inactivation of the CETP enzyme and larger HDL particle size. Thus, manipulations at the level of DNA, RNA and/or protein that inhibit CETP and/or increase HDL and LDL particle size would be expected to promote longevity and protect from cognitive dysfunction and cardiovascular and age-related diseases.

The −641 C variant of the APOC-3 gene is associated with a phenotype characterized by a significant decline in plasma concentrations of APOC-3, large lipoprotein particle sizes, less hypertension, improved insulin sensitivity and survival advantage. The APOC-3 gene is located on the long arm of chromosome 11 q23, in tandem with the apolipoprotein A1 and A4 genes (152, 154). The APO A1-C3-A4 gene cluster has been studied extensively in relation to lipoproteins and CVD, and in the oldest old (152, 155, 156). APOC-3 is a major component of very low density lipoproteins (VLDL) and chylomicron remnants; it is also a minor component of HDL (152). In vitro, APOC-3 has been shown to inhibit the activity of lipoprotein lipase, resulting in delayed triglyceride (TG) clearance from plasma (157). Levels of APOC3 are positively correlated with plasma concentrations of TG in humans (158). Mice models expressing one to 100 copies of the human APOC-3 gene had large amounts of APOC-3 and were severely to mildly hypertriglyceridemic (159). APOC-3 knockout mice show absence or decreased APOC-3 protein with reduced TG levels (160), even in the presence of streptozotocin-induced diabetes (161). Thus, favorable gene variants would be those that decrease the expression of APOC-3, and ultimately, decrease TG levels. Homozygosity for the CC genotype at position −641 of APOC3, through a decrease in expression of the APOC3 protein, may play a role in facilitating exceptional longevity. The favorable CC genotype was strongly associated with a better insulin sensitivity measured by HOMA. This can potentially contribute to healthier aging in individuals with the CC APOC-3 genotype.

Adiponectin (ADIPOQ) is a fat-derived peptide that has been implicated in prevention of diabetes and inflammation. Exceptionally long-lived probands have markedly higher levels of ADIPOQ. The higher ADIPOQ levels may be responsible, at least in part for the significantly higher levels of HDL, greater LDL and HDL particle size and a lower prevalence of metabolic syndrome in this select group. The distribution of ADIPOQ levels in the offspring group was bimodal, suggesting that a subset of the offspring may have inherited the favorable high ADIPOQ trait. The pattern of distribution of ADIPOQ in offspring, its significant heritability, and association of a common ADIPOQ polymorphism with ADIPOQ levels and with exceptional longevity suggest that genetic determinants of ADIPOQ may contribute to this rare phenotype of exceptional longevity. As in the case of HDL levels, ADIPOQ levels are consistently higher in women than in men. These gender differences in ADIPOQ levels are consistent with lower CVD incidence rates and greater life expectancy observed in women.

TABLE 1

Lipoproteins properties in families with exceptional longevity.

| | Female | | | | | |
|---|---|---|---|---|---|---|
| | Proband N = 157 | | Offspring N = 122 | | Control N = 147 | |
| Trait | Avr | CI | Avr | CI | Avr | CI |
| Cholesterol (mg/dL) | 204*** | (198, 211) | 227 | (220, 233) | 222 | (211, 232) |
| LDL (mg/dL) | 117* | (111, 123) | 128 | (121, 134) | 130.2 | (120, 140) |
| APO B (mg/dL) | 96* | (92, 100) | 104 | (99, 109) | 100 | (91, 108) |
| LDL Size (nm) | 21.49 | (21.40, 21.57) | 21.54 | (21.43, 21.65) | 21.01 | (20.89, 21.13) |
| LDL Particles (nmol/L) | 1079* | (1022, 1136) | 1190 | (1118, 1262) | 1135 | (1012, 1257) |
| HDL (mg/dL) | 56.3*** | (53.6, 59) | 69.9 | (67, 73) | 60.7 | (56.7, 64.6) |
| HDL Size (nm) | 9.546** | (9.469, 9.622) | 9.382 | (9.296, 9.469) | 9.184 | (9.100, 9.267) |
| APO A1 (mg/dL) | 151*** | (146, 157) | 186 | (179, 191) | 165 | (156, 174) |
| VLDL (mg/dL) | 72.8 | (66.5, 79.1) | 71.8 | (63.3, 80.4) | 77.2 | (70.7, 83.7) |
| BMI (kg/m$^2$) | 22.7*** | (22.1, 23.3) | 24.8 | (24.1, 25.5) | 24.7 | (23.8, 25.7) |
| % Fat | 26.8 | (24.6, 29) | 32.1 | (30.6, 33.6) | 32.2 | (29.8, 34.7) |

| | Female | | | | |
|---|---|---|---|---|---|
| | Framingham N = 276 | | P vs. O | C vs. P, O | F vs P, O |
| Trait | Avr | CI | P< | P< | P< |
| Cholesterol (mg/dL) | * | | 0.001 | 0.006, N.S | |
| LDL (mg/dL) | * | | 0.02 | 0.02, N.S | |
| APO B (mg/dL) | * | | 0.01 | N.S, N.S | |
| LDL Size (nm) | 21 | (20.94, 21.06) | N.S | 0.001, 0.001 | 0.001, 0.001 |
| LDL Particles (nmol/L) | 1576 | (1525, 1627) | 0.01 | N.S, N.S | 0.001, 0.001 |
| HDL (mg/dL) | * | | 0.001 | 0.08, 0.001 | |
| HDL Size (nm) | 9.35 | (9.299, 9.402) | 0.005 | 0.001, 0.001 | 0.001, N.S |
| APO A1 (mg/dL) | * | | 0.001 | 0.01, 0.001 | |
| VLDL (mg/dL) | 78.5 | (73.4, 83.5) | N.S. | N.S., N.S. | N.S., N.S. |
| BMI (kg/m$^2$) | | | 0.001 | 0.001, N.S | |
| % Fat | | | 0.001 | 0.001, N.S | |

| | Male | | | | | |
|---|---|---|---|---|---|---|
| | Proband N = 56 | | Offspring N = 94 | | Control N = 111 | |
| Trait | Avr | CI | Avr | CI | Avr | CI |
| Cholesterol (mg/dL) | 183* | (174, 192) | 196 | (188, 203) | 184 | (173, 195) |
| LDL (mg/dL) | 105 | (97, 113) | 112 | (105, 118) | 102.8 | (93, 112) |
| APO B (mg/dL) | 91 | (84, 97) | 95 | (90, 99) | 86.5 | (80, 93) |

TABLE 1-continued

Lipoproteins properties in families with exceptional longevity.

| | | | | | | |
|---|---|---|---|---|---|---|
| LDL Size (nm) | 21.35 | (21.17, 21.53) | 21.11 | (20.95, 21.27) | 20.91 | (20.8, 21.02) |
| LDL Particles (nmol/L) | 1019 | (946, 1092) | 1077 | (1007, 1147) | 949 | (860, 1038) |
| HDL (mg/dL) | 50 | (45, 55) | 53 | (49.6, 55.9) | 48.8 | (45, 52.5) |
| HDL Size (nm) | 9.407*** | (9.243, 9.572) | 9.195 | (8.998, 9.192) | 8.979 | (8.903, 9.055) |
| APO A1 (mg/dL) | 131** | (123, 140) | 148 | (141, 155) | 136.1 | (124, 148) |
| VLDL (mg/dL) | 71 | (60.1, 82) | 75.1 | (64.8, 85.5) | 93.1 | (87.3, 98.8) |
| BMI (kg/m$^2$) | 23.2*** | (22.4, 24) | 26.6 | (26, 27.3) | 25.9 | (24.8, 27) |
| % Fat | 21 | (19.3, 22.7) | 24.2 | (22.9, 25.4) | 23.3 | (21, 25.7) |

| | Male | | | | |
|---|---|---|---|---|---|
| | Framingham N = 309 | | P vs. O Trait | C vs. P, O | F vs P, O |
| | Avr | CI | P< | P< | P< |
| Cholesterol (mg/dL) | * | | 0.03 | N.S, 0.06 | |
| LDL (mg/dL) | * | | N.S | N.S, 0.1 | |
| APO B (mg/dL) | * | | N.S | N.S, 0.04 | |
| LDL Size (nm) | 20.7 | (20.62, 20.74) | 0.06 | 0.001, 0.03 | 0.001, 0.001 |
| LDL Particles (nmol/L) | 1589 | (1546, 1632) | N.S | N.S, 0.05 | 0.001, 0.001 |
| HDL (mg/dL) | * | | N.S | N.S, 0.1 | |
| HDL Size (nm) | 9.04 | (8.996, 9.081) | 0.001 | 0.002, 0.06 | 0.001, N.S |
| APO A1 (mg/dL) | * | | 0.002 | N.S, 0.05 | |
| VLDL (mg/dL) | 74.6 | (68.5, 80.7) | N.S. | N.S., N.S. | 0.005, 0.004 |
| BMI (kg/m$^2$) | | | 0.001 | 0.001, N.S | |
| % Fat | | | 0.006 | 0.1, N.S | |

The Table presents the levels of total, LDL, VLDL and HDL cholesterol, levels of apolipoprotein B (apo B), apolipoprotein A1 (apo A1), sizes of LDL and HDL particles, number of LDL particles, and body mass index (BMI) of male and female probands, their offspring, controls, and subjects from the Framingham Study (F).
*These measurements of the Framingham Study were not obtained using the same laboratory as the other groups. Data are expressed as means and 95% confidence intervals. Significant differences between Probands and Offspring:
*$p < 0.05$,
**$p < 0.01$,
***$p < 0.001$.
NS, not significant.

TABLE 2

Multiple logistic regression analysis for HDL and LDL particle size and the level of HDL, LDL, apolipoprotein B (apo B), apolipoprotein A1 (apo A1), and body mass index (BMI) of male and female probands (P), their offspring (O), and control (C).

| | Proband | | Offspring | | Control | |
|---|---|---|---|---|---|---|
| | t value | P value | t value | P value | t value | P value |
| HDL size | | | | | | |
| HDL-C | 4.48 | <.0001 | 8.28 | <.0001 | 0.01 | 0.99 |
| APO A1 | −1.1 | 0.27 | −4.44 | <.0001 | 1.7 | 0.09 |
| LDL-C | −2.37 | 0.02 | −4.88 | <.0001 | −1.88 | 0.06 |
| LDL Size | 6.4 | <.0001 | 9.19 | <.0001 | 4.72 | <.0001 |
| APO B | −0.53 | 0.6 | 0.97 | 0.3347 | −0.84 | 0.4 |
| BMI | −1.75 | 0.08 | −1.02 | 0.3111 | −2.34 | 0.02 |
| LDL size | | | | | | |
| LDL-C | 1.37 | 0.1739 | 3.52 | 0.0006 | 2.81 | 0.0072 |
| APO B | 1.02 | 0.3099 | −1.98 | 0.0499 | −0.98 | 0.3307 |
| HDL-C | −0.68 | 0.4955 | −2.53 | 0.0123 | 1.71 | 0.0938 |
| HDL Size | 6.4 | <.0001 | 9.19 | <.0001 | 4.72 | <.0001 |
| APO A1 | 0.53 | 0.5985 | 3.37 | 0.001 | −1.04 | 0.303 |
| BMI | 0.34 | 0.7353 | 0.48 | 0.6285 | −0.17 | 0.87 |

A multinomial logistic regression was performed, and t-statistics (t value) and its P value are presented for each variable's contribution to the multinomial logit model. LDL-size and HDL-size consistently exhibited the strongest contribution to this model across all three levels of the subject grouping.

TABLE 3

The percent of large, medium and small LDL and HDL particles as a function of the total levels of LDL and HDL.

| Female | Proband (N = 143) | Offspring (N = 114) | Control (N = 147) | Framingham (N = 276) | Proband vs. Control, Framingham | Offspring vs. Control, Framingham |
|---|---|---|---|---|---|---|
| Large LDL (%) | 72.3 (68-76.5) | 76.8 (72-81.6) | 59.6 (55-64.2) | 56.1 (53.4-58.7) | 0.001, 0.001 | 0.001, 0.001 |
| Medium LDL (%) | 21.6 (17.7-25.3)* | 15.3 (11.4-19.1) | 17.1 (13.7-20.4) | 29.6 (27.6-31.6) | 0.08, N.S | 0.001, 0.001 |
| Small LDL (%) | 6.18 (3.92-8.43) | 7.87 (4.64-11.1) | 23.3 (19.3-27.2) | 14.3 (12.6-15.9) | 0.001, 0.001 | 0.001, 0.001 |
| Large HDL (%) | 61.6 (59.2-63.9)* | 57.4 (54.7-60.1) | 45.5 (42.8-48.1) | 46.7 (44.5-49) | 0.001, 0.001 | 0.001, 0.001 |
| Medium HDL (%) | 10.4 (9.01-11.9)* | 13.5 (11.5-15.4) | 17.1 (13.7-20.4) | 21.7 (20.1-23.2) | 0.08, N.S | 0.001, 0.001 |
| Small HDL (%) | 28 (26.1-29.8) | 29.1 (26.9-31.2) | 23.3 (19.3-27.2) | 31.6 (30-33.1) | 0.001, 0.001 | 0.004, 0.001 |

| Male | Proband (N = 48) | Offspring (N = 92) | Control (N = 111) | Framingham (N = 309) | | |
|---|---|---|---|---|---|---|
| Large LDL (%) | 66.7 (58.7-74.6) | 58.8 (52.4-65.1) | 55.7 (51.3-60.2) | 44.6 (41.9-47.2) | 0.01, N.S | 0.001, 0.001 |
| Medium LDL (%) | 23.6 (16.8-30.4) | 22.2 (17.7-26.7) | 18.5 (14.4-22.6) | 31.9 (29.7-34) | N.S, N.S | 0.007, 0.001 |
| Small LDL (%) | 9.74 (4.13-15.3)* | 19.0 (13.5-24.5) | 25.7 (21.7-29.7) | 23.5 (21.5-25.6) | 0.001, 0.001 | 0.001, 0.06 |
| Large HDL (%) | 56.9 (52.5-61.4)*** | 46.9 (43.3-50.4) | 39.8 (37.5-42.1) | 33 (30.9-35.1) | 0.01, 0.001 | 0.001, 0.001 |
| Medium HDL (%) | 9.8 (7.3-12.3)*** | 15.8 (13.4-18.1) | 18.5 (14.4-22.6) | 25.1 (23.7-26.4) | N.S, N.S | 0.001, 0.001 |
| Small HDL (%) | 33.3 (29.2-37.3) | 37.3 (34.5-40.1) | 25.7 (21.7-29.7) | 41.9 (40.1-43.6) | 0.001, 0.04 | 0.001, 0.06 |

Probands and offspring had increased large LDL and decreased small LDL particle sizes. Probands and offspring also had increased large HDL and decreased medium HDL particle sizes. Data are expressed as means and 95% confidence intervals. Significant differences between Probands and Offspring:
*$p < 0.05$,
**$p < 0.01$,
***$p < 0.001$.

TABLE 4

LDL and HDL particles size and cardiovascular disease (CVD).

| Variable | Healthy (N = 160) | CVD (N = 82) | P value |
|---|---|---|---|
| HDL mg/dL | 55.9 +/− 1.2 | 47.8 +/− 1.7 | 0.001 |
| Large HDL mg/dL | 31.9 +/− 1.17 | 23.6 +/− 1.49 | 0.001 |
| (% Total HDL) | (58%) | (49%) | |
| HDL Size (nm) | 9.33 +/− 0.04 | 9.12 +/− 0.05 | 0.001 |
| LDL mg/dL | 114.2 +/− 2.5 | 101.9 +/− 3.6 | 0.005 |
| Large LDL mg/dL | 79.5 +/− 3.01 | 57.8 +/− 4.43 | 0.001 |
| (% Total LDL) | (70%) | (56%) | |
| LDL Size (nm) | 21.4 +/− 0.05 | 21.1 +/− 0.09 | 0.002 |
| VLDL mg/dL | 70.1 +/− 3.3 | 72.3 +/− 5.5 | NS |

LDL and HDL particle size, and the percent of large particles comprising total levels of the lipoproteins, in the control and offspring with and without CVD risk factors (hypertension, type 2 diabetes mellitus, myocardial infarctions, or strokes/TIA). Subjects without these risks had significantly increased LDL and HDL particle size and higher percent of large particles comprising total levels of the lipoproteins. Similar observation were noted when analyzed for offspring with and without CVD risks. This suggests a link between the size of lipoprotein particles and age-related CVD. Data are expressed as mean ± standard deviation.

TABLE 5

LDL and HDL and their particles size in healthy subjects, subjects with hypertension (HTN), and subjects with a history of cardiovascular disease.

| Variable | Healthy (N = 209) | HTN (N = 64) | CVD (N = 20) | Healthy vs. HTN, CVD P value |
|---|---|---|---|---|
| HDL (mg/dL) | 64.5 ± 19.4 | 57.1 ± 17.2 | 50.8 ± 18.4 | 0.004, 0.003 |
| Large HDL (% Total) | 54.5 ± 16 | 46.8 ± 17.1 | 41.3 ± 18.1 | 0.002, 0.001 |
| HDL Size (nm) | 9.32 ± 0.49 | 9.07 ± 0.42 | 8.96 ± 0.55 | 0.001, 0.001 |
| LDL (mg/dL) | 120.3 +/− 34.9 | 116.9 ± 38.2 | 104.1 ± 35.7 | N.S, 0.03 |
| Large LDL (% Total) | 66.5 ± 27.5 | 57.6 ± 30.7 | 43.3 ± 28.1 | 0.02, 0.001 |
| LDL Size (nm) | 21.4 ± 0.6 | 21.1 ± 0.8 | 20.8 ± 0.8 | 0.008, 0.001 |
| VLDL (mg/dL) | 80.2 ± 77.9 | 93.7 ± 84.6 | 114 ± 90.86 | NS, NS |

Cardiovascular disease (CVD) is defined here as myocardial infarction, stroke or transient ischemic attack. Subjects are pooled Offspring and Control. Data expressed as mean ± S.D. NS, not significant.

TABLE 6

LDL and HDL and their particles size in healthy subjects and subjects with Metabolic Syndrome (MS).

| Variable | Healthy (N = 221) | MS (N = 47) | MS (HDL−) (N = 25) | Healthy vs. MS, MS (HDL−) P Value |
|---|---|---|---|---|
| HDL (mg/dL) | 63.2 (1.14) | 46.6 (1.75) | 46.8 (4.98) | 0.0001, 0.002 |
| Large HDL (% Total) | 66.9 (1.58) | 42 (3.94) | 40.89 (2.9) | 0.0001, 0.0001 |
| HDL Size (nm) | 9.28 (0.03) | 8.88 (0.05) | 8.95 (0.07) | 0.0001, 0.001 |

TABLE 6-continued

LDL and HDL and their particles size in healthy subjects and subjects with Metabolic Syndrome (MS).

| Variable | Healthy (N = 221) | MS (N = 47) | MS (HDL−) (N = 25) | Healthy vs. MS, MS (HDL−) P Value |
|---|---|---|---|---|
| LDL (mg/dL) | 122 (2.14) | 112.9 (5.4) | 114.9 (6.43) | 0.09, 0.32 |
| Large LDL (% Total) | 56.5 (0.9) | 39.7 (2.06) | 51.3 (2.23) | 0.0001, 0.0004 |
| LDL Size (nm) | 21.33 (0.04) | 20.76 (0.11) | 20.97 (0.13) | 0.0001, 0.01 |
| VLDL mg/dL | 66.8 (2.5) | 106.4 (6.3) | 108 (7.2) | 0.0001, 0.0001 |

Metabolic Syndrome defined by NCEP III criteria (113) and by NCEP III criteria excluding HDL (HDL−). Data expressed as mean ± S.E.

TABLE 7

Health of centenarians and their offspring compared to controls.

| Disease | (A) Proband n = 145 | (B) Offspring n = 180 | (C) Control n = 75 | (D) NHANES n = 6728 | (E) IDB n = 219042 | P value A vs. D | P value B vs. D | P value B vs. C | P value B vs. E |
|---|---|---|---|---|---|---|---|---|---|
| HTN (%) | 36 | 33 | 38 | 43 | 45 | 0.22 | 0.03 | 0.57 | 0.008 |
| DM (%) | 6 | 7 | 18 | 14 | 18 | 0.006 | 0.01 | 0.02 | 0.001 |
| MI (%) | 13 | 4 | 15 | 10 | * | 0.19 | 0.007 | 0.001 | |
| Stroke (%) | 2 | 0 | 2 | 6 | 4 | 0.07 | 0.001 | 0.001 | 0.001 |
| BMI (kg/m$^2$) | 22.7 ± 0.3 | 25.2 ± 0.3 | 24.8 ± 0.4 | | | | | 0.3 | |
| PBF (%) | 23.3 ± 0.7 | 27.0 ± 0.5 | 28.1 ± 1.2 | | | | | 0.15 | |

Abbreviations: BMI, body mass index; DM, type 2 diabetes mellitus; HTN, hypertension; IDB, Israeli data base; MI, myocardial infarction; PBF, percent body fat.

TABLE 8

HDL level and particle size and cognitive function. LDL and HDL particle sizes and percentage of large particles comprising total levels of the lipoproteins in the proband with (MMSE < 25) and without (MMSE > 25) cognitive dysfunction.

| Variable | MMSE > 25 (N = 68) | MMSE < 25 (N = 71) | P Value |
|---|---|---|---|
| HDL mg/dL | 60.4 +/− 2.5 | 48.3 +/− 1.7 | 0.0001 |
| Large HDL mg/dL (% Total HDL) | 39.9 +/− 1.17 | 29.6 +/− 1.49 | 0.0001 |
| HDL Size (nm) | 9.51 +/− 0.04 | 9.28 +/− 0.05 | 0.0001 |
| LDL mg/dL | 113.5 +/− 4.21 | 116.8 +/− 4.41 | NS |
| Large LDL mg/dL (% Total LDL) | 69.5 +/− 3.01 | 61.8 +/− 4.43 | NS |
| LDL Size (nm) | 21.0 +/− 0.05 | 21.1 +/− 0.09 | NS |
| VLDL mg/dL | 72.8 +/− 4.8 | 80.2 +/− 4.7 | NS |

While LDL particle size had no relationship with Mini Mental scoring, HDL particle size demonstrated a significant relationship. Data are expressed as mean ± S.D. MMSE, Mini Mental Standard Exam.

TABLE 9

Percent of subjects with exceptional longevity according to favorable lipoprotein profile and cognitive function (by MMSE).

| | Minimental | | |
|---|---|---|---|
| | >25 | ≤25 | P value |
| Low HDL (%) | 26 | 51 | 0.0002 |
| High HDL (%) | 74 | 49 | |
| HDL size ≤8.8 (%) | 8 | 15 | 0.05 |
| HDL size >8.8 (%) | 92 | 85 | |
| Low LDL (%) | 28 | 36 | 0.22 |
| High LDL (%) | 72 | 64 | |
| LDL size ≤21.3 (%) | 25 | 39 | 0.03 |
| LDL size >21.3 (%) | 75 | 61 | |

Subjects were assigned according to those with high HDL levels (>50 mg/dL in female and >40 mg/dL in male) (113), large HDL particle size (>8.8 nm), large LDL particle size (>21.3 nm), low LDL level (>130 mg/dL).

TABLE 10

Height, and IGF-1 and IGF binding protein-3 (BP-3) plasma levels in Proband, Offspring and their Control, and in a General Control group.

| | Offspring | | Control | | Proband | | General Control | |
|---|---|---|---|---|---|---|---|---|
| | Female | Male | Female | Male | Female | Male | Female | Male |
| N = height | 143 | 134 | 65 | 39 | 136 | 43 | 443 | 418 |
| Maximal Height (inches) | 63.4 (2.26) | 69.5 (2.57) | 64.4 (2.56) | 69.4 (2.24) | 62.5 (2.33) | 66.8 (2.87) | 60.5 | 66.9 |
| N = IGF-1 | 65 | 45 | 21 | 14 | 78 | 26 | — | — |
| IGF-1 (ng/ml) | 130* (57) | 163 (51.4) | 115 (52.6) | 163 (61.2) | 111* (51.8) | 87.5* (39.1) | — | — |
| BP-3 (ng/ml) | 1356 (1857) | 948 (1498) | 1389 (1815) | 860 (1393) | 934 (1416) | 531 (984) | — | — |

*p < 0.01 vs. control. Data presented as Mean and (S.D.).

TABLE 11

Lipoprotein concentrations and particle sizes in offspring with high (OADIPOQH) and low (OADIPOQL) adiponectin levels.

|  | Females | | | Males | | |
| --- | --- | --- | --- | --- | --- | --- |
| Number of subjects | OADIPOQL 80 | OADIPOQH 32 | P value OADIPOQL vs. H | OADIPOQL 68 | OADIPOQH 42 | P value OADIPOQL vs. H |
| Age (years) | 69.4 (0.7) | 69.7 (0.8) | 0.8 | 69.7 (0.6) | 71.1 (1.1) | 0.29 |
| Adiponectin (ug/mL) | 10.8 (0.39) | 22.9 (0.7) | 0.0001 | 6.48 (0.3) | 18.2 (0.68) | 0.0001 |
| BMI | 26.4 (0.5) | 23.7 (0.5) | 0.003 | 27.2 (0.4) | 25.8 (0.4) | 0.08 |
| % Fat | 34.6 (0.84) | 31.5 (0.94) | 0.03 | 24.5 (0.6) | 23.8 (0.94) | 0.53 |
| Cholesterol (mg/dL) | 222 (4.1) | 226 (5.51) | 0.5 | 192 (3.45) | 197 (6.45) | 0.5 |
| Triglyceride (mg/dL) | 161 (9.36) | 116 (10.9) | 0.005 | 171 (11.8) | 124 (11.7) | 0.02 |
| HDL (mg/dL) | 65 (1.7) | 77 (2.8) | 0.0002 | 51 (1.7) | 59 (2.3) | 0.007 |
| Large HDL particle size (% of Total) | 51 (1.7) | 64 (2.0) | 0.0001 | 43 (1.9) | 52 (2.3) | 0.004 |
| Large LDL particle size (% of Total) | 64 (3.3) | 87 (2.7) | 0.0001 | 47 (3.5) | 66 (4.1) | 0.0007 |
| HOMA | 5 (0.7) | 1.9 (0.9) | 0.01 | 8.6 (1.1) | 5.7 (1.9) | 0.1 |
| % with metabolic syndrome | 20 | 10 | 0.05 | 26 | 12 | 0.04 |

Data are expressed as mean (SE). OADIPOQH defined as ADIPOQ levels >1 SD above the mean for age-matched control subjects.

TABLE 12

CETP I405V genotype and lipoprotein characteristic and plasma CETP levels in families with exceptional longevity and controls.

|  | CETP I405V genotype | | | VV vs. II genotypes |
| --- | --- | --- | --- | --- |
| Variable | VV | IV | II | P value |
| HDL (mg/dL) | 57 (18) | 55 (16) | 55 (16) | 0.53 |
| Large HDL (% Total) | 56 (16) | 60 (14) | 60 (15) | 0.1 |
| HDL Size (nm) | 9.28 (0.56) | 9.09 (0.52) | 9.07 (0.48) | 0.02 |
| LDL (mg/dL) | 114 (35) | 120 (30) | 123 (34) | 0.16 |
| Large LDL (% Total) | 67 (25) | 58 (24) | 56 (28) | 0.02 |
| LDL Size (nm) | 21.29 (0.67) | 20.98 (0.63) | 20.88 (0.81) | 0.002 |
| CETP(μg/mL) | 1.65 (0.59) | 1.92 (0.65) | 1.99 (0.72) | 0.0008 |

Data are expressed as mean ± S.D.

TABLE 13

Comparison of lipoprotein traits in offspring and control groups by APOC3 C(−641)A genotype.

|  |  | Control APOC-3 | | | Offspring APOC-3 | | | CA/AA Control vs. Offspring |
| --- | --- | --- | --- | --- | --- | --- | --- | --- |
|  |  | CC | CA/AA | p | CC | CA/AA | p | p |
| Female | N | 11 | 64 |  | 26 | 70 |  |  |
|  | HDL size (nm) | 9.47 (0.09) | 9.27 (0.07) | 0.20 | 9.33 (0.07) | 9.43 (0.06) | 0.44 | 0.04 |
|  | HDL (mg/dl) | 77 (4) | 61 (2) | 0.007 | 72.7 (3.09) | 68.7 (1.9) | 0.27 | 0.009 |
|  | LDL size (nm) | 21.60 (0.11) | 21.11 (0.09) | 0.04 | 21.7 (0.05) | 21.6 (0.07) | 0.44 | 0.0006 |
|  | LDL (mg/dl) | 104 (9) | 132 (4) | 0.01 | 129 (7.98) | 118 (4.19) | 0.21 | 0.02 |
|  | Triglycerides (mg/dl) | 88 (12) | 115 (5) | 0.04 | 117 (12.1) | 114 (6.97) | 0.84 | 0.51 |
|  | Cholesterol (mg/dl) | 183 (13) | 208 (5) | 0.04 | 210 (9.63) | 196 (5.5) | 0.19 | 0.07 |
|  | TG/HDL | 1.21 (0.19) | 2.09 (0.13) | 0.007 | 1.73 (0.2) | 1.67 (0.12) | 0.81 | 0.01 |
|  | ApoA-1 (mg/dl) | 173 (6.41) | 175 (4.01) | 0.82 | 185 (5.71) | 173 (2.87) | 0.08 | 0.76 |
|  | ApoB (mg/dl) | 102 (9.06) | 102 (3.27) | 0.96 | 105 (5.07) | 104 (2.01) | 0.85 | 0.71 |
|  | APOC3 (mg/dl) | 8.9 (1.6) | 10.97 (0.65) | 0.05 | 9.4 (1.3) | 11 (0.6) | 0.14 | 0.9 |
|  | CETP levels (mg/dl) | 1.84 (0.2) | 2.14 (0.09) | 0.2 | 1.9 (0.1) | 2.08 (0.07) | 0.22 | 0.8 |
| Male | N | 9 | 46 |  | 22 | 48 |  |  |
|  | HDL size (nm) | 8.90 (0.13) | 9.02 (0.06) | 0.33 | 9.03 (0.09) | 9.16 (0.06) | 0.35 | 0.1 |
|  | HDL (mg/dl) | 50 (5) | 45 (1) | 0.21 | 51 (3) | 55 (2) | 0.33 | 0.0005 |
|  | LDL (mg/dl) | 103 (11) | 107 (4) | 0.67 | 106 (6) | 101 (4) | 0.54 | 0.04 |
|  | LDL size (nm) | 21.00 (0.18) | 20.80 (0.08) | 0.44 | 21 (0.18) | 21.2 (0.1) | 0.27 | 0.09 |
|  | Triglycerides (mg/dl) | 104 (10) | 111 (5) | 0.56 | 149 (15) | 113 (10) | 0.05 | 0.54 |
|  | Cholesterol (mg/dl) | 165 (15) | 170 (5) | 0.68 | 172 (8) | 166 (6) | 0.57 | 0.24 |

TABLE 13-continued

Comparison of lipoprotein traits in offspring and control groups by APOC3 C(−641)A genotype.

|  | Control APOC-3 | | | Offspring APOC-3 | | | CA/AA Control vs. Offspring |
|---|---|---|---|---|---|---|---|
|  | CC | CA/AA | p | CC | CA/AA | p | p |
| TG/HDL | 2.24 (0.29) | 2.65 (0.18) | 0.32 | 3.41 (0.43) | 2.19 (0.21) | 0.02 | 0.07 |
| ApoA-1 (mg/dl) | 143 (11) | 136 (4.12) | 0.58 | 158 (5.36) | 140 (2.77) | 0.006 | 0.32 |
| ApoB (mg/dl) | 85.4 (9.61) | 93.7 (2.92) | 0.34 | 101 (3.37) | 96.4 (2.01) | 0.3 | 0.52 |
| APOC3 (mg/dl) | 7.3 (1.6) | 10.2 (0.9) | 0.05 | 8.6 (1.5) | 10.3 (0.76) | 0.25 | 0.85 |
| CETP levels (mg/dl) | 1.49 (0.34) | 1.76 (0.1) | 0.37 | 1.71 (0.12) | 1.9 (0.07) | 0.2 | 0.5 |

CC: homozygous for −641 C; CA/AA: homozygous and heterozygous for (−641) A. Results presented as mean (SE).

REFERENCES

1. Barzilai N, Shuldiner A R. Searching for human longevity genes: The future history of gerontology in the post-genomic era. Journal of Gerontology. 56A:M83-M87, 2001.
2. Perls T T, Bubrick E, Wager C G, Vijg J, Kruglyak L. Sibling of centenarians live longer. Lancet. 351:1560, 1998.
3. Puca A A, Daly M J, Brewster S J, Matise T C, Barrett J, Shea-Drinkwater M, et al. A genome-wide scan for linkage to human exceptional longevity identifies a locus on chromosome 4. Proc Natl Acad Sci USA. 98:10505-8, 2001.
4. Atzmon G, Schechter C, Greiner W, Davidson D, Rennert G, Barzilai N. Clinical Phenotype of Families with Longevity. J Am Geriat Soc 52(2):274-277, 2004.
5. Evert J, Lawler E, Perls T: Morbidity Profiles of Centenarians: Survivors, Delayers and Escapers. J. Gerontol. A. Biol. Sci. Med. Sci. 58(3): 232-7, 2003.
6. Perls T T, Wilmoth J, Levenson R, Drinkwater M, Cohen M, Bogan H, et al. Life-long sustained mortality advantage of siblings of centenarians. Proc Natl Acad Sci U S A. 2002; 99(12):8442-7.
7. Barzilai N, Gabriely I, Gabriely M, Iankowitz N, Sorkin J D. Offspring of centenarians have a favorable lipid profile. J Am Geriatr Soc. 2001; 49: 76-9.
8. Ferrara A, Barrett-Connor E, Shan J. Total, LDL, and HDL cholesterol decrease with age in older men and women. The Rancho Bernardo Study 1984-1994. Circulation. 1997 Jul. 1; 96(1):37-43.
9. Wilson, P. W., K. M. Anderson, et al. (1994). Determinants of change in total cholesterol and HDL-C with age: the Framingham Study. J Gerontol 49(6): M252-7.
10. U.S. Department of Health and Human Services (DHHS). National Center for Health Statistics. Third National Health and Nutrition Survey, 1988-1994, NHANES III Second Laboratory Data File (CD-ROM series 11, No. 2A).
11. Malaguarnera M, Giugno I, Ruello P, Rizzo M, Panebianco M P, Pistone G, Tomasello F B. Lipid profile variations in a group of healthy elderly and centenarians. Eur Rev Med Pharmacol Sci. 1998 March-April; 2(2):75-9.
12. Pepe, G., V. Di Perna, et al. (1998). In search of a biological pattern for human longevity: impact of apo A-IV genetic polymorphisms on lipoproteins and the hyper-Lp (a) in centenarians. Atherosclerosis 137(2): 407-17.
13. Thillet J, Doucet C, Chapman J, Herbeth B, Cohen D, Faure-Delanef L. Elevated lipoprotein(a) levels and small apo(a) isoforms are compatible with longevity: evidence from a large population of French centenarians. Atherosclerosis. 1998 February; 136(2):389-94.
14. Atzmon G, Gabriely I, Greiner W, Davidson D, Barzilai N: Plasma HDL Levels Highly Correlate with Cognitive Function in Exceptional Longevity. J Gerontol A Biol Sci Med. Sci. 2002. 57:M712-5.
15. Lancaster, J. M., M. E. Carney, et al. (1997). BRCA 1 and 2—A Genetic Link to Familial Breast and Ovarian Cancer." Medscape Womens Health 2(2): 7.
16. Verghese J, Lipton R B, Hall C B, Kuslansky G, Katz M J, Buschke H. Abnormality of gait as a predictor of non-Alzheimer's dementia. N Engl J Med 2002; 347(22): 1761-8.
17. Folstein M F, Folstein S E, McHugh P R. "Mini-mental state" A practical method for grading the cognitive state of patients for the clinician. J. Psychiatr. Res. 1975; 12:189-198.
18. Otvos J D, Jeyarajah E J, Bennett D W. Quantification of plasma lipoproteins by proton nuclear magnetic resonance spectroscopy. Clin Chem. 37(3):377-86, 1991.
19. Otvos J D, Jeyarajah E J, Bennett D W, Krauss R M. Development of a proton nuclear magnetic resonance spectroscopic method for determining plasma lipoprotein concentrations and subspecies distributions from a single, rapid measurement. Clin Chem. 1992 September; 38(9): 1632-8.
20. Kraus W E, Houmard J A, Duscha B D, Knetzger K J, Wharton M B, McCartney J S, Bales C W, Henes S, Samsa G P, Otvos J D, Kulkarni K R, Slentz C A. Effects of the amount and intensity of exercise on plasma lipoproteins. N Engl J. Med. 2002 Nov. 7; 347(19): 1483-92.
21. Lamarche B, Tchernof A, Moorjani S, Cantin B, Dagenais G R, et al. 1997. Small, dense low-density lipoprotein particles as a predictor of the risk of ischemic heart disease in men. Prospective results from the Quebec Cardiovascular Study. Circulation 95:69-75.
22. Austin M A. Triglyceride, small, dense low-density lipoprotein, and the atherogenic lipoprotein phenotype. Curr Atheroscler Rep. 2000 May; 2(3):200-7. Review.
23. Kamigaki A S, Siscovick D S, Schwartz S M, Psaty B M, Edwards K L, Raghunathan T E, Austin M A. Low density lipoprotein particle size and risk of early-onset myocardial infarction in women. Am J. Epidemiol. 2001 May 15; 153(10):939-45.
24. Bjornheden T, Babyi A, Bondjers G, Wiklund O. 1996. Accumulation of lipoprotein fractions and subfractions in the arterial wall, determined in an in vitro perfusion system. Atherosclerosis 123:43-56
25. Anber V, Millar J S, McConnell M, Shepherd J, Packard C J. 1997. Interaction of very-low-density, intermediate-density, and low-density lipoproteins with human arterial wall proteoglycans. Arterioscler. Thromb. Vasc. Biol. 17:2507-14

26. Chait A, Brazg R L, Tribble D L, Krauss R M. 1993. Susceptibility of small, dense, low-density lipoproteins to oxidative modification in subjects with the atherogenic lipoprotein, pattern B. Am. J. Med. 94:350-56.
27. Liu M L, Ylitalo K, Vakkilainen J, Nuotio I, Valkonen M, Lahdenpera S, Viikari J, Taskinen M R. Susceptibility of LDL to oxidation in vitro and antioxidant capacity in familial combined hyperlipidemia: comparison of patients with different lipid phenotypes. Ann Med. 2002; 34(1):48-54.
28. Vakkilainen J, Makimattila S, Seppala-Lindroos A, Vehkavaara S, Lahdenpera S, Groop P H, Taskinen M R, Yki-Jarvinen H. Endothelial dysfunction in men with small LDL particles. Circulation. 2000 Aug. 15; 102(7):716-21.
29. Superko H R. Small, dense low-density lipoprotein subclass pattern B: issues for the clinician. Curr Atheroscler Rep. 1999 July; 1(1):50-7. Review.
30. Campos H, Blijlevens E, McNamara J P, Ordovas J M, Posner B M, et al. 1992. LDL particle size distribution. Results from the Framingham Offspring Study. Arteriosclerosis. Thromb. 12:1410-19.
31. Asztalos B F, Horvath K V, McNamara J R, Rohein P S, Rubinstein J J, Schaefer E J. Effects of atorvastatin on the HDL subpopulation profile of coronary heart disease patients. J Lipid Res. 2002 October; 43(10):1701-7.
32. Pascot A, Lemieux I, Bergeron J, Tremblay A, Nadeau A, Prud'homme D, Couillard C, Lamarche B, Despres J P. HDL particle size: a marker of the gender difference in the metabolic risk profile. Atherosclerosis. 2002 February; 160(2):399-406.
33. Barzilai, N. and G. Gupta (1999). Revisiting the role of fat mass in the life extension induced by caloric restriction. J Gerontol A Biol Sci Med Sci 54(3): B89-96; discussion B97-8.
34. Calabresi, L, G. Francéschini, C. R. Sirtori, A. De Palma, M. Saresella, P. Ferrante and D. Taramelli Inhibition of VCAM-1 expression in endothelial cells by reconstituted high density lipoproteins. Biochem. Biophys. Res. Commun. 238 (1997), pp. 61-6.
35. Nofer, J. R. M. Walter, B. Kehrel, S. Wierwille, M. Tepel, U. Seedorf and G. Assmann, HDL3-mediated inhibition of thrombin-induced platelet aggregation and fibrinogen binding occurs via decreased production of phosphoinositide-derived second messengers 1,2-diacylglycerol and inositol 1,4,5-tris-phosphate. Arterioscler. Thromb. Vasc. Biol. 18 (1998), pp. 861-869.
36. Witztum J. L. and J. A. Berliner, Oxidized phospholipids and isoprostanes in atherosclerosis. Curr. Opin. Lipidol. 9 (1998), pp 441-448.
37. Lesnik, P, A. Vonica, M. Guerin, M. Moreau and M. J. Chapman, Anti-coagulant activity of tissue factor pathway inhibitor in human plasma is preferentially associated with dense subspecies of LDL and HDL and with Lp(a). Arterioscl. Thromb. 13 (1993), pp. 1066-107.
38. Levin, E. G. L. A. Miles, G. M. Fless, A. M. Scanu, P. Baynham, L. K. Curtiss and E. F. Plow, Lipoproteins inhibit the secretion of tissue plasminogen activator from human endothelial cells. Arterioscler. Thromb. 14 (1994), pp. 438-44.
39. Libby P. Managing the risk of atherosclerosis: the role of high-density lipoprotein. Am J. Cardiol. 2001 20; 88(12A): 3N-8N. Review.
40. Rader D J, Maugeais C. Genes influencing HDL metabolism: new perspectives and implications for atherosclerosis prevention. Mol Med. Today. 2000 April; 6(4):170-5. Review.
41. Merched A, Xia Y, Visvikis S, Serot J M, Siest G. Decreased high-density lipoprotein cholesterol and serum apolipoprotein A-1 concentrations are highly correlated with the severity of Alzheimer's disease. *Neurobiology of Aging.* 2000; 21:27-30
42. Kawano M, Kawakami M, Otsuka M, Yashima H, Yaginuma T, Ueki A. Marked decrease of plasma apolipoprotein A-I and A-II in Japanese patients with late-onset non-familial Alzheimer's disease. Clin Chim Acta. 1995; 239: 209-211.
43. Kuriyama M, Takahashi K, Yamono T, Hokezu Y, Togo S, Osame M, Igakura T. Low levels of serum apolipoprotein a1 and a2 in senile dementia. *Jpn. J Psychiatry Neurol.* 1994; 48:589-5938.
44. van Exel E, de Craen A J, Gussekloo J, Houx P, Bootsma-van der Wiel A, Macfarlane P W, Blauw G J, Westendorp R G. Association between high-density lipoprotein and cognitive impairment in the oldest old. Ann Neurol. 2002 June; 51(6):716-21.
45. Yamashita, S., D. L. Sprecher, N. Sakai, Y. Matsuzawa, S. Tarui, and D. Y. Hui. 1990. Accumulation of apolipoprotein E-rich high density lipoproteins in hyperalphalipoproteinemic human subjects with plasma cholesteryl ester transfer protein deficiency. J. Clin. Invest. 86: 688-695.
46. Arai, T., T. Tsukada, T. Murase, and K. Matsumoto. 2000. Particle size analysis of high density lipoproteins in patients with genetic cholesteryl ester transfer protein deficiency. Clin. Chim. Acta. 301: 103-117.
47. Sakai N, Yamashita S, Hirano K, Ishigami M, Arai T, et al.1995. Decreased affinity of low density lipoprotein (LDL) particles for LDL receptors in patients with cholesteryl ester transfer protein deficiency. Eur. J. Clin. Invest. 25:332-39.
48. Zak Z, Lagrost L, Gautier T, Masson D, Deckert V, Duverneuil L, De Barros J P, Le Guern N, Dumont L, Schneider M, Risson V, Moulin P, Autran D, Brooker G, Sassard J, Bataillard A. Expression of simian CETP in normolipidemic Fisher rats has a profound effect on large sized apoE-containing HDL. J Lipid Res. 2002 December; 43(12):2164-2171.
49. Ikewaki K, Nishiwaki M, Sakamoto T, Ishikawa T, Fairwell T, et al. 1995. Increased catabolic rate of low density lipoproteins in humans with cholesteryl ester transfer protein deficiency. J. Clin. Invest. 96:1573-81.
50. Carr M C, Ayyobi A F, Murdoch S J, Deeb S S, Brunzell J D. Contribution of hepatic lipase, lipoprotein lipase, and cholesteryl ester transfer protein to LDL and HDL heterogeneity in healthy women. Arterioscler Thromb Vasc Biol. 2002 Apr. 1; 22(4):667-73.
51. Juo S H, Han Z, Smith J D, Colangelo L, Liu K. Promoter polymorphisms of hepatic lipase gene influence HDL(2) but not HDL(3) in African American men: CARDIA study. J Lipid Res. 2001 February; 42(2):258-64.
52. Zambon, A., S. S. Deeb, J. E. Hokanson, B. G. Brown, and J. D. Brunzell. 1998. Common variants in the promoter of the hepatic lipase gene are associated with lower levels of hepatic lipase activity, buoyant LDL, and higher HDL2 cholesterol. Arterioscler. Thromb. Vasc. Biol. 18: 1723-1729.
53. Agerholm-Larsen B, Nordestgaard B G, Steffensen R, Jensen G, Tybjaerg-Hansen A. Elevated HDL cholesterol is a risk factor for ischemic heart disease in white women when caused by a common mutation in the cholesteryl ester transfer protein gene. Circulation. 2000 Apr. 25; 101 (16): 1907-12.
54. Brousseau M E, O'Connor J J Jr, Ordovas J M, Collins D, Otvos J D, Massov T, McNamara J R, Rubins H B, Robins S J, Schaefer E J. Cholesteryl ester transfer protein Taq1 B2B2 genotype is associated with higher HDL cholesterol levels and lower risk of coronary heart disease end points in men with HDL deficiency: Veterans Affairs HDL Cholesterol Intervention Trial. Arterioscler Thromb Vasc Biol. 2002 Jul. 1; 22(7):1148-54.

55. Kuivenhoven J A, de Knijff P, Boer J M, Smalheer H A, Botma G J, et al. 1997. Heterogeneity at the CETP gene locus. Influence on plasma CETP concentrations and HDL cholesterol levels. Arterioscler. Thromb. Vasc. Biol. 17:560-68.

56. Wilund K R, Ferrell R E, Phares D A, Goldberg A P, Hagberg J M. Changes in high-density lipoprotein-cholesterol subfractions with exercise training may be dependent on cholesteryl ester transfer protein (CETP) genotype. Metabolism. 2002 June; 51(6):774-8.

57. Schaefer E J, Lamon-Fava S, Cohn S D, Schaefer M M, Ordovas J M, Castelli W P, Wilson P W. Effects of age, gender, and menopausal status on plasma low density lipoprotein cholesterol and apolipoprotein B levels in the Framingham Offspring Study. J Lipid Res. 1994 May; 35(5):779-92.

58. Koren-Morag N, Tanne D, Graff E, Goldbourt U. Related Articles, Low- and high-density lipoprotein cholesterol and ischemic cerebrovascular disease: the bezafibrate infarction prevention registry. Arch Intern Med. 2002 13; 162(9):993-9

59. MRC/BHF Heart Protection Study of cholesterol lowering with simvastatin in 20,536 high-risk individuals: a randomised placebo-controlled trial. Lancet 2002 Jul. 6; 360(9326):7-22.

60. Nissen, H., A. B. Hansen, et al. (1994). Detection of a single base deletion in codon 424 of the low density lipoprotein receptor gene in a Danish family with familial hypercholesterolemia. Atherosclerosis 111(2): 209-15.

61. Descamps, O., J. C. Hondekijn, et al. (1997). High prevalence of a novel mutation in the exon 4 of the low-density lipoprotein receptor gene causing familial hypercholesterolemia in Belgium Clin Genet 51(5): 303-8.

62. Diaz, M. N. B. Frei, J. A. Vita and J. F. Keaney, Antioxidants and atherosclerotic heart disease. N. Engl. J. Med. 337 (1997), pp. 408-416.

63. Austin M A, King M C, Vranizan K M, Newman B, Krauss R M. 1988. Inheritance of low-density lipoprotein subclass patterns: results of complex segregation analysis. Am. J. Hum. Genet. 43:838-46.

64. Coresh J, Kwiterovich P O Jr, Smith H H, Bachorik P S. 1993. Association of plasma triglyceride concentration and LDL particle diameter, density, and chemical composition with premature coronary artery disease in men and women. J. Lipid Res. 34:1687-97.

65. Gardner C D, Fortmann S P, Krauss R M. 1996. Association of small low-density lipoprotein particles with the incidence of coronary artery disease in men and women. JAMA 276:875-8.

66. Stampfer M J, Krauss R M, Ma J, Blanche P J, Holl L G, et al. 1996. A prospective study of triglyceride level, low-density lipoprotein particle diameter, and risk of myocardial infarction. JAMA 276:882-88.

67. Blake G J, Otvos J D, Rifai N, Ridker P M. Low-density lipoprotein particle concentration and size as determined by nuclear magnetic resonance spectroscopy as predictors of cardiovascular disease in women. Circulation. 2002 Oct. 8; 106(15): 1930-7.

68. Tangney C C, Mosca L J, Otvos J D, Rosenson R S. Oral 17beta-estradiol and medroxyprogesterone acetate therapy in postmenopausal women increases HDL particle size. Atherosclerosis. 2001 April; 155(2):425-30.

69. Melenovsky V, Malik J, Wichterle D, Simek J, Pisarikova A, Skrha J, Poledne R, Stavek P, Ceska R. X Comparison of the effects of atorvastatin or fenofibrate on nonlipid biochemical risk factors and the LDL particle size in subjects with combined hyperlipidemia. Am J Cardiol. 2002 Oct. 17; 90(8A):22i-29i.

70. Bruce C, Sharp D S, Tall A R. Relationship of HDL and coronary heart disease to a common amino acid polymorphism in the cholesteryl ester transfer protein in men with and without hypertriglyceridemia. J Lipid Res. 1998 May; 39(5):1071-8.

71. Tailleux A and Fruchart J C. HDL heterogeneity and atherosclerosis. Critical Reviews in Clinical Laboratory Sciences. 33(3) 163-201: 1996.

72. Barbagallo C M, Averna M R, Fradà G, Noto D, Cavera G, and Notarbartolo A. Lipoprotein profile and high-density lipoproteins: subfractions distributions in centenarians. Gerontology 44: 106-110, 1998.

73. Arai Y, Hirose N, Kawamura M, Homma S, Hasegawa H, Ishida H, Osono Y, Shimizu K, Nakamura Y, Sakamoto T, Tada N and Homma A. Lipid and lipoprotein profile of Japanese centenarians—high prevalence of hypo beta lipoproteinemia. Nippon Ronen Igakkai Zasshi. 34(3): 202-8, 1997 [article in Japanese].

74. Ettinger W H Jr, Verdery R B, Wahl P W, Fried L P. High density lipoprotein subfractions in older people. J. Gerontol. 49(3): M116-22, 1994.

75. Cheng, S., Grow, M., Pallaud, C., Klitz, W., Erlich, H., Visvikis, S., Chen, J., Pullinger, C., Malloy, M., Siest, G., Kane, J. (1999) A multilocus genotyping assay for candidate markers of cardiovascular disease risk. Genome Research 9: 936-949.

76. LipoScience—Clinicians—Research Services—Domestic, http://www.liposcience.com/clin_rs.htm (as available on Jan. 14, 2003).

77. Handbook of Lipoprotein Testing, Chapter 31: Measurement of lipoprotein subclass profiles by nuclear magnetic resonance spectroscopy, J. D. Otvos, AACC Press, Washington D.C., 2000, 2nd edition, pp 609-623.

78. LipoScience—Clinicians—NMR LipoProfile—Test Information, http://www.liposcience.com/clin_nmr.htm (as available on Jan. 14, 2003).

79. von Eckardstein, A. Y. Huang and G. Assmann, Physiological role and clinical relevance of high-density lipoprotein subclasses. Curr. Opin. Lipidol. 5 (1994), pp. 404-416.

80. Austin M A, King M C, Vranizan K M, Krauss R M. 1990. Atherogenic lipoprotein phenotype. A proposed genetic marker for coronary heart disease risk. Circulation 82:495-506.

81. Krauss R M. Dietary and genetic effects on low-density lipoprotein heterogeneity. Annu Rev Nutr. 2001; 21:283-95. Review 82. Sugano, M., N. Makino, S. Sawada, S. Otsuka, M. Watanabe, H. Okamoto, M. Kamada, and A. Mizushima. 1998. Effect of antisense oligonucleotides against cholesteryl ester transfer protein on the development of atherosclerosis in cholesterol-fed rabbits. J. Biol. Chem. 273: 5033-5036.

83. Okamoto, H., F. Yonemori, K. Wakitani, T. Minowa, K. Maeda, and H. Shinkai. 2000. A cholesteryl ester transfer protein inhibitor attenuates atherosclerosis in rabbits. Nature. 406: 203-207.

84. Hirano, K., S. Yamashita, and Y. Matsuzawa. 2000. Pros and cons of inhibiting cholesteryl ester transfer protein. Curr. Opin. Lipidol. 11: 589-596.

85. Francone O L, Royer L, Haghpass M. 1996. Increased prebeta-HDL levels, cholesterol efflux, and LCAT-mediated esterification in mice expressing the human cholesteryl ester transfer protein (CETP) and human apolipoprotein A-I (apoA-I) transgenes. J. Lipid Res. 37:1268-77.
86. Funke H, Wiebusch H, Fuer L, Muntoni S, Schulte H, Assmann G. Identification of mutations in the cholesterol ester transfer protein in Europeans with elevated high density lipoprotein cholesterol. Circulation. 1994; 90(pt 2):1-241. Abstract.
87. Zhong S, Sharp D S, Grove J S, Bruce C, Yano K, et al. 1996. Increased coronary heart disease in Japanese-American men with mutation in the cholesteryl ester transfer protein gene despite increased HDL levels. J. Clin. Invest. 97:2917-23.
88. Calle E E, Thun M J, Petrelli J M, Rodriguez C, Heath C W, Jr. Body-mass index and mortality in a prospective cohort of U.S. adults. *N Engl J Med* 1999; 341: 1097-105.
89. Agellon L B et al. Organization of the human cholesteryl ester transfer protein gene. Biochemistry 29: 1372-6, 1990.
90. Drayna D et al. Cloning and sequencing of human cholesteryl ester transfer protein cDNA. Nature 327 (6123): 632-4, 1987.
91. Lusis A J et al. Assignment of the human gene for human cholesteryl ester transfer protein to chromosome 16q12-16q21. Genomics 1: 232-5, 1987.
92. U.S. Pat. No. 6,313,142 B1, issued Nov. 6, 2001, Damon et al.
93. U.S. Pat. No. 6,197,786 B1, issued Mar. 6, 2001, DeNinno et al.
94. U.S. Patent Application Publication No. US2002/0177716 A1, published Nov. 28, 2002, Damon et al., issued as U.S. Pat. No. 6,689,897 B2, Feb. 10, 2004.
95. U.S. Patent Application Publication No. US2002/0042364 A1, published Apr. 11, 2002, Rittershaus et al.
96. Sun S. Technology evaluation: SELEX, Gilead Sciences Inc. Curr. Opin. Mol. Ther. 2: 100-5, 2000.
97. Ashrafi K et al. Genome-wide RNAi analysis of *Caenorhabditis elegans* fat regulation genes. Nature 421 (6920): 268-72, 2003.
98. Hesler C B et al. Monoclonal antibodies to the Mr 74,000 cholesteryl ester transfer protein neutralize all of the cholesteryl ester and triglyceride transfer activities in human plasma. J Biol Chem. 1988 Apr. 15; 263(11):5020-3.
99. Yen Ft et al. Inhibition of cholesteryl ester transfer protein activity by monoclonal antibody. Effects on cholesteryl ester formation and neutral lipid mass transfer in human plasma. J Clin Invest. 1989 June; 83(6):2018-24.
100. Wang S et al. Identification of a sequence within the C-terminal 26 amino acids of cholesteryl ester transfer protein responsible for binding a neutralizing monoclonal antibody and necessary for neutral lipid transfer activity. J Biol Chem. 1992 Sep. 5; 267(25): 17487-90.
101. Williams S et al. Sequencing of the cholesteryl ester transfer protein 5' regulatory region using artificial transposons. Gene 197: 101-107, 1997.
102: Klerkx A. H. E. M. et al. Haplotype analysis of the CETP gene: not Taq1B but the closely linked -629C→A polymorphism and a novel promoter variant are independently associated with CETP concentration. Human Molecular Genetics 12(2): 111-123, 2003.
103. Fumeron F et al. Alcohol intake modulates the effect of a polymorphism of the cholesteryl ester transfer protein gene on plasma high density lipoprotein and the risk of myocardial infarction. J. Clin. Invest. 96(3): 1664-71, 1995.
104. Corbex M et al. Extensive association analysis between the CETP gene and coronary heart disease phenotypes reveals several putative functional polymorphisms and gene-environment interaction. Genet. Epidemiol. 19: 64-80, 2000.
105. Kuivenhoven J A et al. The role of a common variant of the cholesteryl ester transfer protein gene in the progression of coronary atherosclerosis. The Regression Growth Evaluation Statin Study Group. New Engl. J. Med. 338:86-93, 1998.
106. Bernard S et al. Association between plasma HDL-cholesterol concentration and Taq1B CETP gene polymorphism in non-insulin-dependent diabetes mellitus. J. Lipid Res. 39: 59-65, 1998.
107. Ordovas J M et al. Association of cholesteryl ester transfer protein-Taq1B polymorphism with variation in lipoprotein subclasses and coronary heart disease risk. The Framingham Study. Arterioscler. Thromb. Vasc. Biol. 20: 1323-9, 2000.
108. Dachet C. New functional promoter polymorphism, CETP/-629, in cholesteryl ester transfer protein (CETP) gene related to CETP mass and high density lipoprotein cholesterol levels. Role of Sp1/Sp3 in transcriptional regulation. Arterioscler. Thromb. Vasc. Biol. 20: 507-515, 2000.
109. Couture P, Otvos J D, Cupples A, et al. Association of the C-514T polymorphism in the hepatic lipase gene with variations in lipoprotein subclass profiles: The Framingham Offspring Study. Arterioscler Thromb Vasc Biol 2000; 20:815-822.
110. Grundy S M, Vega G L, Otvos J D, Rainwater D L, Cohen J C. Hepatic lipase influences high density lipoprotein subclass distribution in normotriglyceridemic men: genetic and pharmacological evidence. J Lipid Res 1999; 40:229-234.
111. Runsey S C, Galeano N F, Arad Y, Deckelbaum R J. Cryopreservation with sucrose maintains normal physical and biological properties of human plasma low density lipoproteins. J Lipid Res 1992; 33:1551-61.
112. Falconer, D S, and Mackay T F C. Introduction to Quantitative Genetics. Essex, UK: Addison Wesley Longman, 1996.
113. Executive Summary of The Third Report of The National Cholesterol Education Program (NCEP) Expert Panel on Detection, Evaluation, And Treatment of High Blood Cholesterol In Adults (Adult Treatment Panel III) JAMA 2001; 16:285:2486-97.
114. Lakka H M, et al. The metabolic syndrome and total and cardiovascular disease mortality in middle-aged men. JAMA. 2002; 288:2709-2716.
115. Reaven G M. Role of insulin resistance in human disease (Banting lecture). Diabetes. 1988; 37:1595-1607.
116. Garvey W T, et al. Effects of insulin resistance and type 2 diabetes on lipoprotein subclass particle size and concentration determined by nuclear magnetic resonance. Diabetes. 2003; 52:453-462.
117. Nieves D J, Cnop M, Retzlaff B, Walden C E, Brunzell J D, Knopp R H, Kahn S E. The atherogenic lipoprotein profile associated with obesity and insulin resistance is largely attributable to intra-abdominal fat. Diabetes. 2003 January; 52(1):172-9.
118. DeFronzo R A. Insulin resistance: a multifaceted syndrome responsible for NIDDM, obesity, hypertension, dyslipidaemia and atherosclerosis. Neth J Med 1997; 50:191-7.

119. Despres J P, Lamarche B, Mauriege P, et al. Hyperinsulinemia as an independent risk factor for ischemic heart disease. N Engl J Med. 1996; 334:952-7.
120. Copeland G P, Leinster S J D, J. C., Hipkin L J. Insulin resistance in patients with colorectal cancer. Br J Surg. 1987; 74:1031-5.
121. Facchini F S, Hua N, Abbasi F, Reaven G M. Insulin resistance as a predictor of age-related diseases. J Clin Endocrinol Metab. 2001 August; 86(8):3574-8.
122. Stoll B A. Western nutrition and the insulin resistance syndrome: a link to breast cancer. Eur J Clin Nutr. 1999; 53:83-7.
123. Chow W-H, Gridley G, Fraumeni J F, Jarvholm B. Obesity, hypertension, and the risk of kidney cancer in men. N Engl J. Med. 2000; 343:1305-11.
124. Jong M C, Rensen P C, Dahlmans V E, van der Boom H, van Berkel T J, Havekes L M. Apolipoprotein C-III deficiency accelerates triglyceride hydrolysis by lipoprotein lipase in wild-type and apoE knockout mice. J Lipid Res. 2001 October; 42(10):1578-85.
125. Chhabra S, Narang R, Krishnan L R, Vasisht S, Agarwal D P, Srivastava L M, Manchanda S C, Das N. Apolipoprotein C3 SstI polymorphism and triglyceride levels in Asian Indians. BMC Genet. 2002 Jun. 6; 3(1):9. Epub 2002 Jun. 6.
126. Minihane A M, Finnegan Y E, Talmud P, Leigh-Firbank E C, Williams C M. Influence of the APOC3-2854T>G polymorphism on plasma lipid levels: effect of age and gender. Biochim Biophys Acta. 2002 Aug. 8; 1583(3):311-4.
127. Waterworth D M, Talmud P J, Luan J, Flavell D M, Byrne C D, Humphries S E, Wareham N J. Variants in the APOC3 promoter insulin responsive element modulate insulin secretion and lipids in middle-aged men. Biochim Biophys Acta. 2003 Apr. 17; 1637(3):200-6.
128. Dammerman M, Sandkuijl L A, Halaas J L, Chung W, Breslow J L. An apolipoprotein CIII haplotype protective against hypertriglyceridemia is specified by promoter and 3' untranslated region polymorphisms. Proc Natl Acad Sci USA. 1993 May 15; 90(10):4562-6.
129. Hegele R A, Connelly P W, Hanley A J, Sun F, Harris S B, Zinman B. Common genomic variation in the APOC3 promoter associated with variation in plasma lipoproteins. Arterioscler Thromb Vasc Biol. 1997 November; 17(11): 2753-8.
130. Anisimov S V, Volkova M V, Lenskaya L V, Khavinson V K, Solovieva D V, Schwartz E I. Age-associated accumulation of the apolipoprotein C-III gene T-455C polymorphism C allele in a Russian population. J Gerontol A Biol Sci Med Sci. 2001 January; 56(1):B27-32.
131. Breyer E D, Le N A, Li X, Martinson D, Brown W V. Apolipoprotein C-III displacement of apolipoprotein E from VLDL: effect of particle size. J Lipid Res. 1999 October; 40(10): 1875-82.
132. Holzenberger, M., Dupont, J., Ducos, B., Leneuve, P., Géloën, A., Evens, P., Cervera, P., Le Bouc, Y., 2003. IGF-1 receptor regulates lifespan and resistance to oxidative stress in mice. Nature 421, 182-187.
133. Krassas G E, Pontikides N, Kaltsas T, Dumas A, Frystyk J, Chen J W, Flyvbjerg A: Free and total insulin-like growth factor (IGF)-I, -II and IGF binding protein-1, -2, and -3 serum levels in patients with active thyroid eye disease. J. Clin. Endocrinol. Metab. 88:132-135, 2003.
134. Juul A, Scheike T, Davidsen M, Gyllenborg J, Jorgensen T. Low serum insulin-like growth factor I is associated with increased risk of ischemic heart disease: a population-based case-control study. Circulation. 2002 Aug. 20; 106 (8):939-44.
135. Gamero P, Sornay-Rendu E, Delmas P D. Low serum IGF-1 and occurrence of osteoporotic fractures in postmenopausal women. Lancet. 2000 Mar. 11; 355(9207): 898-9.
136. Harman S M, Metter E J, Blackman M R, Landis P K, Carter H B; Baltimore Longitudinal Study on Aging. Serum levels of insulin-like growth factor I (IGF-1), IGF-II, IGF-binding protein-3, and prostate-specific antigen as predictors of clinical prostate cancer. J Clin Endocrinol Metab. 2000 November; 85(11):4258-65.
137. Stattin P, Bylund A, Rinaldi S, Biessy C, Dechaud H, Stenman U H, Egevad L, Riboli E, Hallmans G, Kaaks R. Plasma insulin-like growth factor-1, insulin-like growth factor-binding proteins, and prostate cancer risk: a prospective study. J Natl Cancer Inst. 2000 Dec. 6; 92(23): 1910-7.
138. Toniolo P, Bruning P F, Akhmedkhanov A, Bonfrer J M, Koenig K L, Lukanova A, Shore R E, Zeleniuch-Jacquotte A. Serum insulin-like growth factor-1 and breast cancer. Int J Cancer. 2000 Dec. 1; 88(5):828-32.
139. Giovannucci E, Pollak M, Platz E A, Willett W C, Stampfer M J, Majeed N, Colditz G A, Speizer F E, Hankinson S E. Insulin-like growth factor I (IGF-1), IGF-binding protein-3 and the risk of colorectal adenoma and cancer in the Nurses' Health Study. Growth Horm IGF Res. 2000 April; 10 Suppl A:S30-1.
140. Chan J M, Stampfer M J, Ma J, Gann P, Gaziano J M, Pollak M, Giovannucci E. Insulin-like growth factor-1 (IGF-1) and IGF binding protein-3 as predictors of advanced-stage prostate cancer. J Natl Cancer Inst. 2002 Jul. 17; 94(14): 1099-106.
141. Hankinson S E, Willett W C, Colditz G A, Hunter D J, Michaud D S, Deroo B, Rosner B, Speizer F E, Pollak M. Circulating concentrations of insulin-like growth factor-1 and risk of breast cancer. Lancet. 1998 May 9; 351(9113): 1393-6.
142. Zhao H, Grossman H B, Spitz M R, Lerner S P, Zhang K, Wu X. Plasma levels of insulin-like growth factor-1 and binding protein-3, and their association with bladder cancer risk. J Urol. 2003 February; 169(2):714-7.
143. Sandhu M S, Heald A H, Gibson J M, Cruickshank J K, Dunger D B, Wareham N J. Circulating concentrations of insulin-like growth factor-I and development of glucose intolerance: a prospective observational study. Lancet. 2002 359(9319):1740-5.
144. Longo, V., Finch, C., 2003. Evolutionary medicine: from dwarf model systems to healthy centenarians? Science 299, 1342-1345.
145. Pajvani U B, Scherer P E. Adiponectin: systemic contributor to insulin sensitivity. Curr Diab Rep. 2003 June; 3(3):207-13. Review.
146. Diez J J, Iglesias P. The role of the novel adipocyte-derived hormone adiponectin in human disease. Eur J Endocrinol. 2003 March; 148(3):293-300. Review.
147. Kenyon, C., 2001. A conserved regulatory system for aging. Cell 105, 165-168.
148. Khosravi M J, Diamandi A, Mistry J, Lee P D K: A non-competitive ELISA for serum insulin-like growth factor-I. Clin Chem 42: 1147-1154, 1996.
149. Lee P D K, Powell D, Baker B, Liu F, Mathew G, Levitsky I, Gutierrez O D, Hintz R L: Characterization of a direct, non-extraction immunoradiometric assay for free IGF-I. Presented at the 76th annual meeting of the Endocrine Society, Anaheim, 1994 (abstract #939).

150. Haddad, I. A., Ordovas, J. M., Fitzpatrick, T. and Karathanasis, S. K. Linkage, evolution, and expression of the rat apolipoprotein A-I, C-III, and A-IV genes. J. Biol. Chem. 261 (28), 13268-13277 (1986).
151. U.S. Pat. No. 5,869,330, issued Feb. 9, 1999, Scherer et al.
152. Groenendijk M, Cantor R M, de Bruin T W, Dallinga-Thie G M (2001) The apoAI-CIII-AIV gene cluster. Atherosclerosis 157: 1-11.
153. Chobanian A V, Bakris G L, Black H R, Cushman W C, Green L A, et al. (2003) The Seventh Report of the Joint National Committee on Prevention, Detection, Evaluation, and Treatment of High Blood Pressure: the JNC 7 report. JAMA 289: 2560-2572.
154. Karathanasis S K. Apolipoprotein multigene family: tandem organization of human apolipoprotein AI, CIII, and AIV genes. Proc Natl Acad Sci USA 82:6374-78, 1985.
155. Garasto S, Rose G, Derango F, Berardelli M, Corsonello A, et al. (2003) The study of APOA1, APOC3 and APOA4 variability in healthy ageing people reveals another paradox in the oldest old subjects. Ann Hum Genet 67: 54-62.
156. Panza F, D'Introno A, Colacicco A M, Capurso C, Capurso S, et al. (2004) Vascular genetic factors and human longevity. Mech Ageing Dev 125: 169-178.
157. Wang C S, McConathy W J, Kloer H U, Alaupovic P (1985) Modulation of lipoprotein lipase activity by apolipoproteins. Effect of apolipoprotein C-III. J Clin Invest 75: 384-390.
158. Kashyap M L, Srivastava L S, Hynd B A, Gartside P S, Perisutti G (1981) Quantitation of human apolipoprotein C-III and its subspecie by radioimmunoassay and analytical isoelectric focusing: abnormal plasma triglyceride-rich lipoprotein apolipoprotein C-III subspecie concentrations in hypertriglyceridemia. J Lipid Res 22: 800-810.
159. Ito Y, Azrolan N, O'Connell A, Walsh A, Breslow J L. Hypertriglyceridemia as a result of human apo CIII gene expression in transgenic mice. Science 249:790-3, 1990.
160. Maeda N, Li H, Lee D, Oliver P, Quarfordt S H, et al. (1994) Targeted disruption of the apolipoprotein C-III gene in mice results in hypotriglyceridemia and protection from postprandial hypertriglyceridemia. J Biol Chem 269: 23610-23616.
161. Takahashi T, Hirano T, Okada K, Adachi M (2003) Apolipoprotein CIII deficiency prevents the development of hypertriglyceridemia in streptozotocin-induced diabetic mice. Metabolism 52: 1354-1359.
162. van Duijn C M, de Knijff P, Cruts M, et al. Apolipoprotein E4 allele in a population-based study of early-onset Alzheimer's disease. Nat Genet. 1994; 7(1):74-8.
163. Cnop M, Havel P J, Utzschneider K M, et al. Relationship of adiponectin to body fat distribution, insulin sensitivity and plasma lipoproteins: evidence for independent roles of age and sex. Diabetologia 2003; 46(4):459-69.
164. Pollin T I, Tanner K, O'Connell J R, et al. Linkage of Plasma Adiponectin Levels to 3q27 Explained by Association With Variation in the APM1 Gene. Diabetes 2005; 54(1):268-74.

What is claimed is:

1. A method for identifying a compound for decreasing hypertension and/or increasing insulin sensitivity in a subject, the method comprising
    determining whether or not a compound inhibits the activity of apoliprotein C-3 (APOC-3) from a subject, wherein a compound that inhibits the activity of apoliprotein C-3 (APOC-3) is identified as a putative compound for decreasing hypertension and/or increasing insulin sensitivity, and
    determining whether or not the compound decreases hypertension and/or increases insulin sensitivity in the subject.

2. The method of claim 1, wherein the compound inhibits the activity of apolipoprotein C-3 (APOC-3).

3. The method of claim 1, wherein the compound is a putative compound for decreasing hypertension.

4. The method of claim 1, wherein the compound is a putative compound for increasing insulin sensitivity.

5. A method for identifying a compound for decreasing hypertension and/or increasing insulin sensitivity in a subject, the method comprising
    identifying a compound that inhibits the activity of apoliprotein C-3 (APOC-3) from the subject, and
    determining whether or not the compound that inhibits apoliprotein C-3 (APOC-3) activity decreases hypertension and/or increases insulin sensitivity in the subject.

6. The method of claim 5, wherein the compound decreases hypertension.

7. The method of claim 5, wherein the compound increases insulin sensitivity.

* * * * *